(12) United States Patent
Tominaga et al.

(10) Patent No.: US 11,850,232 B2
(45) Date of Patent: Dec. 26, 2023

(54) DRUG FOR TREATING OR PREVENTING CEREBRAL HEMORRHAGE, AND METHOD FOR TREATING OR PREVENTING CEREBRAL HEMORRHAGE USING THE DRUG

(71) Applicant: BIOGEN MA INC., Cambridge, MA (US)

(72) Inventors: Teiji Tominaga, Sendai (JP); Kuniyasu Niizuma, Sendai (JP)

(73) Assignee: BIOGEN MA INC., Cambridge, MA (US)

( * ) Notice: Subject to any disclaimer, the term of this patent is extended or adjusted under 35 U.S.C. 154(b) by 150 days.

(21) Appl. No.: 17/106,862

(22) Filed: Nov. 30, 2020

(65) Prior Publication Data

US 2021/0322381 A1    Oct. 21, 2021

(30) Foreign Application Priority Data

Nov. 20, 2019   (JP) ................. 2019-209932

(51) Int. Cl.
*A61K 31/407* (2006.01)
*A61P 7/04* (2006.01)

(52) U.S. Cl.
CPC .......... *A61K 31/407* (2013.01); *A61P 7/04* (2018.01)

(58) Field of Classification Search
CPC .................................................. A61K 31/407
See application file for complete search history.

(56) References Cited

U.S. PATENT DOCUMENTS

| | | | |
|---|---|---|---|
| 7,361,493 B1 | 4/2008 | Hammond et al. | |
| 9,078,880 B2 * | 7/2015 | Honda | A61P 43/00 |
| RE47,684 E * | 11/2019 | Kazuo | A61P 9/10 |
| RE49,351 E * | 1/2023 | Honda | A61P 43/00 |
| 2008/0293799 A1 | 11/2008 | Hasumi et al. | |
| 2009/0216028 A1 | 8/2009 | Hasumi et al. | |

FOREIGN PATENT DOCUMENTS

| | | |
|---|---|---|
| CN | 101346471 A | 1/2009 |
| JP | 2002-065288 A | 3/2002 |
| JP | 2004-224737 A | 8/2004 |
| JP | 2004-224738 A | 8/2004 |
| JP | 2008-201688 A | 9/2008 |
| JP | 2009-132724 A | 6/2009 |
| JP | 2009-215216 A | 9/2009 |
| RE | 47684 E | 11/2019 |
| WO | 2004-002488 A1 | 1/2004 |
| WO | 2007-40082 A1 | 4/2007 |
| WO | 2007-094071 A | 8/2007 |
| WO | 2007/111203 A1 | 10/2007 |
| WO | 2011-004620 A1 | 12/2012 |

OTHER PUBLICATIONS

Matsumoto, Journal of Biological Chemistry (2014), 289(52), 35826-35838.*
West, Solid State Chemistry and Its Applications, john Wiley & Sons, 1984.*
Wolff, Burger's medicinal Chemistry and Drug Discovery, vol. 1, Principles and Practice, John Wiley & sons, New York, 1997.*
Longa et al., "Reversible Middle Cerebral Artery Occlusion Without Craniectomy in Rats", Stroke, 1989, vol. 20, No. 1, pp. 84-91.
FEBS Letters 1997;418:58-62.
J Biol Chem 2014;289:35826-35838, Dec. 26, 2014.
Adams et al. (1996) "Guidelines for Thrombolytic Therapy for Acute Stroke: A Supplement to the Guidelines for the Management of Patients with Acute Ischemic Stroke, A Statement for Healthcare Professionals from a Special Writing Group of the Stroke Council, American Heart Association", Circulation, 94, pp. 1167-1174.Engl. Abstract.
Adams et al. (May 2007) "Guidelines for the Early Management of Adults with Ischemic Stroke", Stroke, pp. 1655-1711.
Adibhatla et al., Jun. 2008, "Tissue Plasminogen Activator (tPA) and Matrix Metalloproteinases in the Pathogenesis of Stroke: Therapeutic Strategies", CNS Neurol Disord Drug Targets, 7(3), pp. 243-253.
Benakis et al., 2009, "Inflammation and stroke", Kardiovaskulare Medizin, 12(5), pp. 143-150.
Cheng et al., Jan. 2004, "Neuroprotection for Ischemic Stroke: Two Decades of Success and Failure", The Journal of the American Society for Experimental NeuroTherapeutics, vol. 1, pp. 36-45.
Cuadrado et al., Jul. 2008, "Tissue pasminogen activator (t-PA) promotes neutrophil degranulation and MMP-9 release", Journal of Leukocyte Biology, vol. 84, pp. 207-214.
Donnan et al., "Stroke", The Lancet, 2008, vol. 371, pp. 1612-1623.
Donnan, Geoffrey A., Jan. 2008, "A New Road Map for Neuroprotection", The 2007 Feinberg Lecture, pp. 242-248.
Gravanis et al., "tPA as a therapeutic target in stroke", Expert Opin. Ther. Targets, 2008, vol. 12, No. 2.

(Continued)

*Primary Examiner* — Nizal S Chandrakumar
(74) *Attorney, Agent, or Firm* — Troutman Pepper Hamilton Sanders LLP

(57) ABSTRACT

A drug used for treating or preventing cerebral hemorrhage, the drug including, as an active ingredient, a compound represented by the following Formula (I) or a pharmaceutically acceptable salt, ester, or solvate thereof:

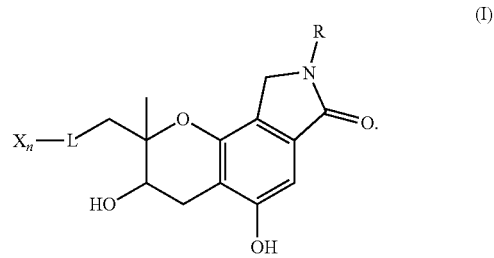

(I)

7 Claims, 34 Drawing Sheets

(56) References Cited

OTHER PUBLICATIONS

Hacke et al., Randomised double blind placebo controlled trial of thrombolytic therapy with intravenouss alteplase in acute ischaemic stroke: (ECASS II), The Lancet, vol. 352, Oct. 17, 1998, pp. 1245-1251.
Hasumi et al., "Isolation of SMTP-3, 4, 5 and -6 Novel Analogs of Staplabin and their Effects on Plasminogen Activation and Fibrinolysis", The Journal of Antibiotics, vol. 51, No. 12, 1998, pp. 1059-1068.
Hu et al. (2000) "Activation of Fibrinolysis by SMTP-7 and -8, Novel Staplabin Analogs with a Pseudosymmetric Structure", The Journal of Antibiotics, vol. 53, No. 3, Mar. 2000, pp. 241-247.
Huang et al., "Development and Validation of Oxygen Radical Absorbance Capacity Assay for Lipophillic Antioxidants Using Randomly Methylated [beta]-Cyclodextrin as a Solubility Enhancer", Journal of Agricultural and Food Chemistry, 2002, vol. 50, No. 7, pp. 1815-1821.
Internet Stroke Center on the Wayback Machine http//:www.strokecenter.org.80/pat/ais.thm, "About Stroke", copyright 1997-2002.
Ito et al., "SMTP-7, a new thrombolytic agent, decreases hemorrhagic transformation after transient middle cerebral artery occulusion under warfarin anticoagulation in mice", Brain Research, 2014, vol. 1578, pp. 38-48.
Kano et al. "Hemorrhagic transformation after fibrinolytic therapy with tissue plasminogen activator in a rat thromboembolic model of stroke", Brain Research, 2000, vol. 854, pp. 245-248.
Kilic et al., "Aggravation of focal cerebral ischemia by tissue plasminogen activator is reversed by 3-hydroxy-3-methylglutaryl coenzyme a reductase inhibitor but does not depend on endothelial NO synthase", Stroke, vol. 36, No. 2, Feb. 2005, pp. 332-336.
Kito et al., "Experimental thromboembolic stroke in cynomolgus monkey", Journal of Neuroscience Methods, 2001; vol. 105, pp. 45-53.
Kohyama et al., "SMTP-1 and -2, Novel Analogs of Staplabin Produced by Stachybotrys Microspora", The Journal of Antibiotics, 1997, vol. 50, No. 2, pp. 172-174.
Lansberg et al., "Efficacy and safety of tissue plasminogen activator 3 to 4.5 hours after acute ischemic stroke: a meta-analysis", Stroke, 2009, vol. 40, No. 7, pp. 2438-2441.
Maeda et al., "A combined treatment with tacrolimus (FK506) and recombinant tissue plasminogen activator for thrombotic focal cerebral ischemia in rats: Increased neuroprotective efficacy and extended therapeutic time window", Journal of Cerebral Blood Flow and Metabolism, vol. 22, No. 10, Oct. 2002, pp. 1205-1211.
Nakagawara et al., "Treatment strategy for Acute Stage Cerebral Stroke Thrombolytic Therapy for Cardiogenic Cerebral Embolism", Medicina, 2000, vol. 37, No. 7, pp. 1114-1116.
Nozawa et al. (1997) "Stachybotrin C and Parvisporin, Novel Neurotogenic Compounds I. Taxonomy, Isolation, Physico-chemical and Biological Properties, The Journal of Antibiotics", vol. 50, No. 8, (1997), pp. 635-640.
Partridge, "Building a Better Clot-Buster: rt-PA and Combination Therapy", Psychiatric Times, 2007.
Sacchetti, Maria Luisa, Jun. 2008, "Is it Time to Definitely Abandon Neuroprotection in Acute Ischemic Stroke", Stroke, pp. 1659-1660.
Shibata et al., "Evaluation of the effects of a new series of SMTPs in the acetic acide-induced embolic cerebral infarct mouse model", European Journal of Pharmacology, 2018, vol. 818, pp. 221-227.
Shinohara et al., "Staplabin, a Novel Fungal Triprenyl Phenol which stimulates the Binding of Plasminogen to Fibrin and U937 Cells", The Journal of Antibiotics, 1996, vol. 49, No. 10, pp. 961-966.
Terr (2001) "Strachybotrys: relevance to human disease," Annals of Allergy, Asthma and Immunology, Dec. 2001, vol. 87, pp. 57-62.
The Lancet, vol. 363, Mar. 6, 2004, www.thelancet.com, "Association of outcome with early stoke treatment; pooled analysis of Atlantis, ECASS, and NINDS rt-PA stroke trials", pp. 768-774.
Types of Stroke, last reviewed on Oct. 23, 2012, available at http:www.strokeassociation.org/STROKEORG/AboutStroke/TypesofStroke/Types-of-Stroke_UCM_308531_SubHomePage.jsp.
Yoneda et al., "Feature Article: Treatment of Acute Stage Cerebral Infarction Drug Therapy in Acute Stage"; Geriatric Medicine, 1998, vol. 36, No. 5, pp. 679-684.
Chinese Patent Office Action for Chinese Appln. Serial No. 201080030009.7, dated Jan. 14, 2013, 10 pages—English.
European Search Report issued in EP Appln. No. 10796931.3, dated Nov. 2, 2012, 6 pages (English).
International Search Report and Written Opinion issued in PCT/IB2020/061485 dated Jan. 26, 2021.
International Search Report and Written Opinion issued in PCT/JP2020/044574 dated Jan. 26, 2021 (English Translation of Written Opinion unavailable).
PCT/JP2010/051711, International Search Report, dated Mar. 23, 2010, 2 pgs.—Japanese; 2 pgs.—English.
PCT/JP2010/051711, Written Opinion of IPEA dated filed Feb. 15, 2011, 6 pgs—Japanese; 7 pgs—English, Cert. of Trans.
Huang et al., "Reduction of Ischemia Reperfusion-Related Brain Hemorrhage by Stachybotrys Microspora Triprenyl Phenol-7 in Mice with Antioxidant Effects", Journal of Stroke and Cerebrovascular Diseases, 2018, vol. 27, No. 12, pp. 3521-3528.
Office Action Issued in EA Application No. 202291522, dated May 22, 2023.
Translation of Written Opinion issued in PCT/JP2020/044574 dated Jan. 26, 2021. (translation only—JP language document previously submitted).

\* cited by examiner

Blood Clot

ICH

Vehicle

SMTP7

DRUG FOR TREATING OR PREVENTING CEREBRAL HEMORRHAGE, AND METHOD FOR TREATING OR PREVENTING CEREBRAL HEMORRHAGE USING THE DRUG

CROSS-REFERENCE TO RELATED APPLICATIONS

This application claims foreign priority from Japanese Patent Application No. 2019-209932, filed Nov. 20, 2019.

TECHNICAL FIELD

The present disclosure relates to a drug for treating or preventing cerebral hemorrhage, and a method of treating or preventing cerebral hemorrhage using the drug.

BACKGROUND ART

Cerebral hemorrhage is a general term for symptoms of bleeding caused by rupture of a blood vessel in the brain, and can be classified into intracerebral hemorrhage, subarachnoid hemorrhage, and the like depending on the site of bleeding. The blood overflowing from the blood vessel forms a hematoma, and the hematoma can directly damage the brain. Further, formation of an edema can increase the pressure in the brain, causing brain damage due to the compression of the brain.

There has been no effective drug treatment for cerebral hemorrhage, and measures such as surgery to remove a hematoma from the brain have been taken.

SMTP (*Stachybotrys microspora* triprenyl phenol) compounds are a group of compounds having a triprenyl phenol skeleton produced by a filamentous bacterium, and are known to have a thrombolysis promotion action or a vascularization inhibitory action according to Japanese Patent Laid-Open (JP-A) Nos. 2004-224737 and 2004-224738, and International Publication No. WO 2007/111203. With respect to the thrombolysis promotion action, an action mechanism is indicated by FEBS Letter, 1997; 418: 58-62, that an SMTP compound causes a conformational change in the plasminogen resulting in increasing the sensitivity of the plasminogen to t-PA and the binding of the plasminogen onto a thrombus etc. so as to promote lysis of the thrombus. Further, J Biol Chem 2014; 289: 35826-35838 indicates that an SMTP compound has a favorable anti-inflammatory action.

SUMMARY OF INVENTION

Technical Problem

The inventors have found that a compound represented by Formula (I) or a pharmaceutically acceptable salt, ester, or solvate thereof has an effect in the treatment or prevention of cerebral hemorrhage.

Since there has been no effective pharmacological treatment for cerebral hemorrhage, it is surprising that the compound represented by Formula (I) or a pharmaceutically acceptable salt, ester, or solvate thereof produce an effect in the treatment or prevention of cerebral hemorrhage.

Any effect of the compound represented by Formula (I) on cerebral hemorrhage is not described or suggested in JP-A Nos. 2004-224737 and 2004-224738, WO 2007/111203, FEBS Letter 1997; 418: 58-62, and J Biol Chem 2014; 289: 35826-35838.

An embodiment according to the present disclosure aims to provide a drug excellent in treating or preventing cerebral hemorrhage, and a new method of treating or preventing cerebral hemorrhage.

Solution to Problem

Means for solving the problems include the following aspects.

<1> A drug used for treating or preventing cerebral hemorrhage, the drug including, as an active ingredient, a compound represented by the following Formula (I) or a pharmaceutically acceptable salt, ester, or solvate thereof:

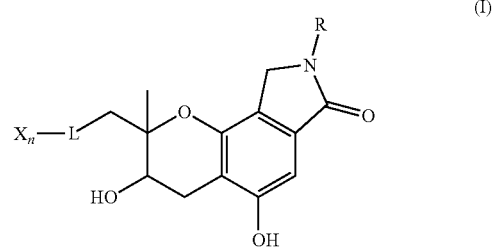

(I)

wherein, in Formula (I), L represents an aliphatic hydrocarbon group having from 4 to 10 carbon atoms, X represents a hydroxy group or a carboxy group, n represents an integer from 0 to 2, and R represents a hydrogen atom or a substituent having a molecular weight of 1000 or less.

<2> The drug according to <1>, wherein the compound represented by Formula (I) or a pharmaceutically acceptable salt, ester, or solvate thereof is a compound represented by the following Formula (IA) or a pharmaceutically acceptable salt, ester, or solvate thereof:

(IA)

wherein, in Formula (IA), X is —CHY—C(CH$_3$)$_2$Z, wherein each of Y and Z is independently —H or —OH, or Y and Z together form a single bond, and R represents a hydrogen atom or a substituent having a molecular weight of 1,000 or less.

<3> The drug according to <1> or <2>, wherein the compound represented by Formula (I) or a pharmaceutically acceptable salt, ester, or solvate thereof is a compound represented by the following Formula (II) or Formula (III), or a pharmaceutically acceptable salt, ester, or solvate thereof:

(II)

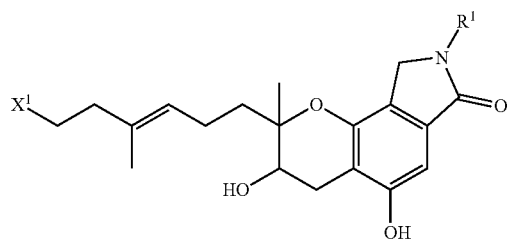

(III)

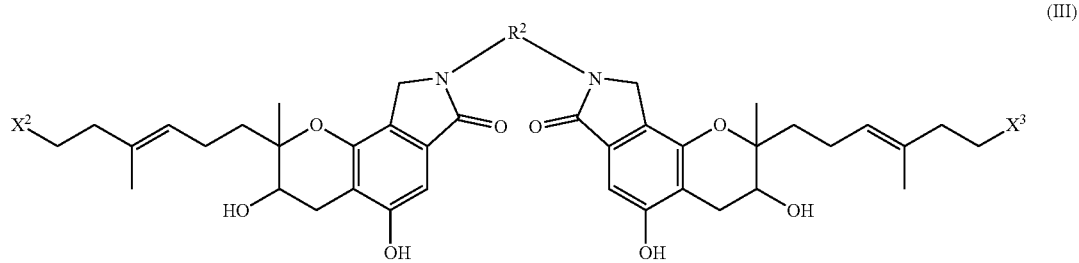

wherein, in Formula (II) or Formula (III), each of $X^1$, $X^2$, and $X^3$ is independently —CHY—C(CH$_3$)$_2$Z, wherein each of Y and Z is independently —H or —OH, or Y and Z together form a single bond, and $R^1$ represents any one of the following (A) to (D):

(A) a residue (provided that —(CH)$_2$—OH is excluded) obtained by removing one amino group from an amino compound selected from the group consisting of: a natural amino acid; a D-form of a natural amino acid; and a compound in which at least one carboxy group in a natural amino acid or a D-isoform of a natural amino acid is substituted with a hydrogen atom, a hydroxy group, or a hydroxymethyl group;

(B) an aromatic group having at least one selected from the group consisting of a carboxy group, a hydroxy group, a sulfonic acid group, and a secondary amino group as a substituent or as a part of a substituent; or an aromatic group that contains a secondary amino group and may contain a nitrogen atom;

(C) an aromatic amino acid residue represented by the following Formula (II-1):

(II-1)

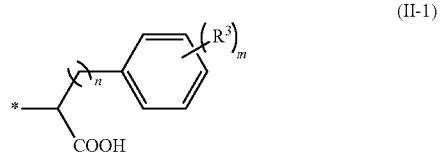

wherein, $R^3$ is a substituent that may or may not be present, and if present, represents a hydroxy group, a carboxy group, or an alkyl group having from 1 to 5 carbon atoms, n represents an integer of 0 or 1, m represents an integer from 0 to 5, and * represents a bonding site; and (D) a substituent represented by -L$^1$-L$^2$-R$^4$, wherein L$^1$ represents a linking group that is an alkylene group having from 1 to 4 carbon atoms and containing a carboxy group, L$^2$ represents a linking group represented by —NH—C(=O)— or —NH—C(=S)—NH—, and R$^4$ represents a 9-fluorenylalkyloxy group that contains an alkyloxy group having from 1 to 3 carbon atoms, or a polyheterocyclic group represented by the following Formula (II-2) (in Formula (II-2), * represents a bonding site):

(II-2)

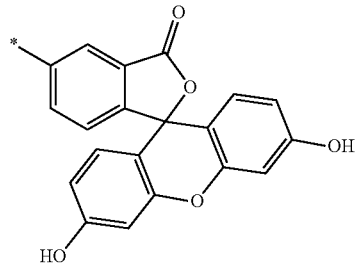

wherein $R^2$ represents a residue obtained by removing two amino groups from an amino compound selected from the group consisting of: a natural amino acid containing two amino groups; a D-isoform of a natural amino acid containing two amino groups; a compound in which at least one carboxy group of a natural amino acid containing two amino groups or a D-isoform of a natural amino acid containing two amino groups is substituted with a hydrogen atom, a hydroxy group, or a hydroxymethyl group; a compound represented by H$_2$N—CH(COOH)—(CH$_2$)$_n$—NH$_2$ (wherein n is an integer from 0 to 9); and a compound represented by H$_2$N—CH(COOH)—(CH$_2$)$_m$—S$_p$—(CH$_2$)$_q$—CH(COOH)—NH$_2$ (wherein each of m, p, and q is independently an integer from 0 to 9).

<4> The drug according to any one of <1> to <3>, wherein the compound represented by Formula (I) or a pharmaceutically acceptable salt, ester, or solvate thereof is a compound selected from the group consisting of the following SMTP-0, SMTP-1, SMTP-4, SMTP-5D, SMTP-6, SMTP-7, SMTP-8, SMTP-11 to SMTP-14, SMTP-18 to SMTP-29, SMTP-36, SMTP-37, SMTP-42, SMTP-43, SMTP-43D, SMTP-44, SMTP-44D, SMTP-46, and SMTP-47, or a pharmaceutically acceptable salt, ester, or solvate thereof:
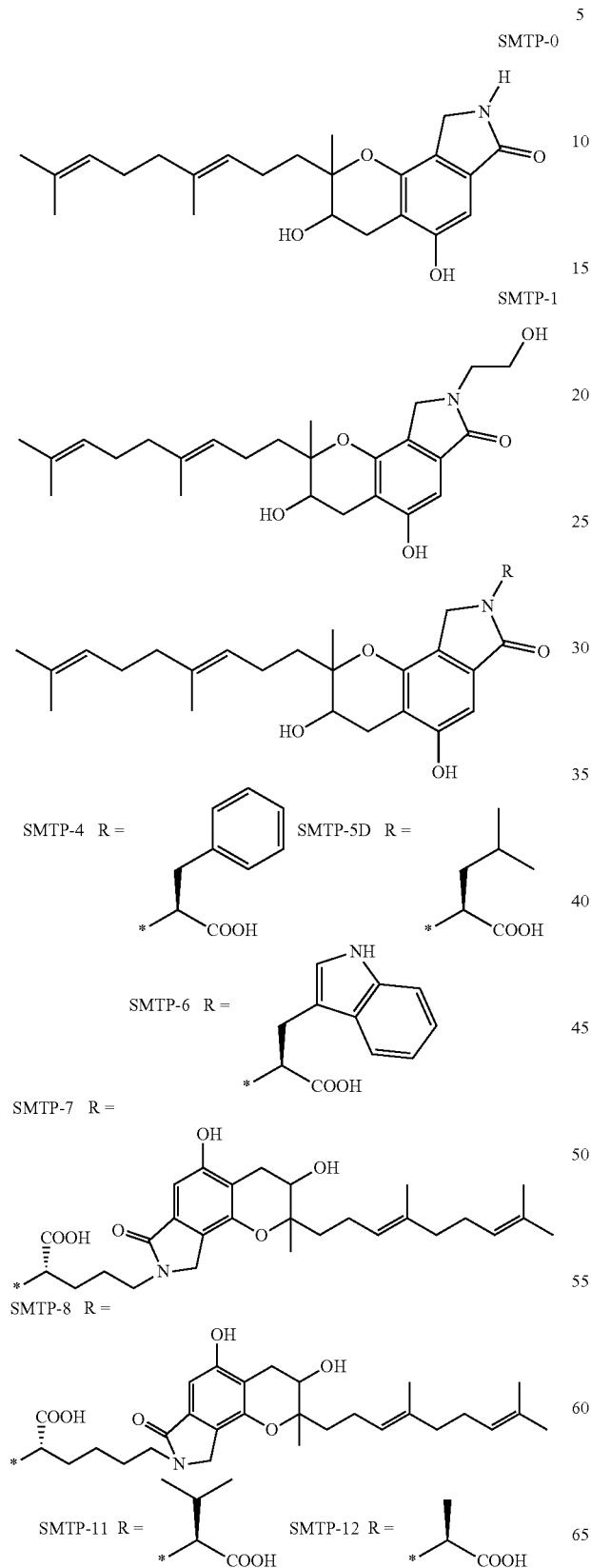
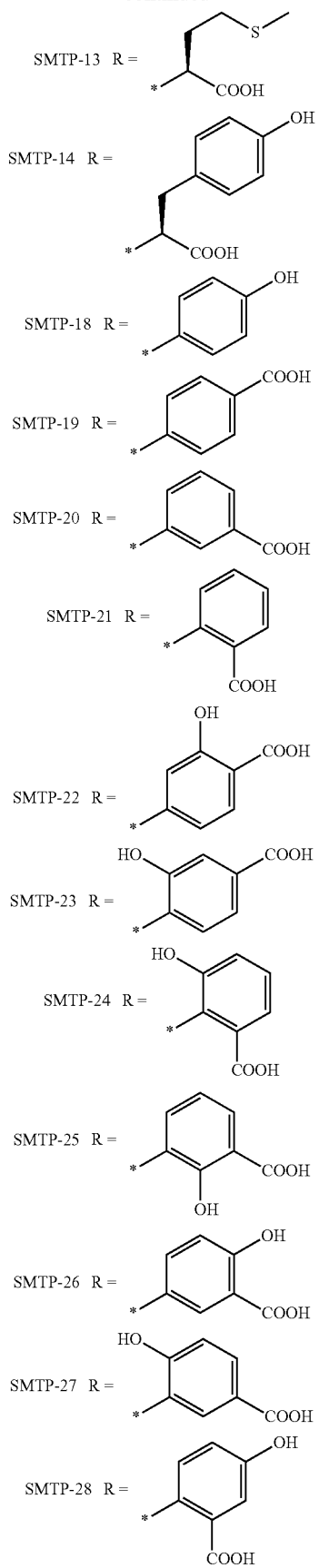

-continued

SMTP-29 R =
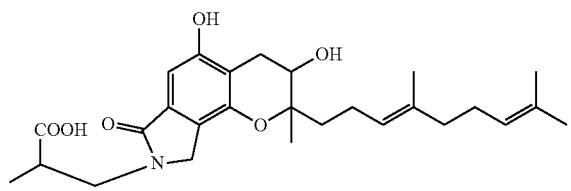

SMTP-36 R =
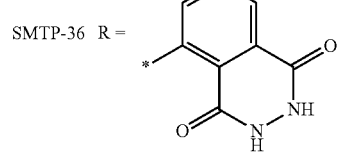

SMTP-37 R =
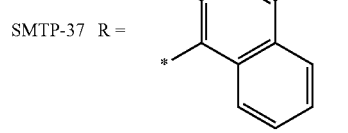

SMTP-42 R =
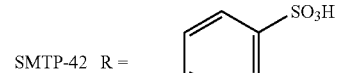

SMTP-43 R =     SMTP-43D R =
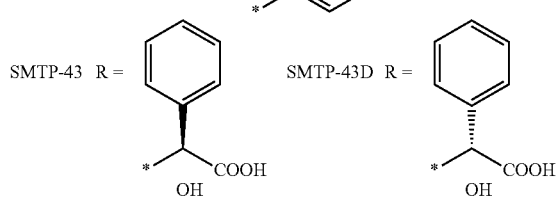

SMTP-44 R =     SMTP-44D R =
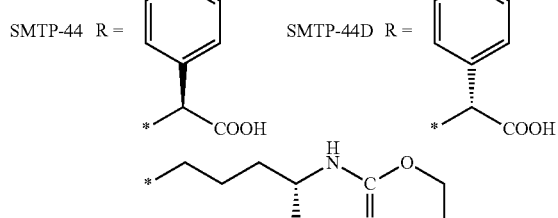

SMTP-46 R =

SMTP-47 R =
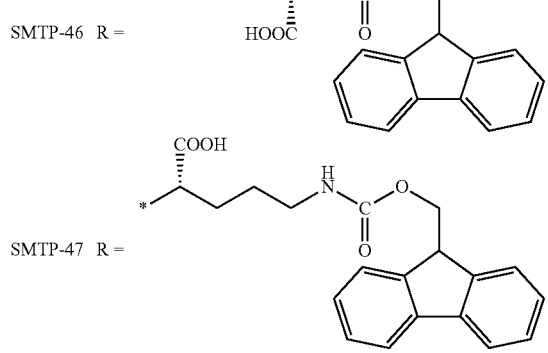

wherein * represents a bonding site.

<5> The drug according to <4>, wherein the compound represented by Formula (I) or a pharmaceutically acceptable salt, ester, or solvate thereof is SMTP-7 or a pharmaceutically acceptable salt, ester, or solvate thereof.

<6> The drug according to any one of <1> to <5>, wherein the cerebral hemorrhage is intracerebral hemorrhage.

<7> The drug according to any one of <1> to <6>, which is administered intracerebrally.

<8> A method of treating a cerebral hemorrhage in a subject, the method including administering a compound represented by the following Formula (I) or a pharmaceutically acceptable salt, ester, or solvate thereof, in an amount effective for treating the cerebral hemorrhage, to the subject suffering from the cerebral hemorrhage:

(I)
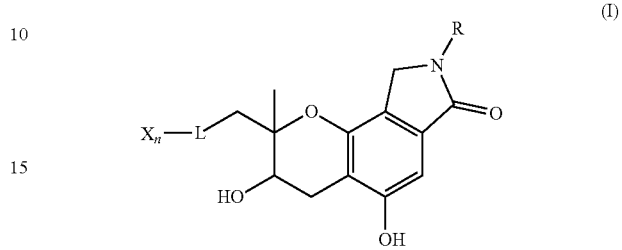

wherein, in Formula (I), L represents an aliphatic hydrocarbon group having from 4 to 10 carbon atoms, X represents a hydroxy group or a carboxy group, n represents an integer from 0 to 2, and R represents a hydrogen atom or a substituent having a molecular weight of 1,000 or less.

<9> A method of preventing a cerebral hemorrhage in a subject, the method including administering a compound represented by the following Formula (I) or a pharmaceutically acceptable salt, ester, or solvate thereof, in an amount effective for preventing cerebral hemorrhage, to the subject at risk of developing cerebral hemorrhage:

(I)
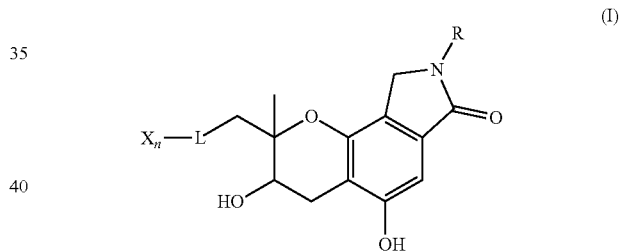

wherein, in Formula (I), L represents an aliphatic hydrocarbon group having from 4 to 10 carbon atoms, X represents a hydroxy group or a carboxy group, n represents an integer from 0 to 2, and R represents a hydrogen atom or a substituent having a molecular weight of 1,000 or less.

<10> The method according to <8> or <9>, wherein the compound represented by Formula (I) or a pharmaceutically acceptable salt, ester, or solvate thereof is a compound represented by the following Formula (IA) or a pharmaceutically acceptable salt, ester, or solvate thereof:

(IA)
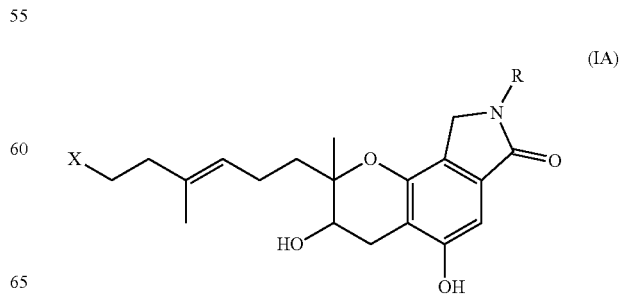

wherein, in Formula (IA), X is —CHY—C(CH$_3$)$_2$Z, wherein each of Y and Z is independently —H or —OH, or Y and Z together form a single bond, and R represents a hydrogen atom or a substituent having a molecular weight of 1,000 or less.

<11> The method according to any one of <8> to <10>, wherein the compound represented by Formula (I) or a pharmaceutically acceptable salt, ester, or solvate thereof is a compound represented by the following Formula (II) or Formula (III), or a pharmaceutically acceptable salt, ester, or solvate thereof:

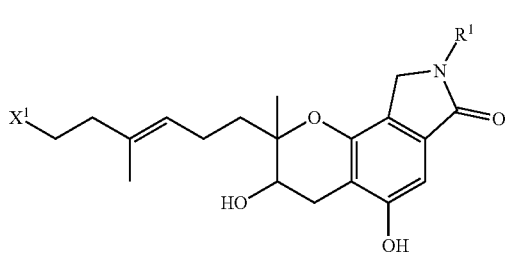

(II)

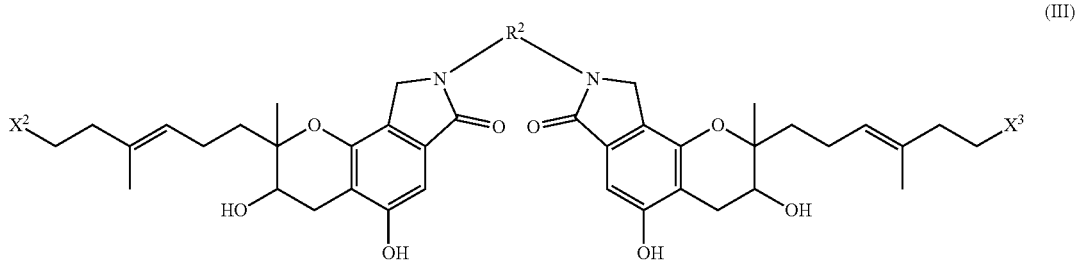

(III)

wherein, in Formula (II) or Formula (III), each of $X^1$, $X^2$, and $X^3$ is independently —CHY—C(CH$_3$)$_2$Z, wherein each of Y and Z is independently —H or —OH, or Y and Z together form a single bond, and $R^1$ represents any one of the following (A) to (D):

(A) a residue (provided that —(CH)$_2$—OH is excluded) obtained by removing one amino group from an amino compound selected from the group consisting of: a natural amino acid; a D-isoform of a natural amino acid; and a compound in which at least one carboxy group in a natural amino acid or a D-isoform of a natural amino acid is substituted with a hydrogen atom, a hydroxy group, or a hydroxymethyl group;

(B) an aromatic group having at least one selected from the group consisting of a carboxy group, a hydroxy group, a sulfonic acid group, and a secondary amino group as a substituent or as part of a substituent; or an aromatic group that contains a secondary amino group and may contain a nitrogen atom;

(C) an aromatic amino acid residue of the following Formula (II-1):

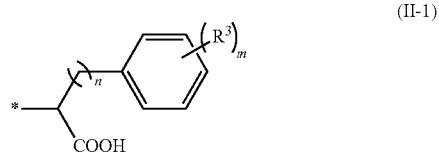

(II-1)

wherein, in Formula (II-1), $R^3$ is a substituent that may or may not be present, and if present, represents a hydroxy group, a carboxy group, or an alkyl group having from 1 to 5 carbon atoms, n represents an integer of 0 or 1, m represents an integer from 0 to 5, and * represents a bonding site; and (D) a substituent represented by -L$^1$-L$^2$-R$^4$, wherein L$^1$ represents a linking group that is an alkylene group having from 1 to 4 carbon atoms and containing a carboxy group, L$^2$ represents a linking group represented by —NH—C(=O)— or —NH—C(=S)—NH—, and R$^4$ represents a 9-fluorenylalkyloxy group that contains an alkyloxy group having from 1 to 3 carbon atoms, or a polyheterocyclic group represented by the following Formula (II-2) (in Formula (II-2), * represents a bonding site):

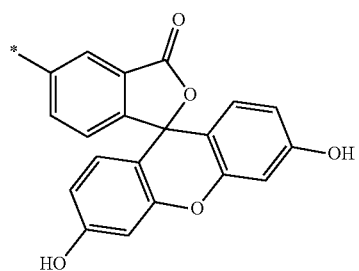

(II-2)

wherein $R^2$ represents a residue obtained by removing two amino groups from an amino compound selected from the group consisting of: a natural amino acid containing two amino groups; a D-isoform of a natural amino acid containing two amino groups; a compound in which at least one carboxy group of a natural amino acid containing two amino groups or a D-isoform of a natural amino acid containing two amino groups is substituted with a hydrogen atom, a hydroxy group, or a hydroxymethyl group; a compound represented by H$_2$N—CH(COOH)—(CH$_2$)$_n$—NH$_2$ (wherein n is an integer from 0 to 9); and a compound represented by H$_2$N—CH(COOH)—(CH$_2$)$_m$—S$_p$—(CH$_2$)$_q$—CH(COOH)—NH$_2$ (wherein each of m, p, and q is independently an integer from 0 to 9).

<12> The method according to any one of <8> to <11>, wherein the compound represented by Formula (I) or the pharmaceutically acceptable salt, ester, or solvate thereof is a compound selected from the group consisting of the following SMTP-0, SMTP-1, SMTP-4, SMTP-5D, SMTP-6, SMTP-7, SMTP-8, SMTP-11 to SMTP-14, SMTP-18 to SMTP-29, SMTP-36, SMTP-37, SMTP-42, SMTP-43, SMTP-43D, SMTP-44, SMTP-44D, SMTP-46, and SMTP-47, or a pharmaceutically acceptable salt, ester, or solvate thereof:
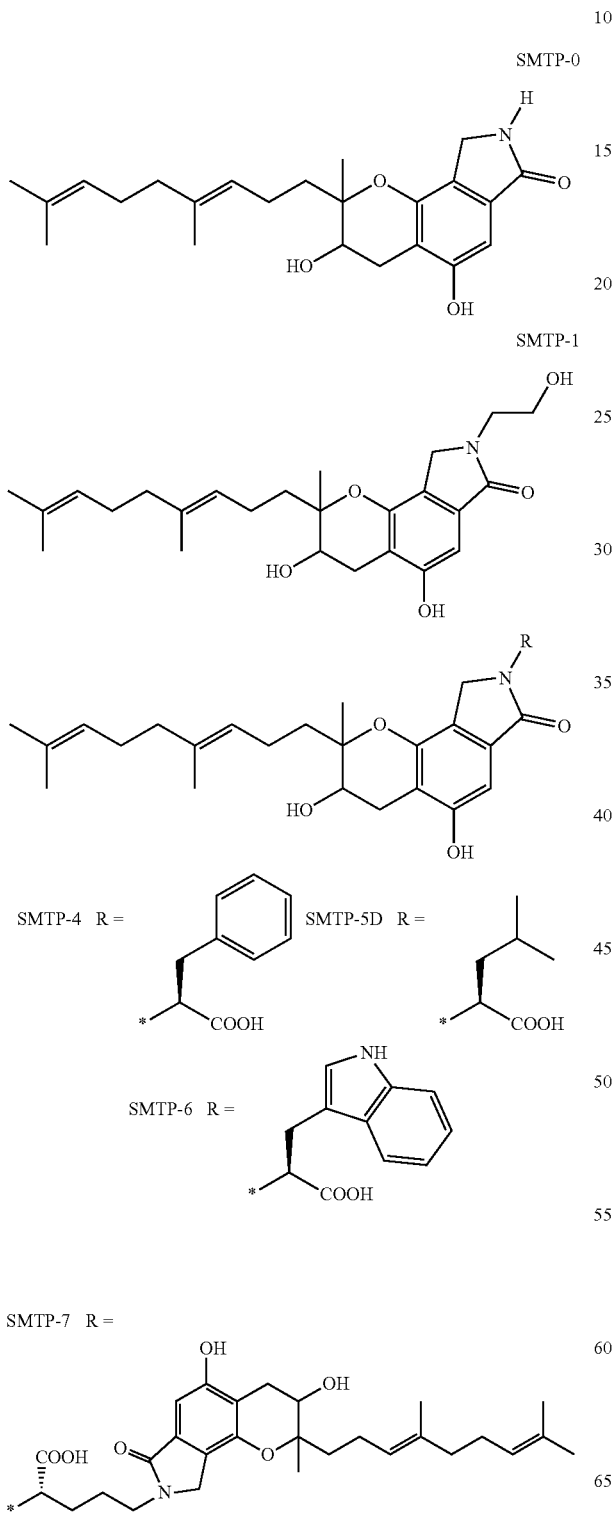
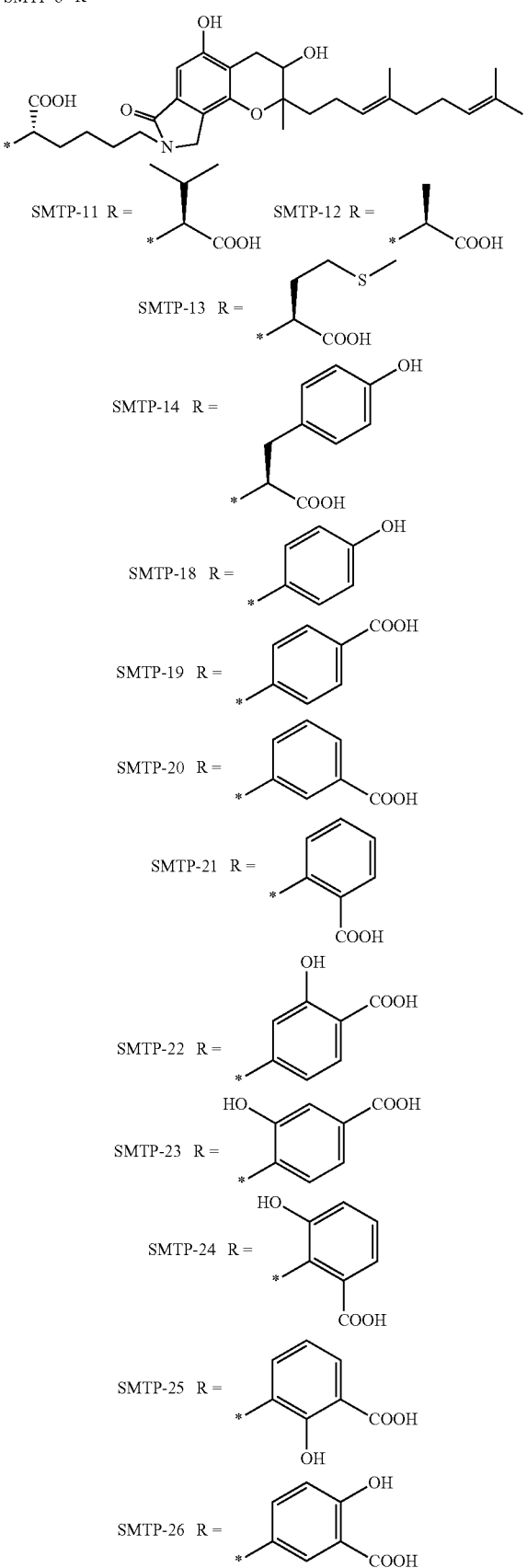

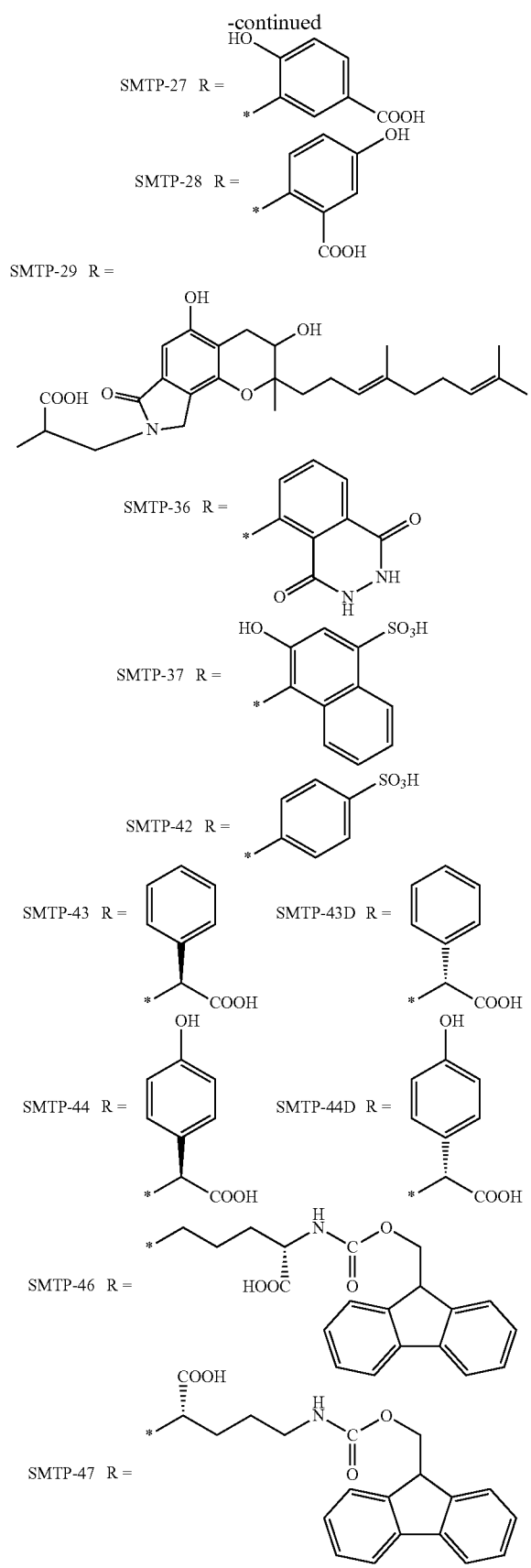

wherein * represents a bonding site.

<13> The method according to <12>, wherein the compound represented by Formula (I) or a pharmaceutically acceptable salt, ester, or solvate thereof is SMTP-7 or a pharmaceutically acceptable salt, ester, or solvate thereof.

<14> The method according to any one of <8> to <13>, wherein the cerebral hemorrhage is intracerebral hemorrhage.

<15> The method according to any one of <8> to <14>, wherein the compound represented by Formula (I) or a pharmaceutically acceptable salt, ester, or solvate thereof is administered intracerebrally.

<16> A compound represented by Formula (I), or a pharmaceutically acceptable salt, ester, or solvate thereof, for use in treatment or prevention of cerebral hemorrhage.

<17> The compound or a pharmaceutically acceptable salt, ester, or solvate thereof, for use according to <16>, wherein the compound represented by Formula (I) or a pharmaceutically acceptable salt, ester, or solvate thereof is a compound represented by Formula (IA) or a pharmaceutically acceptable salt, ester, or solvate thereof.

<18> The compound or a pharmaceutically acceptable salt, ester, or solvate thereof, for use according to <16> or <17>, wherein the compound represented by Formula (I) or a pharmaceutically acceptable salt, ester, or solvate thereof is a compound represented by Formula (II) or Formula (III), or a pharmaceutically acceptable salt, ester, or solvate thereof.

<19> The compound or a pharmaceutically acceptable salt, ester, or solvate thereof, for use according to any one of <16> to <18>, wherein the compound represented by Formula (I) or a pharmaceutically acceptable salt, ester, or solvate thereof is a compound selected from the group consisting of SMTP-0, SMTP-1, SMTP-4, SMTP-5D, SMTP-6, SMTP-7, SMTP-8, SMTP-11 to SMTP-14, SMTP-18 to SMTP-29, SMTP-36, SMTP-37, SMTP-42, SMTP-43, SMTP-43D, SMTP-44, SMTP-44D, SMTP-46, and SMTP-47 described above, or a pharmaceutically acceptable salt, ester, or solvate thereof.

<20> The compound or a pharmaceutically acceptable salt, ester, or solvate thereof, for use according to <19>, wherein the compound represented by Formula (I) or a pharmaceutically acceptable salt, ester, or solvate thereof is SMTP-7 or a pharmaceutically acceptable salt, ester, or solvate thereof.

<21> The compound or a pharmaceutically acceptable salt, ester, or solvate thereof, for use according to any one of <16> to <20>, wherein the cerebral hemorrhage is intracerebral hemorrhage.

<22> The compound or a pharmaceutically acceptable salt, ester, or solvate thereof, for use according to any one of <16> to <21>, wherein the compound represented by Formula (I) or a pharmaceutically acceptable salt, ester, or solvate thereof is administered intracerebrally.

<23> Use of a compound represented by Formula (I) or a pharmaceutically acceptable salt, ester, or solvate thereof, for the manufacture of a medicament for treating or preventing cerebral hemorrhage.

<24> The use according to <23>, wherein the compound represented by Formula (I) or a pharmaceutically acceptable salt, ester, or solvate thereof is a compound represented by Formula (IA) or a pharmaceutically acceptable salt, ester, or solvate thereof.

<25> The use according to <23> or <24>, wherein the compound represented by Formula (I) or a pharmaceutically acceptable salt, ester, or solvate thereof is a compound represented by Formula (II) or Formula (III), or a pharmaceutically acceptable salt, ester, or solvate thereof.

<26> The use according to any one of <23> to <26>, wherein the compound represented by Formula (I) or a pharmaceutically acceptable salt, ester, or solvate thereof is a compound selected from the group consisting of SMTP-0, SMTP-1, SMTP-4, SMTP-5D, SMTP-6, SMTP-7, SMTP-8, SMTP-11 to SMTP-14, SMTP-18 to SMTP-29, SMTP-36, SMTP-37, SMTP-42, SMTP-43, SMTP-43D, SMTP-44, SMTP-44D, SMTP-46, and SMTP-47 described above, or a pharmaceutically acceptable salt, ester, or solvate thereof.

<27> The use according to <26>, wherein the compound represented by Formula (I) or a pharmaceutically acceptable salt, ester, or solvate thereof is SMTP-7 or a pharmaceutically acceptable salt, ester, or solvate thereof.

<28> The use according to any one of <23> to <27>, wherein the cerebral hemorrhage is intracerebral hemorrhage.

<29> The use according to any one of <23> to <28>, wherein the medicament is a medicament for intracerebral administration.

Advantageous Effects of Invention

According to embodiments of the present disclosure, a drug producing an excellent effect in the treatment or prevention of cerebral hemorrhage, and a novel application of the compound represented by Formula (I) or a pharmaceutically acceptable salt, ester, or solvate thereof as a pharmaceutical, can be provided.

DETAILED DESCRIPTION OF THE INVENTION

Figure 1A:
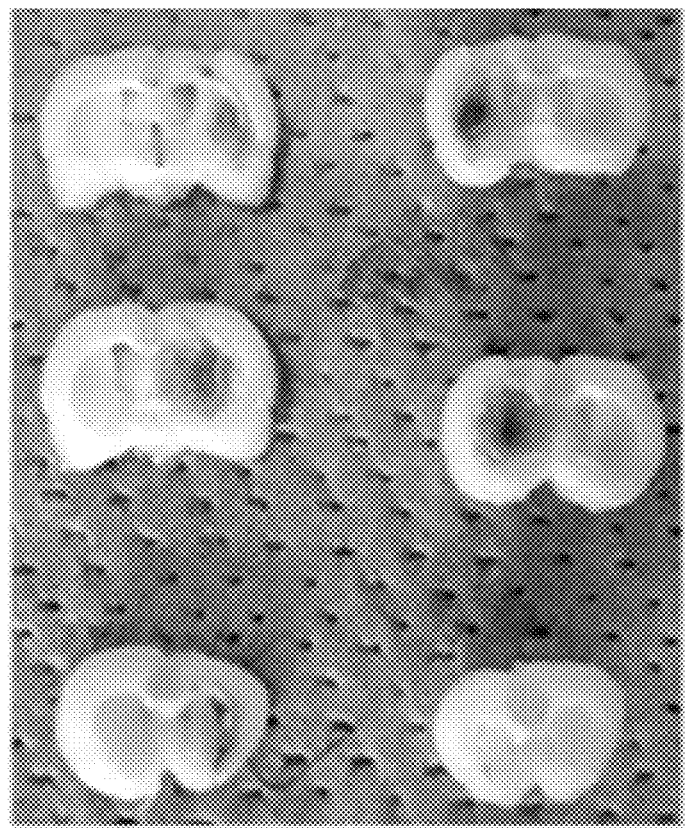
FIG. 1A provides a photograph of a brain section in a study using an animal model of cerebral hemorrhage, FIG. 1B provides a photograph of a brain section in a study using an animal model of cerebral hemorrhage.

The present disclosure will be explained below in detail. The description of structural elements described below may be made based on representative embodiments of the present disclosure, but the present disclosure is not limited to these embodiments.

With regard to numerical ranges described in a stepwise manner herein, an upper limit value or a lower limit value of one numerical range described in a stepwise manner may be replaced with an upper limit value or a lower limit value of another numerical range described in a stepwise manner. Regarding a numerical range described herein, an upper limit value or a lower limit value of the numerical value range may be replaced with a value shown in a working example.

In the present disclosure, the amount of each component in a composition such as a drug means, when plural substances corresponding to the same component exist in the composition, a total amount of the plural substances present in the composition unless otherwise specified.

In the notation of a group (atomic group) herein, a notation without a substituted or unsubstituted group includes one without a substituent as well as one with s substituent.

The term "step" as used herein includes not only a separate step but also a step that is not clearly distinguishable from other steps as long as the desired effect of the step is obtained therefrom.

Herein, "% by mass" and "% by weight" are used synonymously, and "part by mass" and "part by weight" are used synonymously.

In the present disclosure, a combination of two or more preferable aspects is a more preferable aspect.

Hereinafter, the present disclosure is explained in more detail.

(Drugs)

The drug according to the present disclosure is a drug used for treating or preventing cerebral hemorrhage, and includes, as an active ingredient, a compound represented by Formula (I) or a pharmaceutically acceptable salt, ester, or solvate thereof. Here, the pharmaceutically acceptable salt, ester, or solvate of the compound represented by the Formula (I) can be obtained from the compound represented by Formula (I) by a conventional method. For this reason, in the description below, the explanation for the salt, ester, or solvate will not be provided each time unless otherwise specified. Further, the explanation for "compound represented by Formula (I)" will apply equally to "pharmaceutically acceptable salt, ester, or solvate of the compound represented by Formula (I)".

<Compound represented by Formula (I)>

The drug according to the present disclosure includes a compound represented by Formula (I) or a pharmaceutically acceptable salt, ester, or solvate thereof.

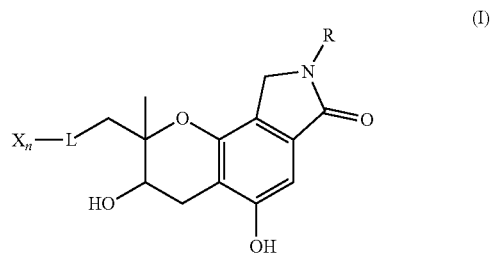

In Formula (I), L represents an aliphatic hydrocarbon group having from 4 to 10 carbon atoms, X represents a hydroxy group or a carboxy group, n represents an integer from 0 to 2, and R represents a hydrogen atom or a substituent having a molecular weight of 1,000 or less.

The aliphatic hydrocarbon group having from 4 to 10 carbon atoms represented by L may be linear, branched, or cyclic, and may contain an unsaturated bond. Among others, the group is preferably a linear or branched aliphatic hydrocarbon group that may contain a unsaturated bond. L is an n+1 valence group.

In Formula (I), the group represented by -L-X$_n$ is preferably a group selected from the group consisting of Formula (V) and Formulae (Y1) to (Y4) below. In Formula (V) and Formulae (Y1) to (Y4), * represents the bonding site to the carbon atom (the carbon atom to which L is bonded) adjacent to the oxygen-containing ring in Formula (I).

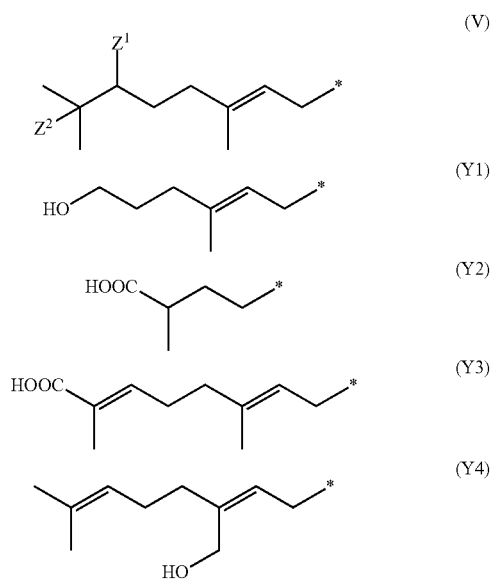

In Formula (V), each of Z$^1$ and Z$^2$ is independently a hydrogen atom or a hydroxy group, or Z$^1$ and Z$^2$ together form a single bond.

From the viewpoint of reducing a hematoma and an edema as described below, the substituent having a molecular weight of 1,000 or less in R of Formula (I) is preferably a substituent having a molecular weight of 900 or less, more preferably a substituent having a molecular weight of 800 or less, and still more preferably a substituent having a molecular weight of 700 or less.

Examples of R in Formula (I) include an α-amino acid (in this case, the nitrogen atom bonded to R is one in an α-amino group of the α-amino acid). The α-amino acid is not particularly limited to any particular amino acid, and may be a natural amino acid or an unnatural amino acid. The α-amino acid may be an amino acid derivative in which a substituent is introduced into a natural amino acid. Furthermore, when an α-amino acid has two or more amino groups, any of the amino groups may be removed. Examples of R also include an amino sugar and a heterocyclic group.

Among others, the α-amino acid is preferably a natural amino acid, a D-isoform of a natural amino acid, or a phenylalanine or phenylglycine that may have at least one substituent selected from the group consisting of a hydroxy group, a carboxy group, and an alkyl group having from 1 to 5 carbon atoms. The α-amino acid is more preferably a natural amino acid, a D-form of a natural amino acid, or a phenylglycine that may have at least one substituent selected from the group consisting of a hydroxy group, a carboxy group, and an alkyl group having from 1 to 5 carbon atoms. Here, "D-form of a natural amino acid" means the D-type optical isomer of a natural amino acid (which is basically the L-type).

The natural amino acid is not particularly limited as long as the amino acid can be found in nature. Examples of the natural amino acid include glycine, alanine, threonine, valine, isoleucine, tyrosine, cysteine, cystine, methionine, histidine, aspartic acid, glutamic acid, asparagine, glutamine, arginine, lysine, hydroxylysine, ornithine, citrulline, homocysteine, 3,4-dihydroxyphenylalanine, homocystine, diaminopimelic acid, diaminopropionic acid, serine, leucine, phenylalanine, and tryptophan.

In the amino acid derivative in which a substituent is introduced into a natural amino acid, examples of the substituent include a nitro group, a hydroxy group, an arylalkyl group having from 7 to 16 carbon atoms, a ureido group, a thioureido group, a carboxy group, and a group formed by removing one hydrogen atom from fluorescamine. The substituent on the amino acid derivative may have an additional substituent if possible. Examples of the additional substituent on the substituent include the same substituents as those of the substituent on the amino acid derivative.

The amino sugar in R of Formula (I) is not particularly limited as long as the amino sugar is a sugar derivative containing at least one amino group. Specific examples thereof include glucosamine, galactosamine, mannosamine, and neuraminic acid.

The heterocyclic group in R of Formula (I) is not particularly limited as long as the group is a cyclic group containing a heteroatom, and may be either an aliphatic heterocyclic group or an aromatic heterocyclic group. Examples of the heteroatom include a nitrogen atom, an oxygen atom, and a sulfur atom.

Among others, the heterocyclic group is preferably a nitrogen-containing heterocyclic group that is a group containing a nitrogen atom as a heteroatom. The heterocyclic group is more preferably a heterocyclic group formed by removing one hydrogen atom from a heterocyclic compound selected from the group consisting of purine, pyridine, pyridazine, pyrrole, imidazole, pyrazole, and pyrazolone, and still more preferably a heterocyclic group formed by removing one hydrogen atom from a heterocyclic compound selected from the group consisting of purine, pyridine, and pyrazolone. The position where a hydrogen atom is removed from the heterocyclic compound is not particularly limited. It is preferable that a hydrogen atom is removed from a carbon atom of the heterocyclic compound, among others.

A heterocyclic group in R may have a substituent. Examples of the substituent on the heterocyclic group include an alkyl group having from 1 to 5 carbon atoms, an aryl group having 14 or less carbon atoms, a carboxy group, a carbamoyl group, and a sulfonic acid group. Of these, at least one selected from a phenyl group and a carbamoyl group is preferable.

The number of substituents in a heterocyclic group is not particularly limited, and the number is preferably 3 or less.

R in Formula (I) may be an alkyl group, for example, an alkyl group having from 2 to 8 carbon atoms. The alkyl group having from 2 to 8 carbon atoms may be linear, branched, or cyclic. Among others, the alkyl group having from 2 to 8 carbon atoms is preferably linear or branched, and more preferably linear. The number of carbon atoms is preferably from 2 to 6. Here, the number of carbon atoms of the alkyl group does not include the number of carbon atoms of a substituent on the alkyl group.

The alkyl group in R may have a substituent. Examples of the substituent on the alkyl group include an alkyl group having from 1 to 5 carbon atoms, an aryl group having 14 or less carbon atoms, an arylalkyl group having 16 or less carbon atoms, a hydroxy group, a carboxy group, a carbamoyl group, a sulfonic acid group, an amino group, a carbamoyloxy group, a ureido group, a thioureido group, an alkyl sulfide group, an alkyl disulfide group, a group formed by removing R from the compound represented by Formula (I), and a group formed by removing one hydrogen atom from fluorescamine. Among others, the substituent is preferably at least one selected from the group consisting of a hydroxy group, a carboxy group, an amino group, a carbamoyloxy group, an arylalkyl group having from 7 to 14 carbon atoms, a thioureido group, a group formed by removing R from the compound represented by Formula (I), and a group formed by removing one hydrogen atom from fluorescamine.

The number of substituents in the alkyl group is not particularly limited, and is preferably 3 or less.

The substituent on the alkyl group may have an additional substituent if possible. Examples of the additional substituent on the substituent include the same substituents as those of the substituent on the alkyl group.

R in Formula (I) may be an aryl group. The aryl group is preferably an aryl group having from 6 to 14 carbon atoms, more preferably an aryl group having from 6 to 10 carbon atoms, and still more preferably a phenyl group.

The aryl group in R may have a substituent. Examples of the substituent on the aryl group include an alkyl group having from 1 to 5 carbon atoms, an aryl group having 14 or less carbon atoms, a hydroxy group, a carboxy group, a sulfonic acid group, a carbamoyl group, and an aryl carbonyl group. Among others, the substituent is preferably at least one selected from the group consisting of a hydroxy group, a carboxy group, a sulfonic acid group, a carbamoyl group, and an aryl carbonyl group.

The number of substituents in the aryl group is not particularly limited, and is preferably 3 or less.

The substituent on the aryl group may have an additional substituent if possible. Examples of the additional substituent on the substituent include the same substituents as those of the substituent on the aryl group. Furthermore, substituents in the aryl group may be bonded to each other to form a ring structure, if possible.

Method of Preparing Compound Represented by Formula (I)

The compound represented by Formula (I) according to the present disclosure may be a compound obtained by a chemical synthesis or a compound obtained by purification of a culture of a filamentous bacterium such as *Stachybotrys microspora*. Examples of the method of obtaining the compound represented by Formula (I) by purification of a culture of a filamentous bacterium include a method including purification of a desired compound from a culture obtained by adding a pre-determined additive organic amino compound to a culture liquid of Stachybotrys microspora. Such a method is described, for example, in JP-A Nos. 2004-224737 and 2004-224738, and WO 2007/111203.

The compound represented by Formula (I) used in the present disclosure may be an enantiomer, a diastereomer, or a mixture of enantiomers or a mixture of diastereomers. The enantiomer, the diastereomer, or the mixture of enantiomers or the mixture of diastereomers can be prepared by a chemical synthesis or by purification of a culture of a filamentous bacterium. In a case in which the preparation is performed by purification of a culture of a filamentous bacterium, a D- or L-form of an additive organic amino compound is added to a culture medium of the filamentous bacterium, and the filamentous bacterium is cultured, thereby obtaining an isomer corresponding to the D- or L-form.

Compound represented by Formula (I)

The compound represented by Formula (I) is preferably a compound represented by the following Formula (IA).

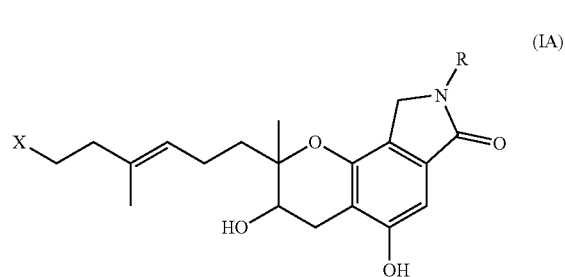

(IA)

In Formula (IA), X is —CHY—C(CH$_3$)$_2$Z, wherein each of Y and Z is independently —H or —OH, or Y and Z together form a single bond, and R represents a hydrogen atom or a substituent having a molecular weight of 1000 or less.

The definition for R in Formula (IA) is the same as that of R in Formula (I), and the preferable aspects of R in Formula (IA) is the same as that of R in Formula (I).

Compound represented by Formula (II)

One of the specific examples of the compound represented by Formula (I) used in the present disclosure is a compound represented by the following Formula (II).

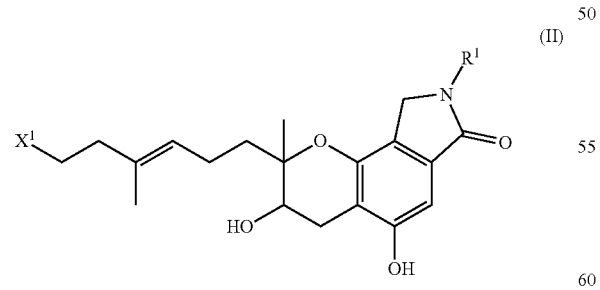

(II)

In Formula (II), X$^1$ is —CHY—C(CH$_3$)$_2$Z, wherein each of Y and Z is independently —H or —OH, or Y and Z together form a single bond, and R$^1$ represents any one of the following (A) to (D).

(A) A residue (provided that —(CH$_2$)—OH is excluded) obtained by removing one amino group from an amino compound selected from the group consisting of: a natural amino acid; a D-isomer of a natural amino acid; and a compound in which at least one carboxy group in a natural amino acid or a D-isoform of a natural amino acid is substituted with a hydrogen atom, a hydroxy group, or a hydroxymethyl group.

(B) An aromatic group having at least one selected from the group consisting of a carboxy group, a hydroxy group, a sulfonic acid group, and a secondary amino group as a substituent or as a part of a substituent; or an aromatic group that contains a secondary amino group and may contain a nitrogen atom.

(C) An aromatic amino acid residue represented by the following Formula (II-1), wherein each R$^3$ is independently a substituent that may or may not be present, and if present, represents a hydroxy group, a carboxy group, or an alkyl group having from 1 to 5 carbon atoms, n represents an integer of 0 or 1, m represents an integer from 0 to 5, and * represents a bonding site to the nitrogen atom (the nitrogen atom bonded to R$^1$) of the nitrogen-containing five-membered ring.

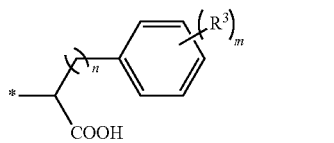

(II-1)

(D) A substituent represented by -L$^1$-L$^2$-R$^4$, wherein L$^1$ represents a linking group that is an alkylene group having from 1 to 4 carbon atoms and containing a carboxy group and, L$^2$ represents a linking group represented by —NH—C(=O)— or —NH—C(=S)—NH—, and R$^4$ represents a 9-fluorenylalkyloxy group that contains an alkyloxy group having from 1 to 3 carbon atoms, or a polyheterocyclic group represented by the following Formula (II-2). In Formula (II-2), * represents a bonding site to L$^2$.

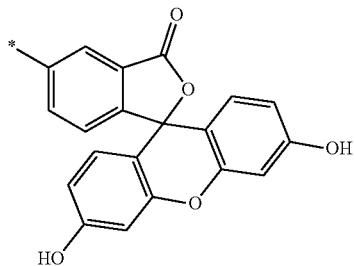

(II-2)

Hereinbelow, the compound represented by Formula (II) in which R$^1$ is (A) above is described.

The (A) is a residue (provided that —(CH$_2$)—OH is excluded) obtained by removing one amino group from an amino compound selected from the group consisting of: a natural amino acid; a D-isomer of a natural amino acid; and a compound in which at least one carboxy group in a natural amino acid or a D-isomer of a natural amino acid is substituted with a hydrogen atom, a hydroxy group, or a hydroxymethyl group.

The natural amino acid is not particularly limited as long as it is an amino acid that can occur naturally, and examples thereof include an α-amino acid, a β-amino acid, a γ-amino acid, and a δ-amino acid. Such an amino acid may be obtained from a natural product, or artificially by means of an organic synthesis or otherwise.

Examples of the natural amino acid include:α-amino acids such as glycine, alanine, threonine, valine, isoleucine, tyrosine, cysteine, cystine, methionine, histidine, aspartic acid, glutamic acid, asparagine, glutamine, arginine, lysine, hydroxylysine, ornithine, citrulline, homocysteine, 3,4-dihydroxyphenylalanine, homocystine, diaminopimelic acid, diaminopropionic acid, serine, leucine, phenylalanine, and tryptophan; β-amino acids such as β-alanine; γ-amino acids such as γ-aminobutyric acid and carnitine; and δ-amino acids such as 5-aminolevulinic acid and 5-aminovaleric acid.

Examples of the compound in which at least one carboxy group in a natural amino acid or a D-isomer of a natural amino acid is substituted with a hydrogen atom, a hydroxy group, or a hydroxymethyl group include an amino alcohol and an amine. Examples of the amino alcohol include 2-aminoethanol.

Specific examples of the compound according to Formula (II) in which $R^1$ is the above (A) include compounds shown in the following Table 1. "Additive Organic Amino Compound" in the table means an additive organic amino compound that is added to a culture liquid of *Stachybotrys microspora* to obtain an intended compound (the same applies hereinafter). In the table, * represents a bonding site to the nitrogen atom (the nitrogen atom bonded to R) of the nitrogen-containing five-membered ring in the structural formula shown in the upper column of the table (the same applies hereinafter).

TABLE 1

SMTPs

| Compound No | Molecular weight | R = | Additive organic amino compound |
|---|---|---|---|
| SMTP-3 | 473.6 | (CH(CH₂OH)COOH) | L-serine |
| SMTP-4 | 533.7 | (CH(CH₂Ph)COOH) | L-phenylalanine |
| SMTP-4Me | 547.7 | (CH(CH₂Ph)COOMe) | L-phenylalanine methyl ester |

TABLE 1-continued

SMTPs

| Compound No | Molecular weight | R = | Additive organic amino compound |
|---|---|---|---|
| SMTP-4D | 533.7 | (CH(CH₂Ph)COOH) | D-phenylalanine |
| SMTP-5 | 499.6 | (CH(CH₂CH(CH₃)₂)COOH) | L-leucine |
| SMTP-5D | 499.6 | (CH(CH₂CH(CH₃)₂)COOH) | D-leucine |
| SMTP-6 | 572.7 | (CH(CH₂-indolyl)COOH) | L-tryptophan |
| SMTP-6D | 572.7 | (CH(CH₂-indolyl)COOH) | D-tryptophan |
| SMTP-10 | 499.6 | (CH(CH(CH₃)CH₂CH₃)COOH) | L-isoleucine |
| SMTP-11 | 485.6 | (CH(CH(CH₃)₂)COOH) | L-valine |
| SMTP-12 | 457.6 | (CH₂COOH) | L-glycine |

TABLE 1-continued

SMTPs

| Compound No | Molecular weight | R = | Additive organic amino compound |
|---|---|---|---|
| SMTP-13 | 517.7 | (structure: *-CH(COOH)-CH2-CH2-S-CH3) | L-methionine |
| SMTP-14 | 549.7 | (structure: *-CH(COOH)-CH2-C6H4-OH) | L-tyrosine |
| SMTP-15 | 542.7 | (structure: *-CH(COOH)-CH2-CH2-CH2-NH-C(=NH)-NH2) | L-arginine |

The compounds shown in Table 1 can be used favorably as the compound represented by Formula (I) used in the present disclosure.

Hereinbelow, the compound represented by Formula (II) in which $R^1$ is the (B) above is described.

The (B) is an aromatic group having at least one selected from the group consisting of a carboxy group, a hydroxy group, a sulfonic group, and a secondary amino group as a substituent or as a part of a substituent; or an aromatic group that contains a secondary amino group and may contain a nitrogen atom.

Examples of the aromatic group include a compound represented by the following structural formulae. In each structural formula, * represents a bonding site to the nitrogen atom (the nitrogen atom bonded to $R^1$) of the nitrogen-containing five-membered ring in Formula (II).

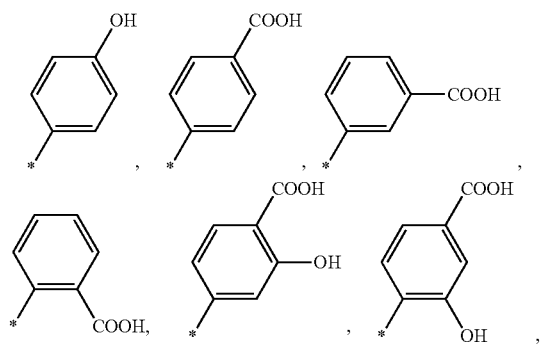

Specific examples of the compound represented by Formula (II) in which $R^1$ is the above (B) include compounds shown in the following Table 2. In the table, * represents a bonding site to the nitrogen atom (the nitrogen atom bonded to R) of the nitrogen-containing five-membered ring in the structural formula shown in the upper column of the table.

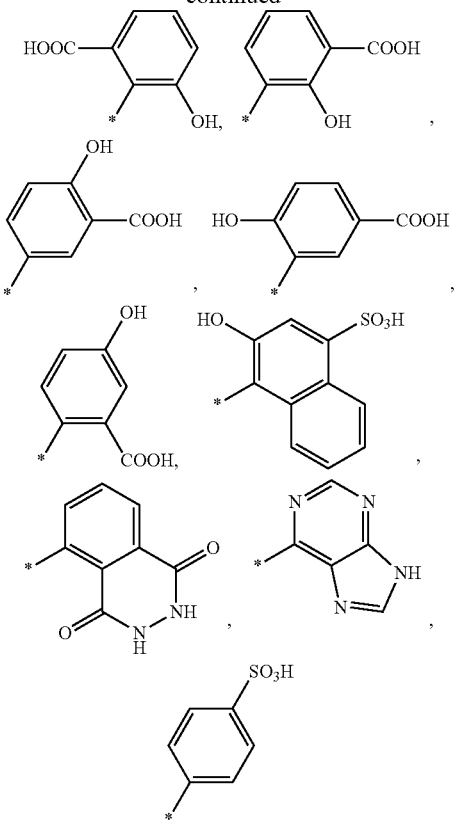

TABLE 2

SMTPs

| Compound No | Molecular weight | R = | Additive organic amino compound |
|---|---|---|---|
| SMTP-18 | 477.6 | (structure: *-C6H4-OH) | p-aminophenol |
| SMTP-19 | 505.6 | (structure: *-C6H4-COOH) | p-aminobenzoic acid |

TABLE 2-continued

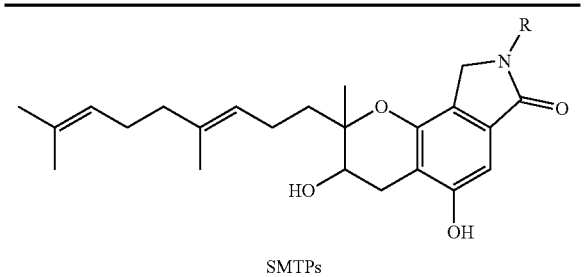

SMTPs

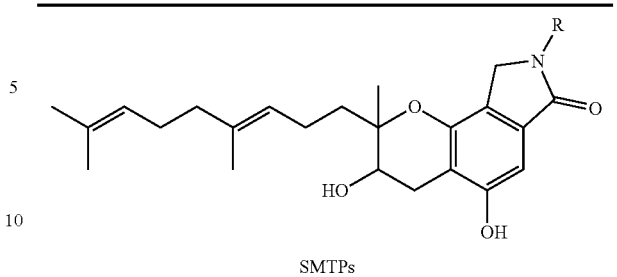

SMTPs

| Compound No | Molecular weight | R = | Additive organic amino compound |
|---|---|---|---|
| SMTP-20 | 505.6 | *-C₆H₄-COOH (meta) | m-aminobenzoic acid |
| SMTP-21 | 505.6 | *-C₆H₄-COOH (ortho) | o-aminobenzoic acid |
| SMTP-22 | 521.6 | *-C₆H₃(OH)-COOH | 4-aminosalicylic acid |
| SMTP-23 | 521.6 | *-C₆H₃(OH)-COOH | 4-amino-3-hydroxybenzoic acid |
| SMTP-24 | 521.6 | *-C₆H₃(OH)-COOH | 3-hydroxyanthranilic acid |
| SMTP-25 | 521.6 | *-C₆H₃(OH)-COOH | 3-aminosalicyclic acid |
| SMTP-26 | 521.6 | *-C₆H₃(OH)-COOH | 5-aminosalicyclic acid |
| SMTP-27 | 521.6 | *-C₆H₃(OH)-COOH | 3-amino-4-hydroxybenzoic acid |
| SMTP-28 | 521.6 | *-C₆H₃(OH)-COOH | 5-hydroxyanthranilic acid |
| SMTP-32 | 503.6 | purine (adenine) | adenine or adenosine |
| SMTP-36 | 545.3 | phthalazine-1,4-dione | 5-amino-2,3-dihydro-1,4-phtalazinedione |
| SMTP-37 | 607.7 | HO-naphthyl-SO₃H | 1-amino-2-naphtol-4-sulfonic acid |
| SMTP-42 | 541.7 | *-C₆H₄-SO₃H | p-sulfanilic acid |

The compounds shown in Table 2 can be used favorably as the compound represented by Formula (I) used in the present disclosure.

Hereinbelow, the compound represented by Formula (II) in which $R^1$ is (C) above is described.

The (C) is an aromatic amino acid residue represented by the following Formula (II-1), wherein $R^3$ is a substituent that may or may not be present, and if present, represents at least one of a hydroxy group, a carboxy group, or an alkyl group having from 1 to 5 carbon atoms, n represents an integer of 0 or 1, m represents an integer from 0 to 5, and * represents a bonding site. The alkyl group may further have a substituent, and examples of the substituent include a hydroxy group, an alkenyl group, an amino group, a carboxy group, and a sulfhydryl group.

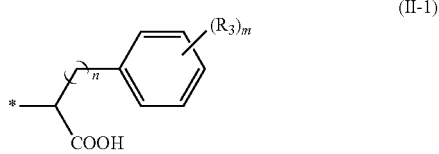

(II-1)

Examples of the aromatic amino acid residue represented by Formula (II-1) include the groups represented by the following structural formulae. * represents a bonding site to the nitrogen atom (the nitrogen atom bonded to $R^1$) of the nitrogen-containing five-membered ring in Formula (II).

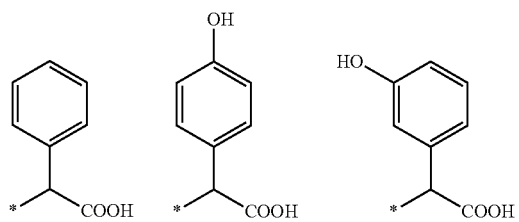 [SMILES: *C(C(=O)O)c1ccccc1 ; *C(C(=O)O)c1ccc(O)cc1 ; *C(C(=O)O)c1cccc(O)c1]

Specific examples of the compound represented by Formula (II) in which $R^1$ is the above (C) include compounds shown in the following Table 3. In the table, * represents a bonding site to the nitrogen atom (the nitrogen atom bonded to R) of the nitrogen-containing five-membered ring in the structural formula shown in the upper column of the table.

TABLE 3

| Compound No | Molecular weight | R = | Additive organic amino compound |
|---|---|---|---|
| SMTP-43 | 519.6 | (phenyl CH-COOH) | L-phenylglycine |
| SMTP-43D | 519.6 | (phenyl CH-COOH) | D-phenylglycine |
| SMTP-44 | 535.6 | (4-OH-phenyl CH-COOH) | L-4-hydroxy-phenylglycine |
| SMTP-44D | 535.6 | (4-OH-phenyl CH-COOH) | D-4-hydroxy-phenylglycine |
| SMTP-45-I | 535.6 | (3-OH-phenyl CH-COOH) | DL-3-hydroxy-phenylglycine |
| SMTP-45-II | 535.6 | (3-OH-phenyl CH-COOH) | DL-3-hydroxy-phenylglycine |

The compounds shown in Table 3 can be used favorably as the compound represented by Formula (I) used in the present disclosure.

Hereinbelow, the compound represented by Formula (II) in which $R^1$ is (D) above is described.

The (D) is a substituent represented by -$L^1$-$L^2$-$R^4$, wherein $L^1$ represents a linking group that is an alkylene group having from 1 to 4 carbon atoms and containing a carboxy group, $L^2$ represents a linking group represented by —NH—C(=O)— or —NH—C(=S)—NH—, and $R^4$ represents a 9-fluorenylalkyloxy group that contains an alkyloxy group having from 1 to 3 carbon atoms, or a polyheterocyclic group represented by the following Formula (II-2). In the following formula, * represents a bonding site to the nitrogen atom (the nitrogen atom bonded to $R^1$) of the nitrogen-containing five-membered ring in Formula (II).

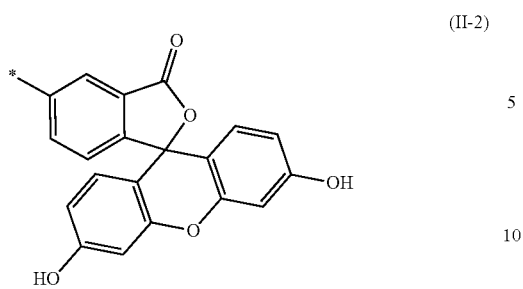

(II-2)

Specific examples of the compound represented by Formula (II) in which $R^1$ is the above (D) include compounds shown in the following Table 4. In the table, * represents a bonding site to the nitrogen atom (the nitrogen atom bonded to R) of the nitrogen-containing five-membered ring in the structural formula shown in the upper column of the table.

TABLE 4

| Compound No | Molecular weight | R = | Additive organic amino compound |
|---|---|---|---|
| SMTP-46 | 722.9 | | Nα-Fmoc-L-ornithine |
| SMTP-47 | 722.9 | | Nδ-Fmoc-L-ornithine |
| SMTP-48 | 890.0 | | Nδ-FITC-L-ornithine |

TABLE 4-continued

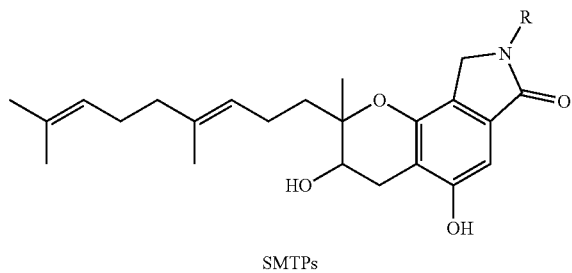

SMTPs

| Compound No | Molecular weight | R = | Additive organic amino compound |
|---|---|---|---|
| SMTP-49 | 890.0 | | Nα-FITC-L-ornithine |

The compounds shown in Table 4 can be used favorably as the compound represented by Formula (I) used in the present disclosure.

Compound Represented by Formula (III)

One of the specific examples of the compound represented by Formula (I) used in the present disclosure is a compound represented by the following Formula (III).

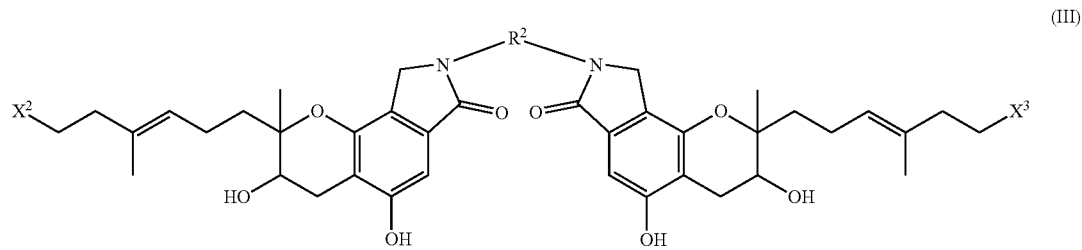

In Formula (III), each of $X^2$ and $X^3$ is independently —CHY—C(CH$_3$)$_2$Z, wherein each of Y and Z is independently —H or —OH, or Y and Z together form a single bond. $R^2$ represents a residue obtained by removing two amino groups from an amino compound selected from the group consisting of: a natural amino acid containing two amino groups; a D-isoform of a natural amino acid containing two amino groups; a compound in which at least one carboxy group of a natural amino acid containing two amino groups or a D-isoform of a natural amino acid containing two amino groups is substituted with a hydrogen atom, a hydroxy group, or a hydroxymethyl group; a compound represented by H$_2$N—CH(COOH)—(CH$_2$)$_n$—NH$_2$ (wherein n is an integer from 0 to 9); and a compound represented by H$_2$N—CH(COOH)—(CH$_2$)$_m$—S$_p$—(CH$_2$)$_q$—CH(COOH)—NH$_2$ (wherein each of m, p, and q is independently an integer from 0 to 9).

n is an integer from 0 to 9, preferably an integer from 0 to 6, more preferably an integer from 1 to 5, and still more preferably an integer from 1 to 4.

m is an integer from 0 to 9, preferably an integer from 0 to 4, more preferably an integer from 1 to 3, and still more preferably 1 or 2.

p is an integer from 0 to 9, preferably an integer from 0 to 4, more preferably an integer from 1 to 3, and still more preferably 1 or 2.

q is an integer from 0 to 9, preferably an integer from 0 to 4, more preferably an integer from 1 to 3, and still more preferably 1 or 2.

When p is 0, m+q is preferably an integer from 0 to 9, more preferably an integer from 0 to 6, still more preferably an integer from 1 to 5, and even more preferably an integer from 1 to 4.

Examples of the natural amino acid containing two amino groups include α-amino acids such as hydroxylysine, citrulline, cystine, homocystine, diaminopimelic acid, diaminopropionic acid, lysine, and ornithine.

Examples of the compound in which at least one carboxy group of a natural amino acid containing two amino groups or a D-isoform of a natural amino acid containing two amino groups is substituted with a hydrogen atom, a hydroxy group, or a hydroxymethyl group include $H_2N-(CH_2)_k-NH_2$ (wherein k is an integer from 1 to 10, preferably an integer from 1 to 6, and more preferably an integer from 1 to 4).

Examples of the compound represented by Formula (III) include compounds shown in the following Table 5. In the table, * represents a bonding site to the nitrogen atom (the nitrogen atom bonded to R) of the nitrogen-containing five-membered ring in the structural formula shown in the upper column of the table.

TABLE 5

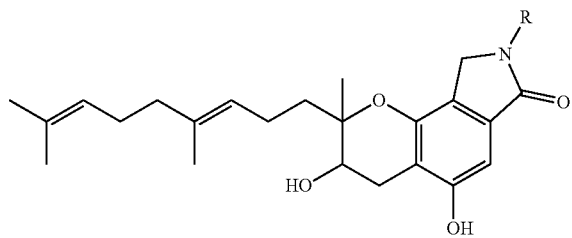 [SMILES: CC(C)=CCC/C(C)=C/CCC1(C)Oc2c(c(O)cc3c2CNC3=O)CC1O]

SMTPs

| Compound No | Molecular weight | R = | Additive organic amino compound |
|---|---|---|---|
| SMTP-7 | 869.1 | | L-ornithine |
| SMTP-7D | 869.1 | | D-ornithine |
| SMTP-8 | 883.1 | | L-lysine |
| SMTP-8D | 883.1 | | D-lysine |

TABLE 5-continued

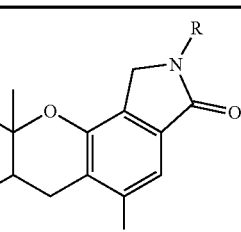

SMTPs

| Compound No | Molecular weight | R = | Additive organic amino compound |
|---|---|---|---|
| SMTP-9 | 977.2 | 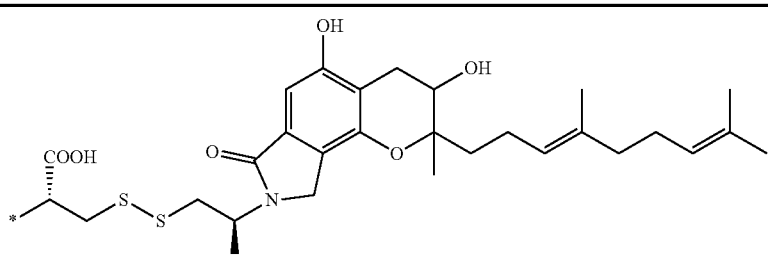 | L-cystine |
| SMTP-29 | 839.1 | | DL-2,3-diaminopropionic acid |
| SMTP-31 | 925.2 | 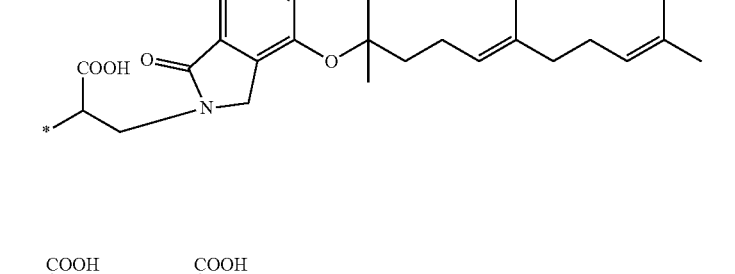 | DL-2,6-diaminopimelic acid |

The compounds shown in Table 5 can be used favorably as the compound represented by Formula (I) used in the present disclosure.

Specific examples of the compound represented by Formula (I) include, in addition to the compound represented by Formula (II) or Formula (III), compounds shown in the following Tables 6 to 8. In Table 7, * represents a bonding site to the nitrogen atom (the nitrogen atom bonded to $R^b$ or $R^c$) of the nitrogen-containing five-membered ring in the structural formula (Ib) or (Ic) shown in the upper column of the table. In Table 8, * represents a bonding site to the nitrogen atom (the nitrogen atom bonded to $R^d$ or $R^e$) of the nitrogen-containing five-membered ring in the structural formula (Id) or (Ie) shown in the upper column of the table.

TABLE 6

SMTP-0

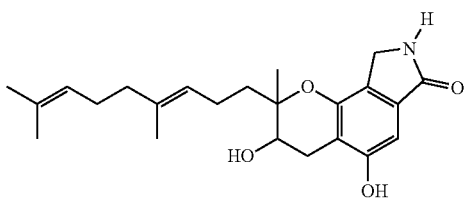

TABLE 6-continued
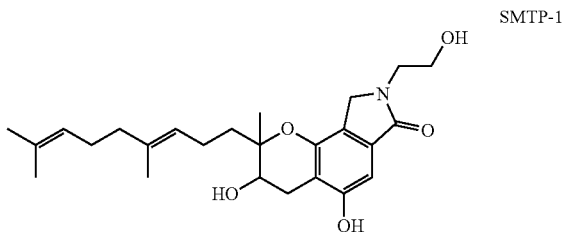
SMTP-1
| Compound No | Molecular weight | Additive organic amino compound |
|---|---|---|
| SMTP-0 | 385.5 | Ammonium chloride |
| SMTP-1 | 429.6 | 2-aminoethanol |
TABLE 7
(Ib)
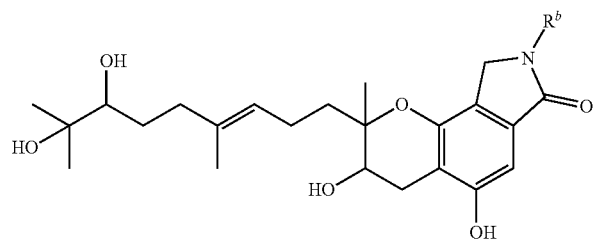
| Compound No | $R^b$ |
|---|---|
| SMTP-0e | *—H |
| SMTP-2 | 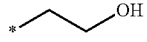 |
| SMTP-4e | 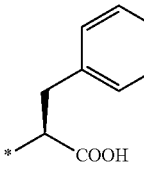 |
| SMTP-7e | 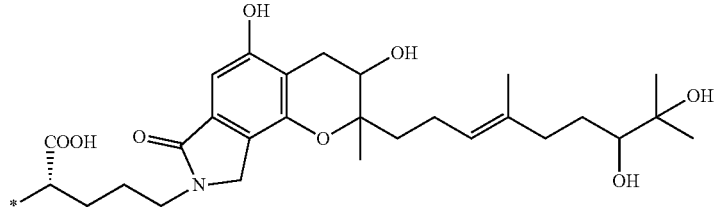 [SMILES: *[C@@H](CCCN1Cc2c(cc(O)c3c2OC(C)(CC/C=C(\C)CCC(O)C(C)(C)O)C(O)C3)C1=O)C(=O)O] |
| SMTP-21e | 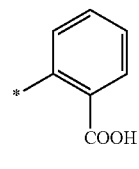 |
| SMTP-27e | 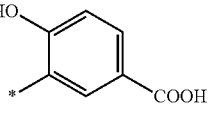 |

TABLE 7-continued
SMTP-36e
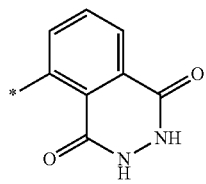
SMTP-43e
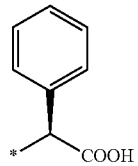
(Ic)
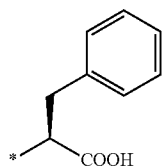
| Compound No | $R^c$ |
|---|---|
| SMTP-0a | *—H |
SMTP-4a
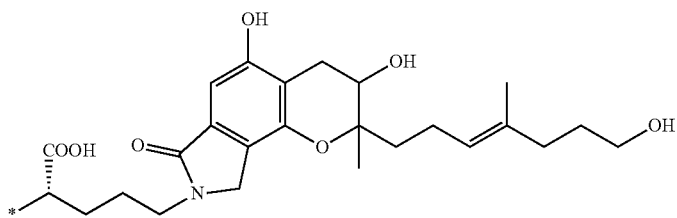 [SMILES: *[C@@H](CCCN1Cc2c(cc(O)c3c2OC(C)(CC/C=C(\C)CCCO)C(O)C3)C1=O)C(=O)O]
SMTP-7a
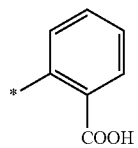
SMTP-21a
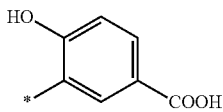
SMTP-27a
SMTP-36a
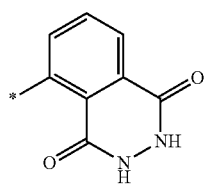

TABLE 7-continued
| SMTP-43a | 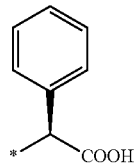 |
|---|---|
TABLE 8
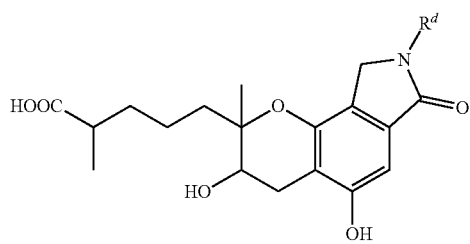
(Id)
| Compound No | $R^d$ |
|---|---|
| SMTP-0b | *—H |
| SMTP-4b | 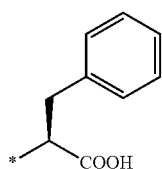 [SMILES: *[C@@H](Cc1ccccc1)C(=O)O] |
| SMTP-7b | 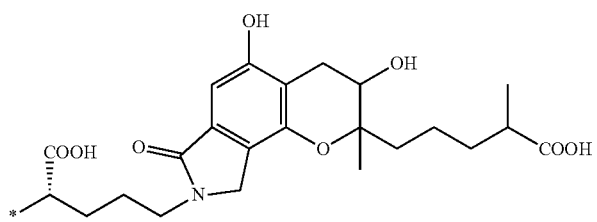 [SMILES: *[C@@H](CCCN1Cc2c(cc(O)c3c2OC(C)(CCCC(C)C(=O)O)C(O)C3)C1=O)C(=O)O] |
| SMTP-21b | 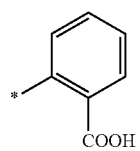 |
| SMTP-27b | 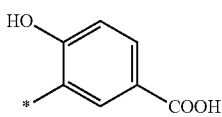 |
| SMTP-36b | 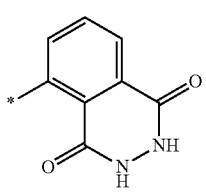 [SMILES: *c1cccc2c(=O)[nH][nH]c(=O)c12] |

TABLE 8-continued
| SMTP-43b | 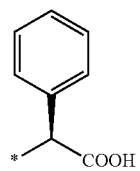 |
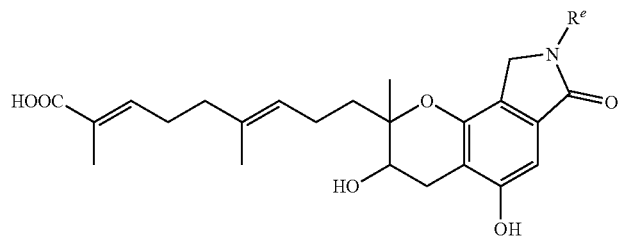
(Ie)
| Compound No | $R^e$ |
|---|---|
| SMTP-0c | *—H |
| SMTP-4c | 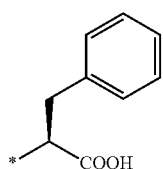 [SMILES: *[C@@H](Cc1ccccc1)C(=O)O] |
| SMTP-7c | 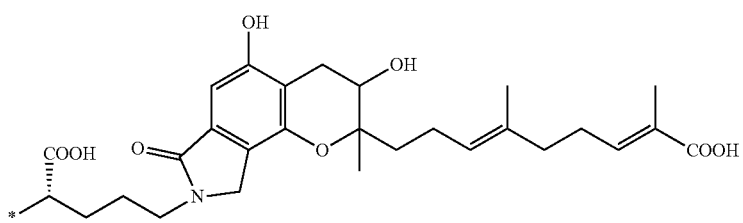 [SMILES: *[C@@H](CCCN1Cc2c(cc(O)c3c2OC(C)(CC/C=C(\C)CC/C=C(\C)C(=O)O)C(O)C3)C1=O)C(=O)O] |
| SMTP-21c | 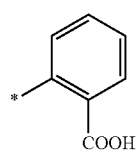 |
| SMTP-27c | 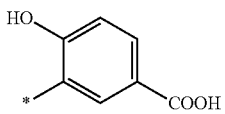 |
| SMTP-36c | 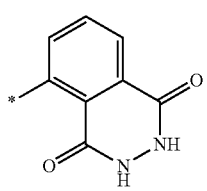 [SMILES: *c1cccc2c(=O)[nH][nH]c(=O)c12] |
| SMTP-43c | 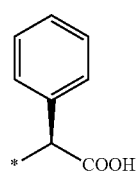 |

The compounds shown in Tabled 6 to 8 can be used favorably as the compound represented by Formula (I) used in the present disclosure.

Among the above compounds, the compound represented by Formula (I) is preferably SMTP-0, SMTP-1, SMTP-4, SMTP-5D, SMTP-6, SMTP-7, SMTP-8, SMTP-11 to SMTP-14, SMTP-18 to SMTP-29, SMTP-36, SMTP-37, SMTP-42, SMTP-43, SMTP-43D, SMTP-44, SMTP-44D, SMTP-46, or SMTP-47, more preferably SMTP-7, SMTP-19, SMTP-22, SMTP-43, or SMTP-44D, and still more preferably SMTP-7. These compounds may be used singly, or in any combination of two or more kinds thereof.

The compound represented by Formula (I) used in the present disclosure may be in a free form, in a form of a pharmaceutically acceptable salt or an ester, or in a form of a solvate. An inorganic acid or an organic acid such as hydrochloric acid, hydrobromic acid, sulfuric acid, nitric acid, phosphoric acid, citric acid, formic acid, fumaric acid, malic acid, acetic acid, succinic acid, tartaric acid, methanesulfonic acid, or p-toluenesulfonic acid is preferably used to form the pharmaceutically acceptable salt of the compound represented by Formula (I) used in the present disclosure. Further, a compound containing an alkali metal or an alkaline-earth metal such as sodium, potassium, calcium, or magnesium, a basic amine, or a basic amino acid is preferably used to form the pharmaceutically acceptable salt of the compound represented by Formula (I) used in the present disclosure. Further, an alcohol or a carboxylic acid having from 1 to 10 carbon atoms, preferably methyl alcohol, ethyl alcohol, acetic acid, or propionic acid is preferably used to form the pharmaceutically acceptable ester of the compound represented by Formula (I) used in the present disclosure. Further, water is preferably used to form the pharmaceutically acceptable solvate of the compound represented by Formula (I) used in the present disclosure.

The specific examples of the compound represented by Formula (I), such as SMTP-7, described above also include those in a salt, ester, or solvate form.

(Applications of Compound Represented by Formula (I))

Examples of the applications of the compound represented by Formula (I) include use in treating or preventing cerebral hemorrhage. In other words, according to the present disclosure, the compound represented by Formula (I) or a pharmaceutically acceptable salt, ester, or solvate thereof for use in treating or preventing cerebral hemorrhage is also provided. Details of usage and the like in such cases are the same as those in the method of treating or preventing cerebral hemorrhage described below, and preferable aspects are also the same. The compound represented by Formula (I) can be used, for example, in a method of treating or preventing cerebral hemorrhage as described below. The compound represented by Formula (I) produces an effect not only in the reduction or elimination of a hematoma caused by cerebral hemorrhage, but also in the reduction or elimination of an edema. Since a hematoma and edema are different phenomena, the fact that the compound represented by Formula (I) produces an effect on both hematoma and edema is surprisingly advantageous.

According to the present disclosure, use of the compound represented by Formula (I) or a pharmaceutically acceptable salt, ester, or solvate thereof, for the manufacture of a medicament for treating or preventing cerebral hemorrhage is also provided.

In one embodiment, the compound represented by Formula (I) or a pharmaceutically acceptable salt, ester, or solvate thereof is administered to a subject for treating or preventing cerebral hemorrhage that does not involve cerebral infarction (in other words, cerebral hemorrhage that does not associated with cerebral infarction).

(Method of Treating or Preventing Cerebral Hemorrhage)

The method of treating or preventing cerebral hemorrhage according to the present disclosure is a method of treating or preventing cerebral hemorrhage in a subject, the method including administering the compound represented by Formula (I) or a pharmaceutically acceptable salt, ester, or solvate thereof, in an amount effective for treating or preventing cerebral hemorrhage to the subject suffering from cerebral hemorrhage or at risk of developing cerebral hemorrhage.

The method of treating or preventing cerebral hemorrhage according to the present disclosure can produce an effect, such as inhibiting aggravation of cerebral hemorrhage, reducing or alleviating symptoms of cerebral hemorrhage, or inhibiting the onset of, reducing the risk of, or delaying the onset of cerebral hemorrhage. More specifically, in the brain, an effect, such as reduction or disappearance of a hematoma once generated, reduction or disappearance of an edema once generated, or recovery of brain function, can be obtained. Here, "subject suffering from cerebral hemorrhage" includes not only a subject who has developed cerebral hemorrhage, but also a subject whose cerebral hemorrhage has been arrested but who still suffers from some damage (for example, presence of a hematoma, presence of an edema, or damage to brain function) due to the cerebral hemorrhage.

In the present disclosure, the term "treatment" may mean an improvement or suppression of a symptom, and includes suppression of aggravation or reduction or alleviation of a symptom.

In the present disclosure, the term "prevention" means inhibition of onset, reduction of risk of onset, or delay of onset.

The compound represented by Formula (I) (including a pharmaceutically acceptable salt, ester, or solvate thereof; the same applies hereinafter) can be used for treating a subject found to have a symptom of cerebral hemorrhage (including a subject whose cerebral hemorrhage has been arrested but who suffers from some damage due to cerebral hemorrhage as described above), or can be used for preventing cerebral hemorrhage in a subject at risk of developing cerebral hemorrhage (in particular, a subject for whom development of cerebral hemorrhage is predictable) but who has not developed cerebral hemorrhage.

The compound represented by Formula (I) can be used to eliminate a symptom caused by cerebral hemorrhage, inhibit progression of a symptom, or alleviate a symptom. It is noted, however, that these effects may be compounded depending on the time of use or a symptom at the time of use, and are not to be construed as limiting.

Examples of the case in which a symptom due to cerebral hemorrhage has been found, or the case in which occurrence of a symptom due to cerebral hemorrhage has been predicted, include a period of time during or after treatment for intracerebral hemorrhage, subarachnoid hemorrhage, and the like. Since a thrombolytic agent such as alteplase or urokinase has a common side effect of bleeding, examples of the above cases also include a period of time after administration of such a thrombolytic agent, which is a period when cerebral hemorrhage due to the administration of the thrombolytic agent is predictable. In such a period of time, the compound can also be used prophylactically. The risk of developing cerebral hemorrhage can also be determined by brain imaging, a physiological test such as a blood test, or the like. The compound represented by Formula (I) may be administered prophylactically to a subject who has been determined to have such a risk, even before actual development of cerebral hemorrhage.

Cerebral hemorrhage is a condition in which bleeding occurs in the brain by rupture of a blood vessel in the brain. The blood overflowing from the blood vessel forms a hematoma, and also forms an edema in a region around the hemorrhage. The hematoma and the edema cause compression of normal brain tissues, resulting in impairment of brain functions. The compound represented by Formula (I) produces an effect not only in the reduction or elimination of a hematoma, but also in the reduction or elimination of an edema. Since hematoma and edema are different phenomena, the fact that the compound represented by Formula (I) produces an effect on both hematoma and edema is surprisingly advantageous.

Cerebral hemorrhage can be broadly classified into intracerebral hemorrhage and subarachnoid hemorrhage depending on the site of bleeding. Subarachnoid hemorrhage is basically caused by rupture of a cerebral aneurysm. Intracerebral hemorrhage refers to hemorrhage in a variety of areas of the brain, including putaminal hemorrhage, thalamic hemorrhage, subcortical hemorrhage, cerebellar hemorrhage, and pontine hemorrhage. The compound represented by Formula (I) is effective against both of these intracerebral hemorrhage and subarachnoid hemorrhage.

Conventionally, subarachnoid hemorrhage has been treated surgically with neck clipping or intravascular operation, and intracerebral hemorrhage has been treated surgically with surgery to remove hematoma. It is surprising that the compound represented by Formula (I) can treat or prevent cerebral hemorrhage by medication.

Cerebral hemorrhage is basically a different disease from cerebral infarction. In one embodiment, the compound represented by Formula (I) is administered to a subject for treating or preventing cerebral hemorrhage that does not involve cerebral infarction (in other words, cerebral hemorrhage that does not associated with cerebral infarction). The treatment or prevention method according to the present disclosure is applicable to both intracerebral hemorrhage and subarachnoid cerebral hemorrhage.

Depending on a kind of a compound used in combination and the seriousness of cerebral hemorrhage, the compound represented by Formula (I) is administered preferably at 0.001 to 100 mg/kg, and more preferably at 0.01 to 30 mg/kg, as a single effective dose (in a total amount of the compound represented by Formula (I)) for an adult. The number of administrations of the compound represented by Formula (I) is not particularly limited, and the compound may be used in a single dose, multiple doses, or a continuous dose. The interval and duration of administration can be selected by a skilled person according to clinical findings, image findings, hematological findings, a comorbidity, a preexisting condition, or the like.

In a case in which the compound represented by Formula (I) is used by multiple doses, an embodiment in which the compound is continuously administered for 1 hour to 24 hours per day is preferable, from the viewpoint of a sustainable contact of an affected part with the compound represented by Formula (I).

The method of administration is not particularly limited, and can be selected from a variety of administration routes such as intravenous administration, intra-arterial administration, intraperitoneal administration, subcutaneous administration, intramuscular administration, oral administration, or intracerebral administration.

Intracerebral administration can be performed, for example, by using a microsyringe equipped with a microneedle, inserting the microneedle into a guide cannula implanted in a brain, and injecting a drug solution into a predetermined region of the brain. Intracerebral administration is preferable from the viewpoint of reducing a dosage.

The drug according to the present disclosure can be used without limitation only to the use for humans. Examples of another subject include non-human animals such as domestic animals (such as cattle, horses, and sheep) and companion animals (such as dogs, cats, and monkeys).

<Use of Other Drug in Combination>

The compound represented by Formula (I) may be used singly or with at least one other drug (such as an antihypertensive agent).

<Pharmaceutical Composition>

The compound represented by Formula (I) may be used in a pharmaceutical composition. In other words, a pharmaceutical composition including the compound represented by Formula (I) and at least one of a pharmaceutically acceptable carrier or an additive for formulation is provided. The use, dosage, administration method, and the like of the pharmaceutical composition are the same as those of the drug according to the present disclosure, and can be used, for example, in the method of treating or preventing cerebral hemorrhage according to the present disclosure. In other words, the following methods can be provided:

A method of treating a cerebral hemorrhage in a subject, the method including administering the pharmaceutical composition according to the present disclosure, in an amount effective for treating the cerebral hemorrhage, to the subject suffering from the cerebral hemorrhage; and A method of preventing a cerebral hemorrhage in a subject, the method including administering the pharmaceutical composition according to the present disclosure, in an amount effective for preventing the cerebral hemorrhage, to a subject at risk of developing the cerebral hemorrhage.

The types of a carrier and a formulation additive optionally included in the pharmaceutical composition are not particularly limited. The pharmaceutical composition according to the present disclosure can be formulated using the compound represented by Formula (I) according to the present disclosure and a pharmaceutically acceptable solid carrier (such as gelatin or lactose) or liquid carrier (such as water, saline solution, or glucose solution).

EXAMPLES

Hereinbelow, some working examples according to the present disclosure are described, but the working examples according to the present disclosure is not limited thereto. Unless otherwise specified, "%" means a percentage by mass.

<Preparation of SMTP-7>

According to a process described in JP-A No. 2004-224738, SMTP-7 was obtained by purification of a culture obtained by adding L-ornithine as an additive organic amino compound to a culture medium of *Stachybotrys microspora*, strain IFO30018. To the dried solid of SMTP-7 obtained by the purification, 0.3 N (0.3 mol/L) NaOH solution and saline (0.9% NaCl) were added to prepare a 50 mg/mL solution. Thereafter, the solution was adjusted to have a SMTP-7 concentration of 10 mg/mL and weak alkaline pH, using 0.3 N (0.3 mol/L) HCl solution and saline. The resultant was subjected to filter sterilization, divided into small fractions, and cryopreserved at −30° C.

The cryopreserved SMTP-7 was dissolved in saline at a concentration of 2 mg/mL immediately before a test. The resultant was used as a test solution in the following experiment.

Each drug used in the experiment was diluted with saline as needed.

Example 1

Preparation of Rat 9- to 10-week-old male SD rats (body weight: from 250 to 300 g) were maintained under a 12-hour light/dark cycle and a temperature condition of 22° C.±1° C. The rats were kept in plastic cages and had free access to water and food. The number of rats used in each experiment was n=4, unless otherwise specified. The injection solution was saline except for the components described.

After the rat was anesthetized with isoflurane (1.5% isoflurane+66% NO+33% $O_2$), COLLAGENASE from *Clostridium histolyticum* (typeIV, manufactured by Sigma-Aldrich) was injected at the position 3 mm lateral to the midline of the brain from the bregma (in the anterior-posterior direction) and 5 mm dorsal to the stria vascularis at a concentration of 0.25 U/μL for 5 minutes at a rate of 0.2 μL/min using a syringe, the syringe needle was held in that position for 10 minutes, and then slowly withdrawn over another 10 minutes (i.e., 0.5 mm per minute). During the injection, care was taken not to cause backflow. In the following description, the day of the collagenase injection is referred to as day 0. The collagenase injection causes an intracerebral hemorrhage, thereby forming a hematoma.

Twenty-four hours after the collagenase injection (i.e., day 1 after the collagenase injection), a test solution (saline, 2 mg/mL solution of SMTP-7) was injected through the same injection scar as the collagenase injection at a rate of 0.2 μL/min over 10 minutes. A test group that did not receive an injection of a test solution was also included. During the injection, care was taken not to cause backflow. As in the case of the collagenase injection, the syringe needle was held in that position for 10 minutes after the injection, and then slowly withdrawn over another 10 minutes (i.e., 0.5 mm per minute).

Figure 1B:
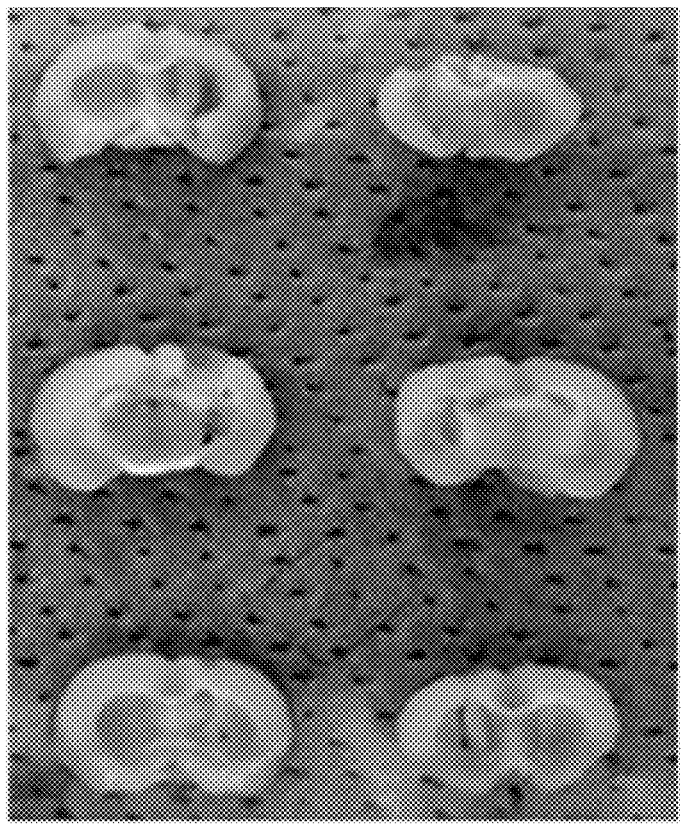
FIG. 1C provides a photograph of a brain section in a study using an animal model of cerebral hemorrhage, FIG. 2 provides a graph illustrating the percentage of hematoma volume with respect to gross brain volume in a study using an animal model of cerebral hemorrhage, FIG. 3A provides a photograph of Evans Blue staining of brain sections in a study using an animal model of cerebral hemorrhage, FIG. 3B provides a photograph of Evans Blue staining of brain sections in a study using an animal model of cerebral hemorrhage, FIG. 3C provides a photograph of Evans Blue staining of brain sections in a study using an animal model of cerebral hemorrhage, FIG. 3D provides a photograph of Evans Blue staining of brain sections in a study using an animal model of cerebral hemorrhage, FIG. 4 provides a graph illustrating the area of a region stained with Evans Blue staining in a gross brain sample in a study using an animal model of cerebral hemorrhage, FIG. 5 provides a graph illustrating the density of Evans Blue staining in a gross brain sample in a study using an animal model of cerebral hemorrhage, FIG. 6 provides MRI images of brains showing hematomas in a study using an animal model of cerebral hemorrhage, FIG. 7 provides a graph illustrating the percentage of hematoma volume in MRI images in a study using an animal model of cerebral hemorrhage, FIG. 8 provides a graph illustrating the time-series variation in the percentage (%) of hematoma volume in MRI images in a study using an animal model of cerebral hemorrhage, FIG. 9 provides MRI images of brains with an edema in a study using an animal model of cerebral hemorrhage.
Figure 1C:
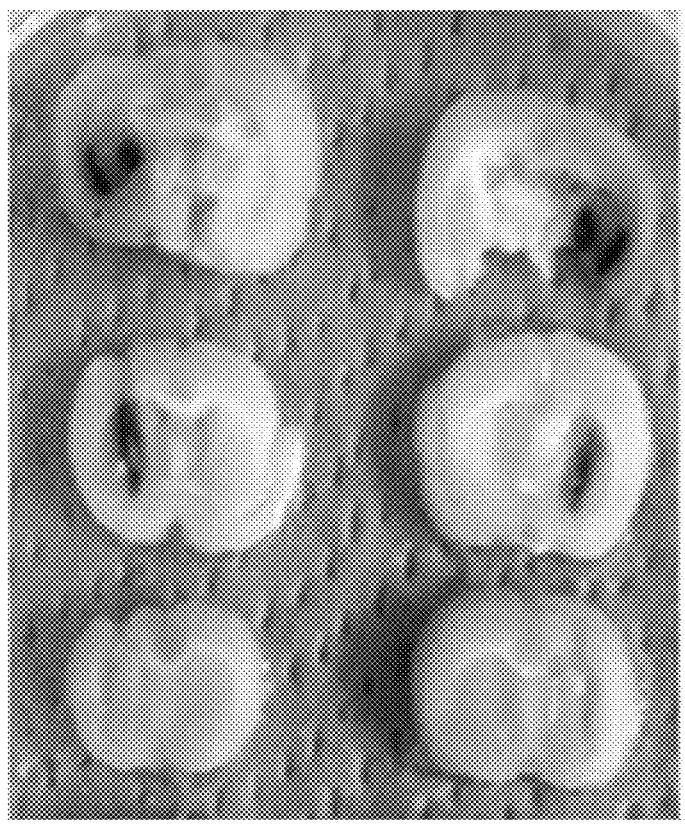

On day 7 after the collagenase injection, the rats were sacrificed, and 3-mm thick sections of the brain were prepared. For fixation during the section preparation, 4% paraformaldehyde in 0.1 M PBS (pH 7.4) was used. Micrographs of the sections are shown in FIGS. 1A to 1C. In FIGS. 1A to 1C, "ICH" represents the section of the individual injected with the collagenase but not with the test solution, "Vehicle" represents the section of the individual injected with the saline instead of the collagenase, and "Treatment" represents the section of the individual injected with the test solution containing SMTP-7. These notations apply to the following Figures as well.

Figure 2:
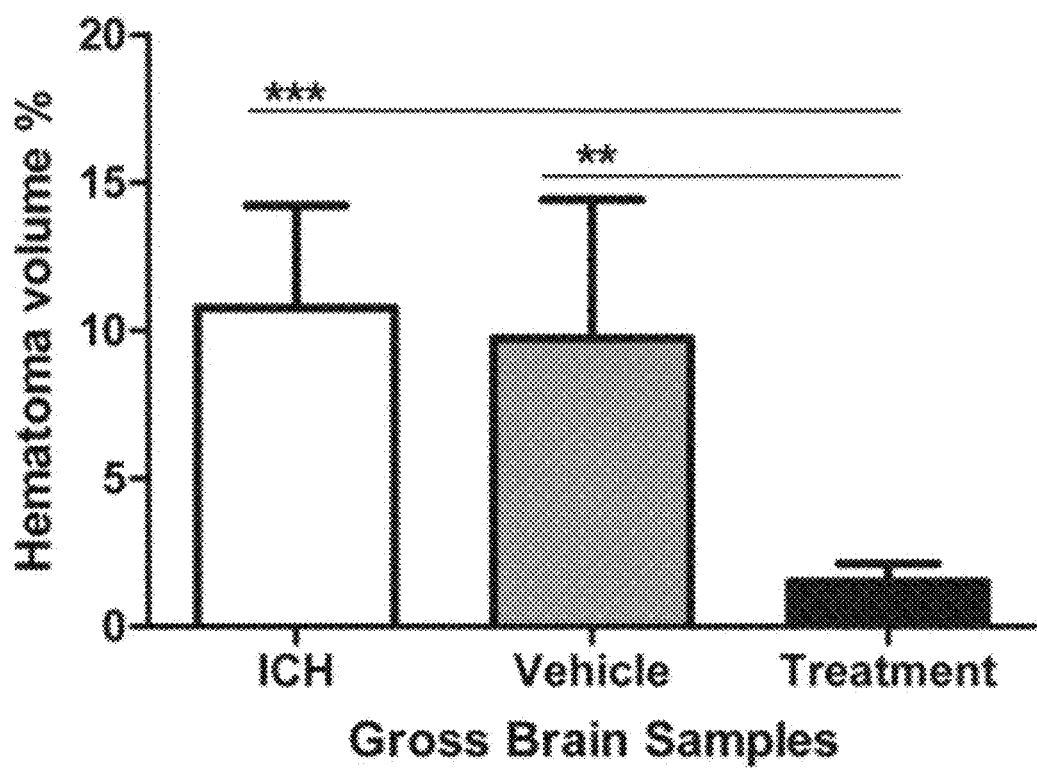

The percentage of the hematoma volume with respect to the gross brain volume was measured using ImageJ. The results are illustrated in FIG. 2. In the graphs of the present disclosure, the vertical axis represents the ratio (expressed as a percentage) of the hematoma volume with respect to the volume of the gross brain sample,  indicates that the p-value by t-test for a significant difference is less than 0.01, and * indicates that the p-value by t-test for a significant difference is less than 0.001 (the meanings of  and * are the same below). The bars in the graphs represent the standard deviation. As illustrated in FIGS. 1A to 1C and FIG. 2, the individual injected with the test solution containing SMTP-7 exhibited a considerable reduction in hematoma size.

Example 2

Figure 3A:
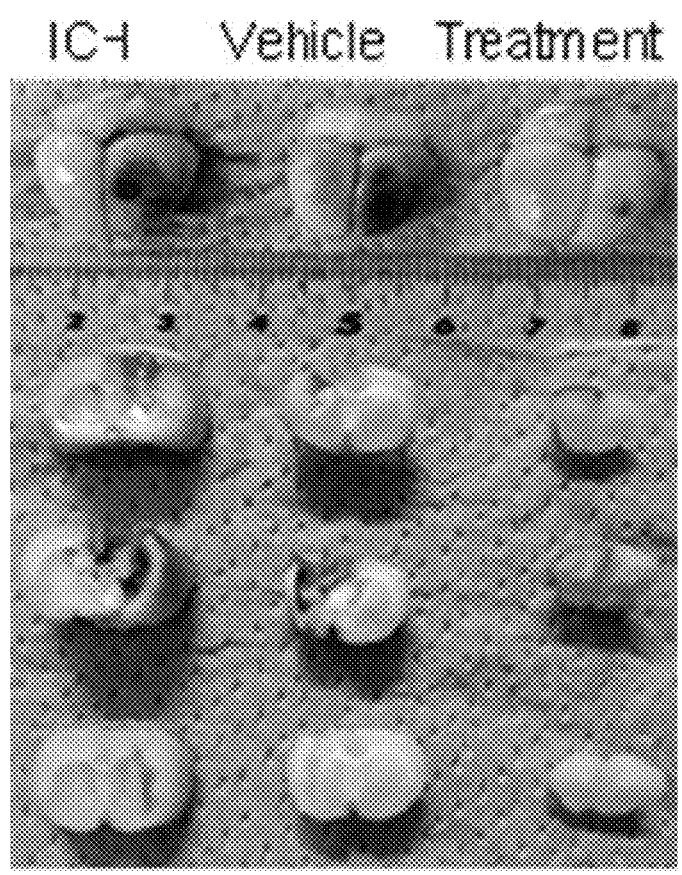
Figure 3B:
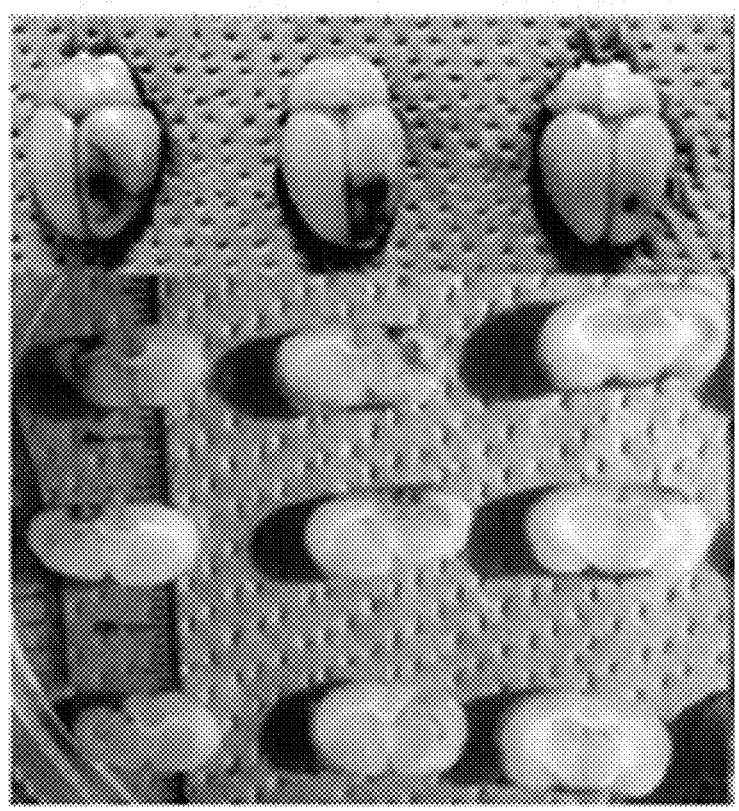
Figure 3C:
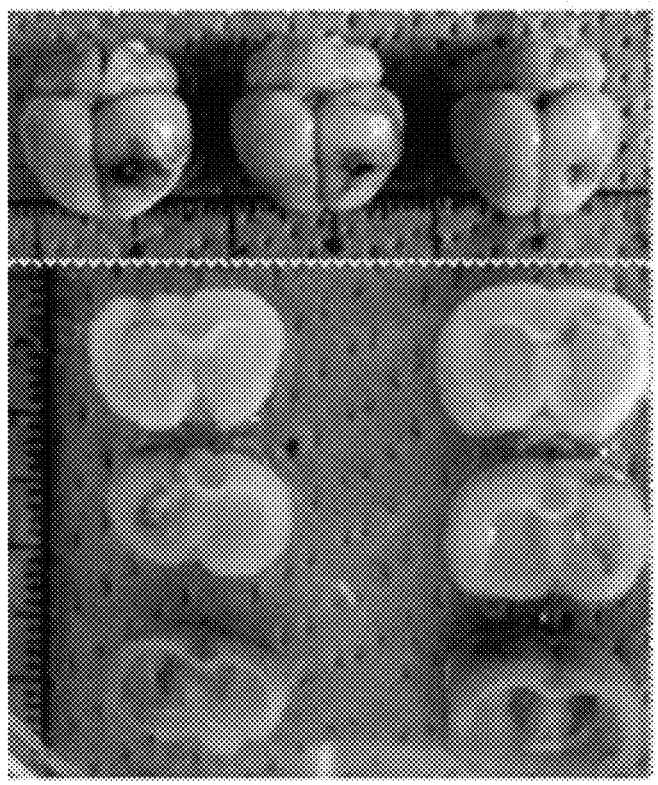
Figure 3D:
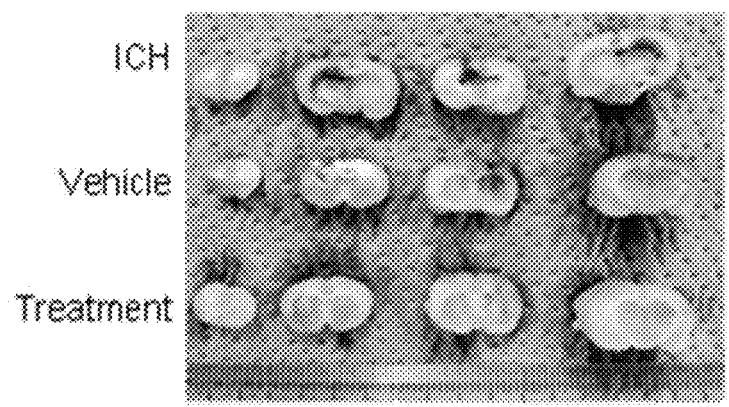
Figure 3D:
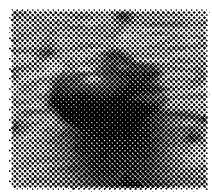
Figure 4:
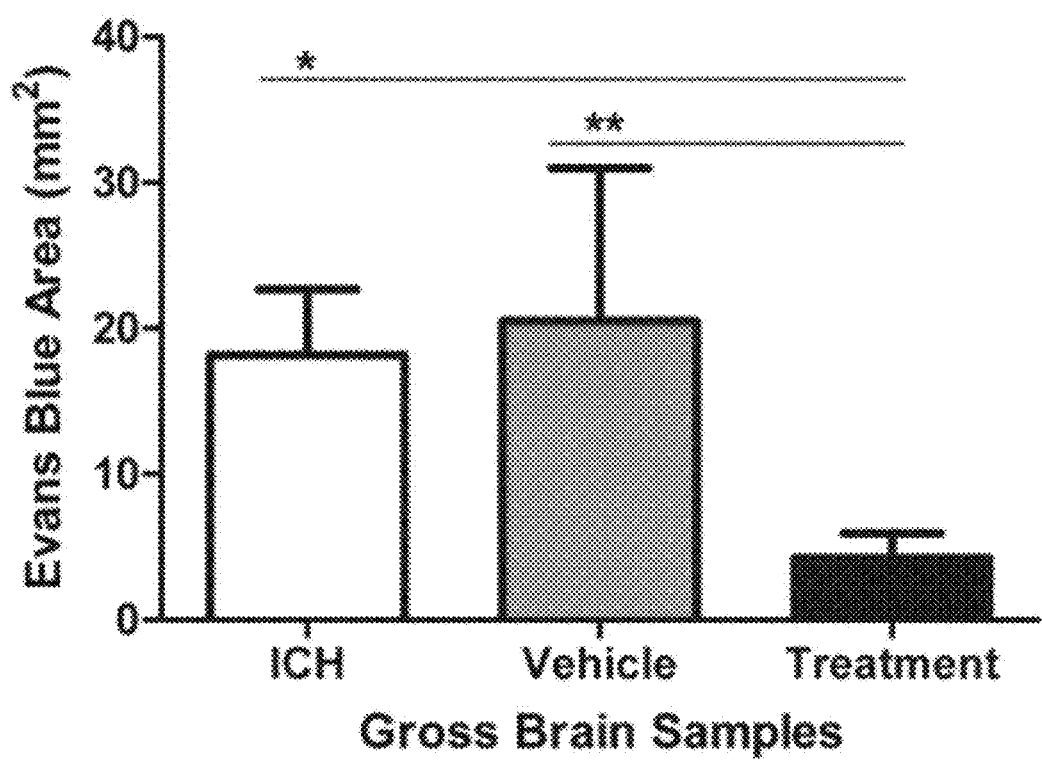
Figure 5:
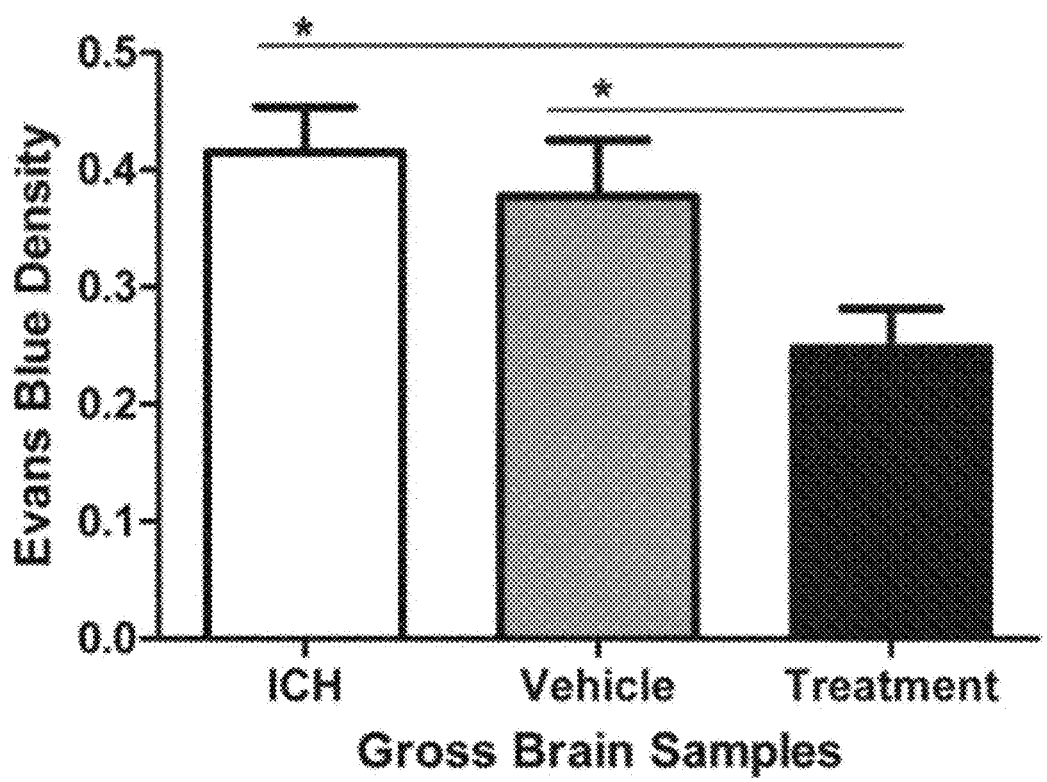

The same experiment as in Example 1 was performed again. However, in Example 2, a saline solution containing 2% Evans Blue was injected into the tail vein at a volume of 4 mL per kg of body weight one hour before sacrifice (day 7). Evans Blue has the property of binding to albumin in the blood, and the hematoma is stained because the blood-brain barrier is disrupted as a result of the collagenase injection. Micrographs of the whole brain and 3-mm thick sections are shown in FIGS. 3A to 3D. The total area ($mm^2$) and staining density of the Evans Blue-stained region determined from the sections using ImageJ are illustrated in FIG. 4 and FIG. 5. FIG. 3D also illustrates the Evans Blue staining of the blood clot. In FIG. 4, the vertical axis represents the area ($mm^2$) of the region stained by Evans Blue staining in the gross brain sample. * indicates that the p-value of t-test for a significant difference is less than 0.05, and ** indicates that the p-value of t-test for a significant difference is less than 0.01 (the meanings of * and ** are the same below). In FIG. 5, the vertical axis represents the density value of Evans Blue expressed as absorbance at 620 nm wavelength. As illustrated in FIGS. 3A to 3D, FIG. 4, and FIG. 5, the individual injected with the test solution containing SMTP-7 exhibited a considerable reduction in hematoma size.

Example 3

Figure 6:
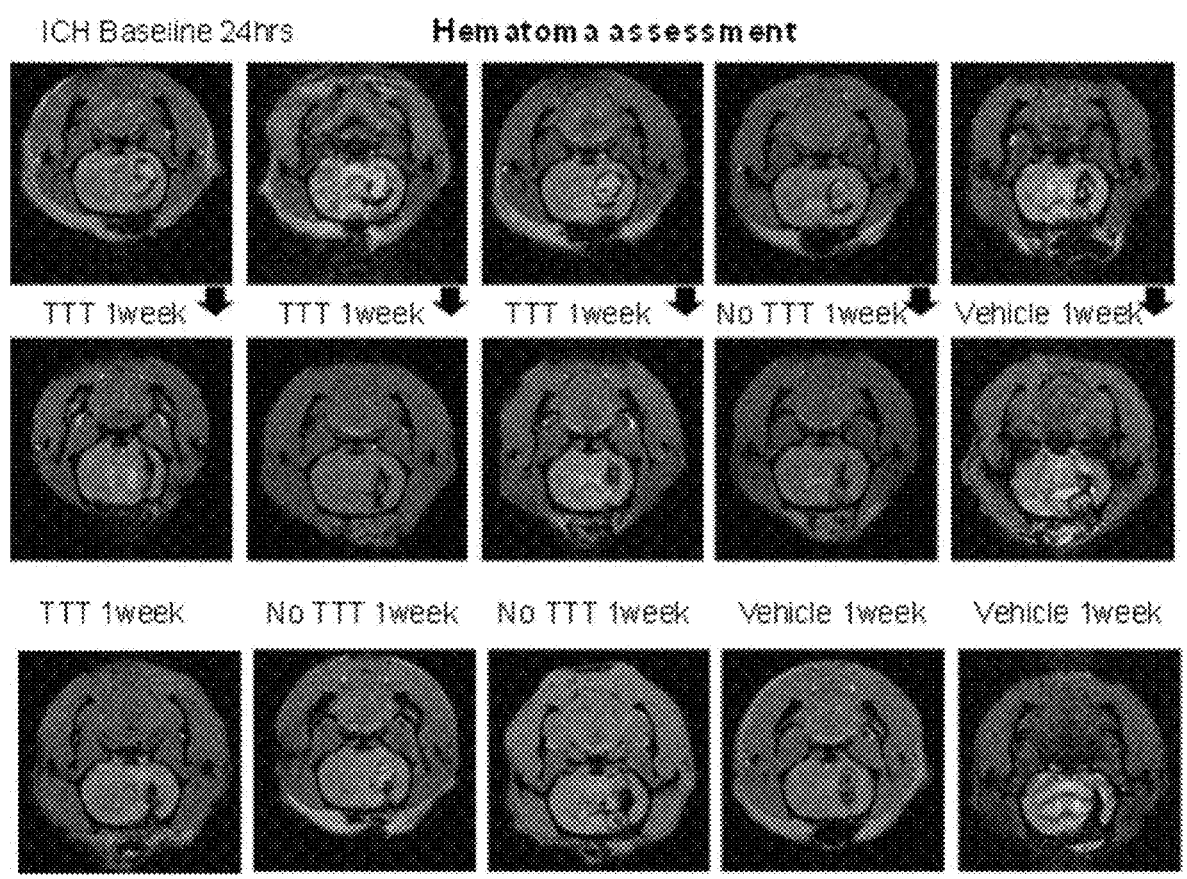
Figure 7:
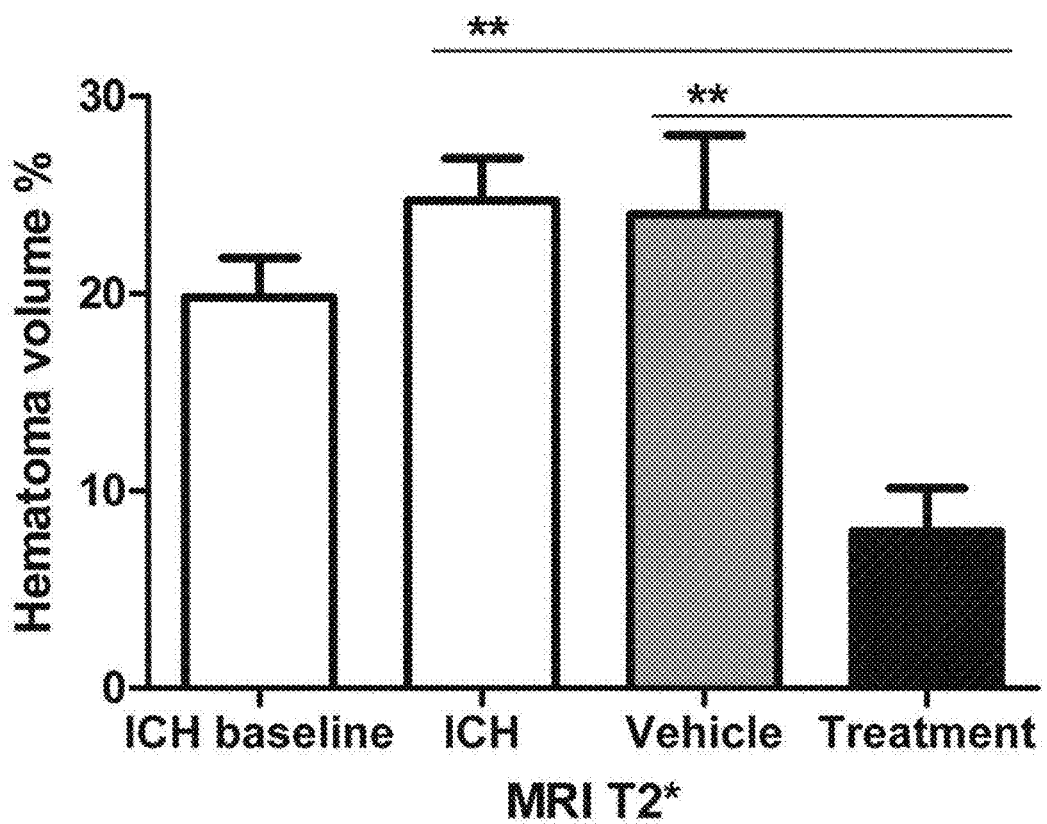
Figure 8:
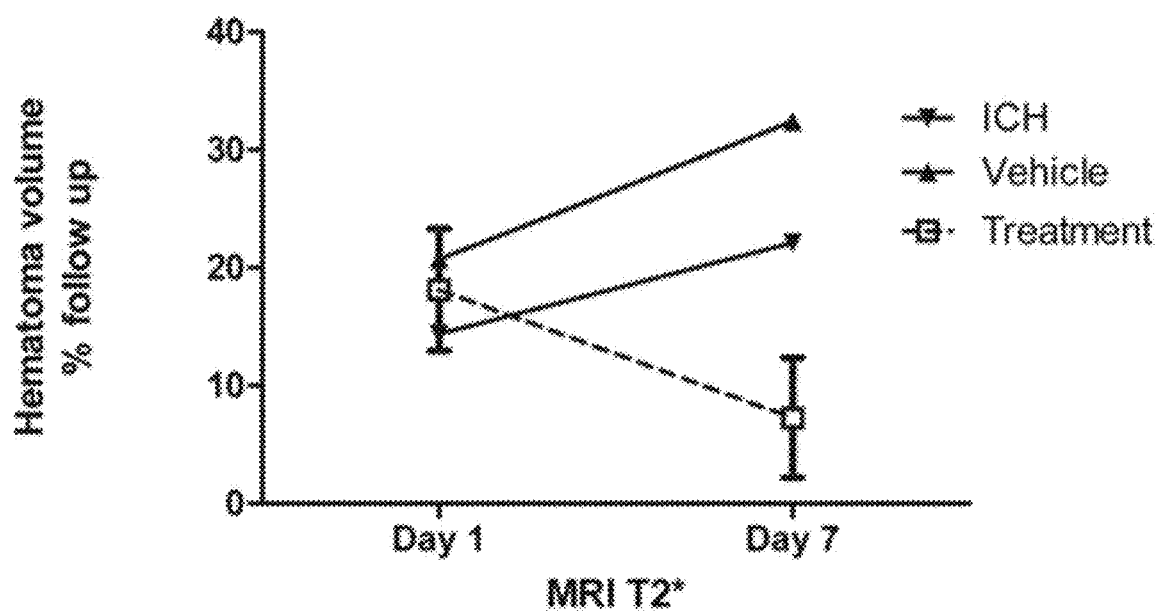
Figure 9:
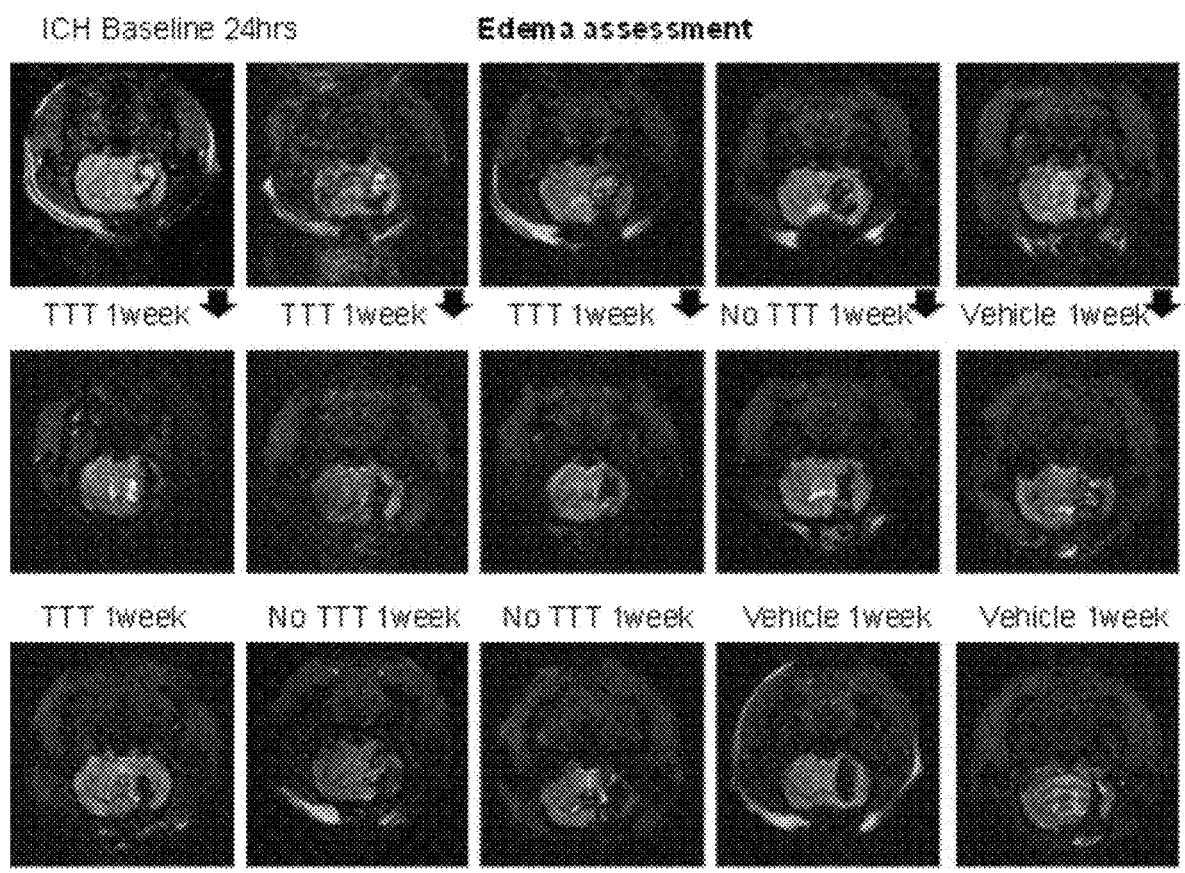
Figure 10:
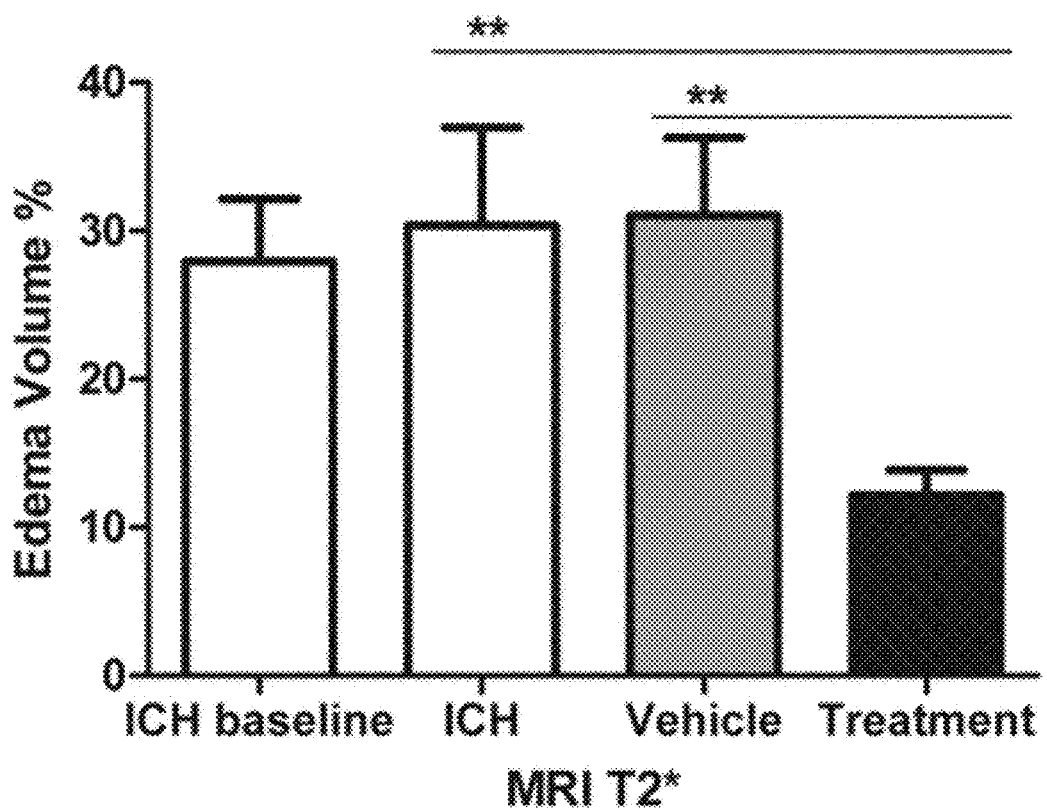
FIG. 10 shows a graph illustrating the percentage of an edema volume in MRI images in a study using an animal model of cerebral hemorrhage.

Injections of the collagenase and the test solution were performed in the same manner as in Example 1, and the brains of rats on days 1 and 7 after the collagenase injection were measured by small animal MRI (PHARMASCAN, manufactured by Bruker BioSpin). Measurement was performed under the following conditions: magnetic field 7T, echo time (TE)=4 ms, repetition time (TR)=800 ms, 256× 256 matrix, slice thickness 0.8 mm, and scan time on average about 5 min 7 sec, and T2-weighted images were obtained. The MRI measurements were performed while the rats were kept in the living state under anesthetization with from 2.5% to 3% isoflurane+NO+$O_2$. The results are shown in FIG. 6. In FIG. 6, "ICH Baseline 24 hrs" refers to the brain image of the rat on day 1 after the collagenase injection, "TTT 1 week" refers to the brain image of the rat on day 7 after the injection of the test solution containing SMTP-7, "No TTT 1 week" refers to the brain image of the rat on day 7 that did not receive an injection of a test solution, and "Vehicle 1 week" refers to the brain image of the rat on day 7 after the injection of the saline instead of the test solution. As shown in FIG. 6, four samples are indicated by "TTT 1 week", three samples are indicated by "No TTT 1 week", and three samples are indicated by "Vehicle 1 week". Based on the Mill measurements, the volume of hematoma was measured using ImageJ. The hematoma volume on day 7 after the collagenase injection is shown in FIG. 7, and the change in hematoma volume from the hematoma volume on day 1 after the collagenase injection is shown in FIG. 8. In FIG. 7, the vertical axis represents the ratio (expressed as a percentage) of hematoma volume in the T2-weighted image in MRI. "ICH Baseline" refers to the rat on day 1 after the collagenase injection, "ICH" refers to the rat on day 7 after the collagenase injection but did not receive an injection of a test solution, "Vehicle" refers to the rat on day 7 after the injection of the saline instead of the test solution, and "Treatment" refers to the rat on day 7 after the injection of the test solution containing SMTP-7. In FIG. 8, the horizontal axis represents the number of days elapsed after the collagenase injection, and the vertical axis represents the percentage (%) of hematoma volume in brain volume at each time point. Furthermore, a perihematomal edema and the mass effect caused thereby were observed. The results are shown in FIG. 9. In FIG. 9, "ICH Baseline 24 hrs" refers to the image of the rat brain on day 1 after the collagenase injection, "TTT 1 week" refers to the brain image of the rat on day 7 after the injection of the test solution containing SMTP-7, "No TTT 1 week" refers to the brain image of the rat on day 7 that did not receive an injection of a test solution, and "Vehicle 1 week" refers to the brain image of the rat on day 7 after the injection of the saline instead of the test solution. As illustrated in FIG. 9, four samples are indicated by "TTT 1 week", three samples are indicated by "No TTT 1 week", and three samples are indicated by "Vehicle 1 week". Based on these observations, the volume of the brain edema was determined using ImageJ. The brain edema volume on day 7 after the collagenase injection is shown in FIG. 10. In FIG. 10, the vertical axis represents the percentage (%) of the brain edema volume in brain volume, "ICH Baseline" refers to the rat on day 1 after the collagenase injection, "ICH" refers to the rat on day 7 after the collagenase injection but did not receive an injection of a test solution, "Vehicle" refers to the rat on day 7 after the injection of the saline instead of the test solution, and "Treatment" refers to the rat on day 7 after the injection of the test solution containing SMTP-7. As shown in FIGS. 6 to 10, the individual injected with the test solution containing SMTP-7 exhibited considerable reductions in both hematoma size and edema size in the brain.

Example 4

Figure 11:
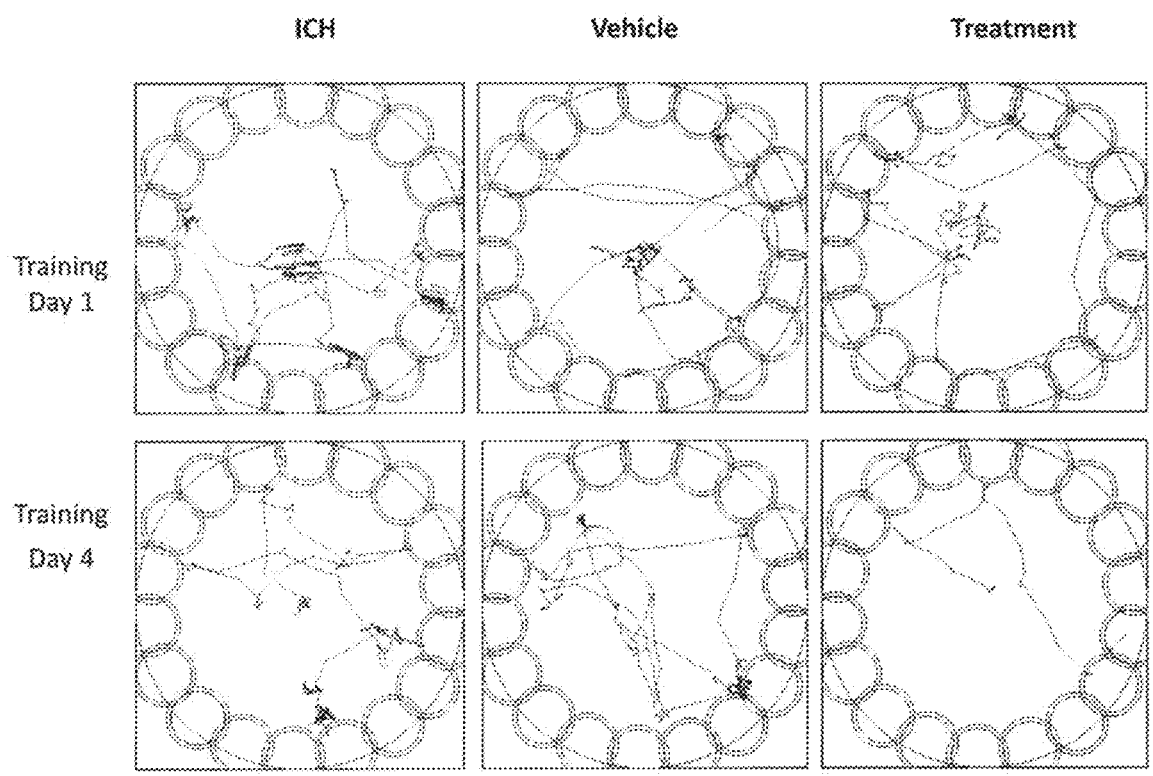
FIG. 11 illustrates a movement trajectory of a rat in a Barnes maze test using an animal model of cerebral hemorrhage, FIG. 12 provides a graph illustrating the latency required for a rat to reach an escape box in the Barnes maze test using an animal model of cerebral hemorrhage, FIG. 13 provides a graph showing the number of stays at wrong holes before a rat reaches an escape box in the Barnes maze test using an animal model of cerebral hemorrhage, FIG. 14 provides a graph illustrating the time-series variation in the latency required for a rat to reach an escape box in the Barnes maze test using an animal model of cerebral hemorrhage, FIG. 15 provides a graph illustrating the time-series variation in the number of stays at wrong holes before a rat reaches an escape box in the Barnes maze test using an animal model of cerebral hemorrhage, FIG. 16 provides a graph illustrating the score of rats in each group in a LAN cable walking test using an animal model of cerebral hemorrhage, FIG. 17 provides images of brain sections stained with hematoxylin and eosin (HE) in a study using an animal model of cerebral hemorrhage, FIG. 18 provides a graph illustrating the hematoma area in images of brain sections stained with hematoxylin and eosin (HE) in a study using an animal model of cerebral hemorrhage, FIG. 19 provides the double-stained images of brain sections with luxol fast blue and cresyl violet in a study using an animal model of cerebral hemorrhage, FIG. 20 provides a graph illustrating the myelin density (mean values at each of sites ipsilateral and contralateral to the collagenase injection site in the white matter) in the double-stained images of brain sections with luxol fast blue and cresyl violet in a study using an animal model of cerebral hemorrhage, FIG. 21 provides a graph illustrating the myelin density (per individual value in the center of white matter) in the double-stained images of brain sections with luxol fast blue and cresyl violet in a study using an animal model of cerebral hemorrhage, FIG. 22 provides antibody-stained images of brain sections with an anti-cleaved caspase-3 antibody in a study using an animal model of cerebral hemorrhage, FIG. 23 provides antibody-stained images of brain sections with an anti-cleaved caspase-3 antibody in a study using an animal model of cerebral hemorrhage, FIG. 24 provides a graph illustrating the number of immunopositive cells per 100 $\mu m^2$ in an antibody-stained image of a brain section with an anti-cleaved caspase-3 antibody in a study using an animal model of cerebral hemorrhage, FIG. 25 provides antibody-stained images of brain sections with an anti-GFAP antibody in a study using an animal model of cerebral hemorrhage, FIG. 26 provides antibody-stained images of brain sections with an anti-GFAP antibody in a study using an animal model of cerebral hemorrhage, FIG. 27 provides a graph illustrating the number of immunopositive cells per 100 $\mu m^2$ in an antibody-stained image of a brain section with an anti-GFAP antibody in a study using an animal model of cerebral hemorrhage, FIG. 28 provides antibody-stained images of brain sections with an anti-Iba-1 antibody in a study using an animal model of cerebral hemorrhage, FIG. 29 provides antibody-stained images of brain sections with an anti-Iba-1 antibody in a study using an animal model of cerebral hemorrhage, and FIG. 30 provides a graph illustrating the number of immunopositive cells per 100 μm$^2$ in an antibody-stained image of a brain section with an anti-Iba-1 antibody in a study using an animal model of cerebral hemorrhage.
Figure 12:
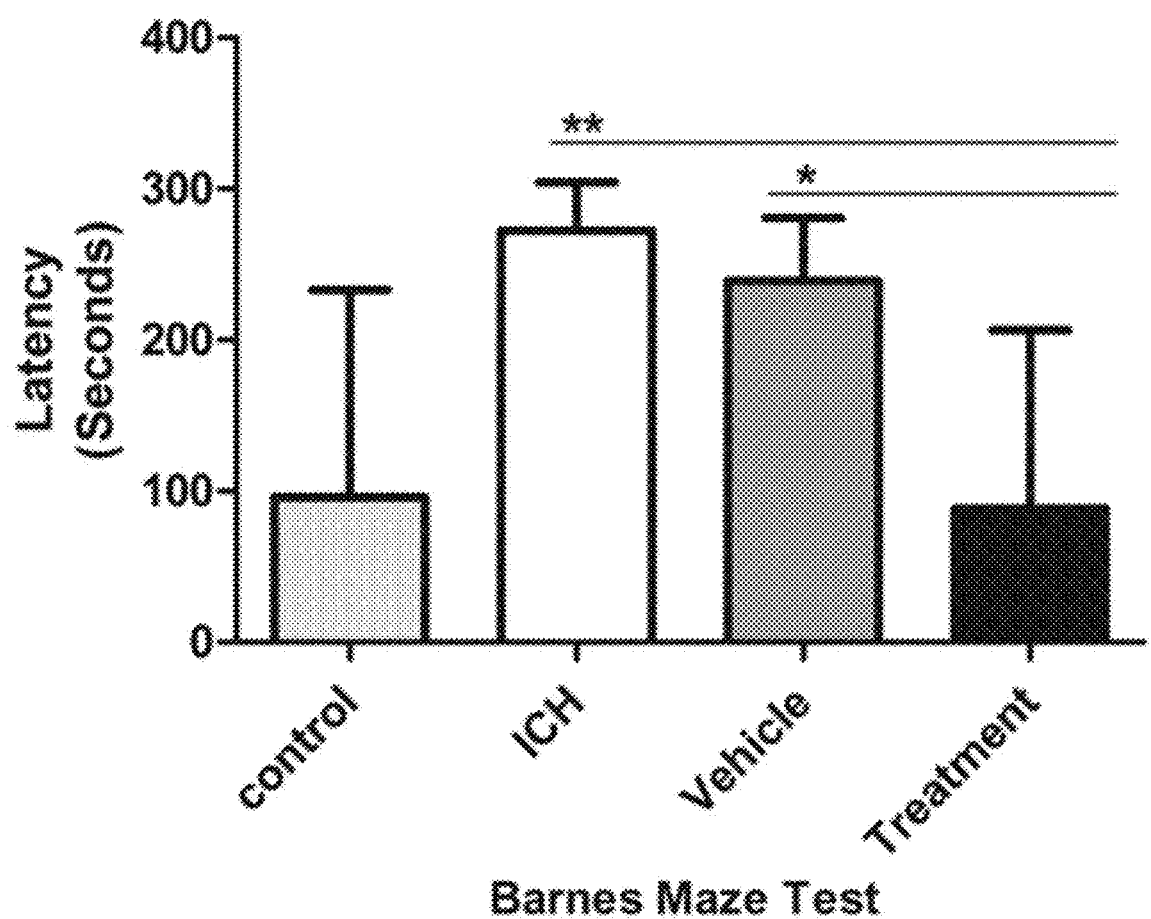
Figure 13:
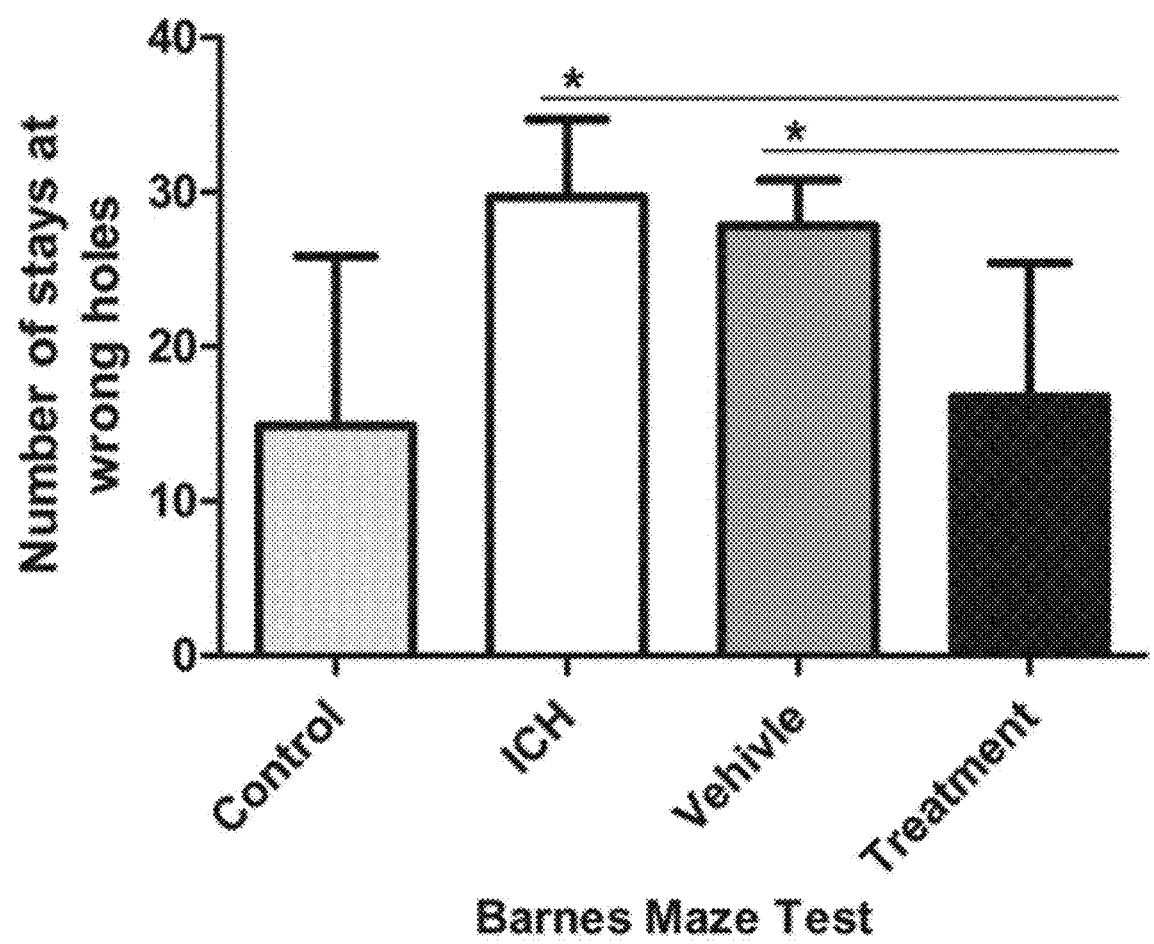
Figure 14:
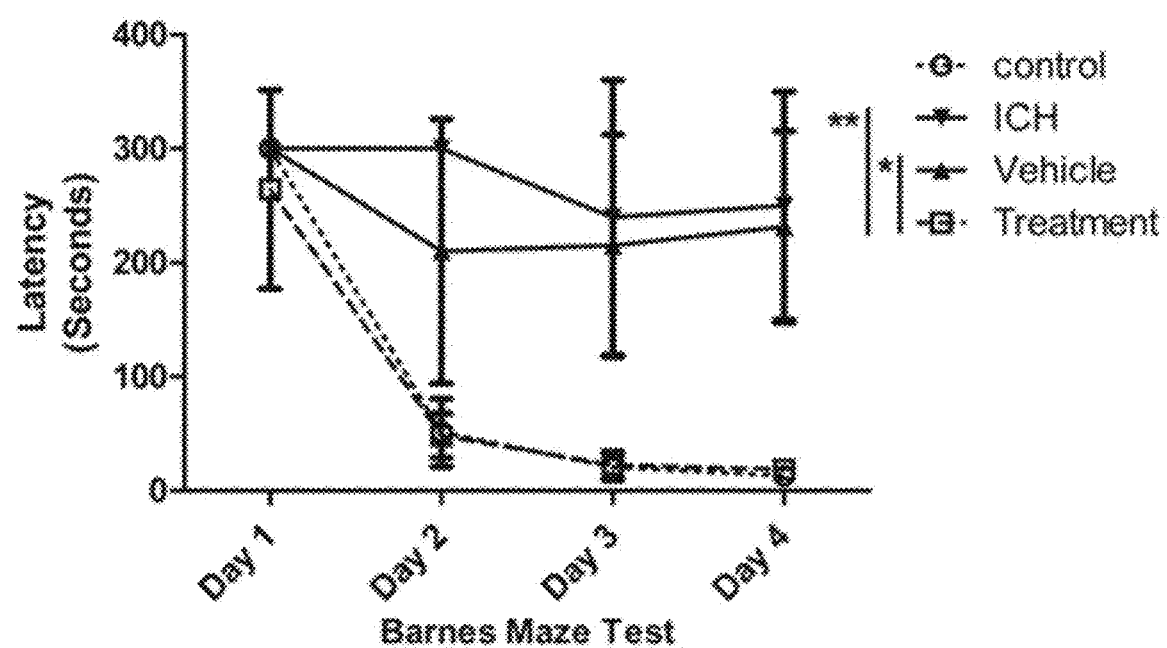
Figure 15:
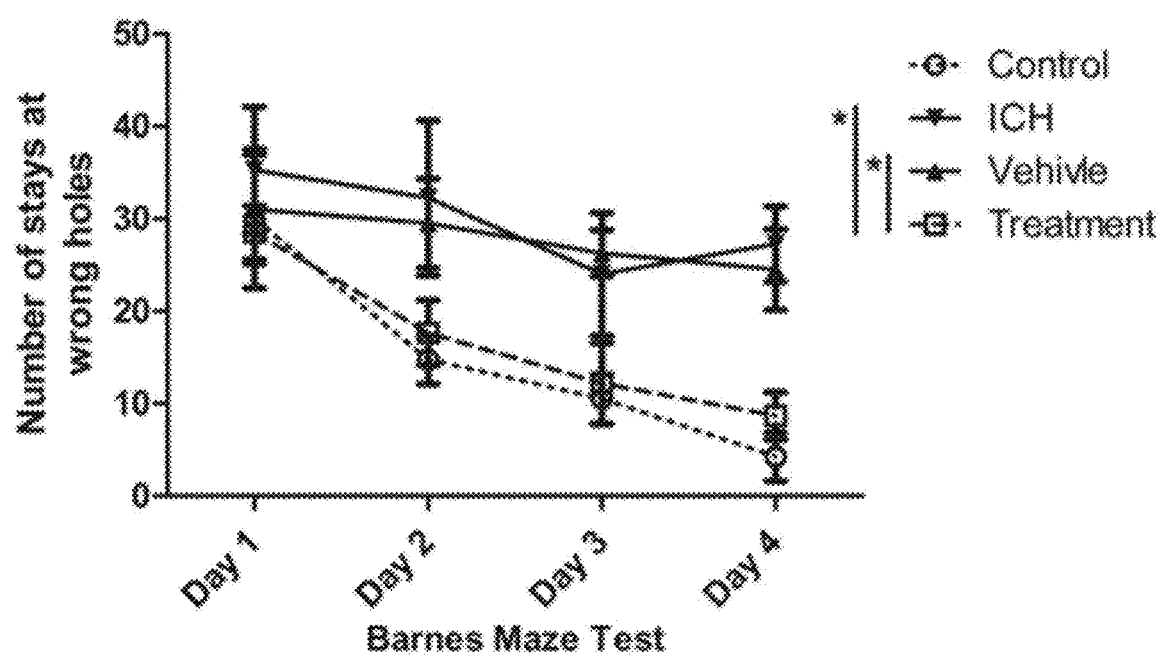

Injections of the collagenase and the test solution were performed in the same manner as in Example 1, and the Barnes Maze Test was performed on day 7 after the collagenase injection. This test allows for evaluation of spatial learning and memory. The test was conducted using a gray acrylic platform with a diameter of 122 cm, and the acrylic platform had 18 holes arranged on the periphery. The behavior of a rat was observed by a camera placed above the rat's head. Evaluation was made based on the latency to find the location of an escape box. The test was performed twice a day to train the rat, and the test was repeated up to 10 days after the collagenase injection. In each test, the test was started to place a rat in a start box in the center of the maze, and that the rat was allowed to stay in the start box for the first 30 seconds and then allowed to explore the maze freely. When the rat reached the escape box, the rat was allowed to stay in the escape box for 30 seconds, and returned to the breeding cage. When the rat did not reach the escape box within the maximum test time of 300 seconds, the rat was picked up and allowed to stay in the escape box for 30 seconds and returned to the breeding cage. The latency to reach the escape box and the number of stays at wrong holes of the rat were evaluated. In Example 4, the rat with no treatment was also tested as the control. The movement trajectories of the rats on day 7 (Training Day 1 in the figure) and on day 10 (Training Day 4 in the figure) after the collagenase injection are shown in FIG. 11. In FIG. 11, "ICH" refers to the rat that did not receive any injection of a test solution after the collagenase injection, "Vehicle" refers to the rat injected with the saline instead of the test solution, and "Treatment" refers to the rat injected with the test solution containing SMTP-7. The latency required to reach the escape box and the number of stays at wrong holes on day 10 after the collagenase injection are shown in FIG. 12 and FIG. 13. In FIGS. 12 to 15, "ICH" refers to the rat that did not receive any injection of a test solution after the collagenase injection, "Vehicle" refers to the rat injected with the saline instead of the test solution, "Treatment" refers to the rat injected with the test solution containing SMTP-7, and "control" refers to the healthy rat that did not receive a collagenase injection. The time-series variation in the latency required and the number of stays at wrong holes, that is, the degree of learning, for each day from day 7 to day 10 after the collagenase injection are shown in FIG. 14 and FIG. 15. Day 1 in FIG. 14 and FIG. 15 refers to the seventh day after the collagenase injection. As shown in FIGS. 11 to 15, the individual injected with the test solution containing SMTP-7 exhibited a considerable improvement in learning ability.

Example 5

Figure 16:
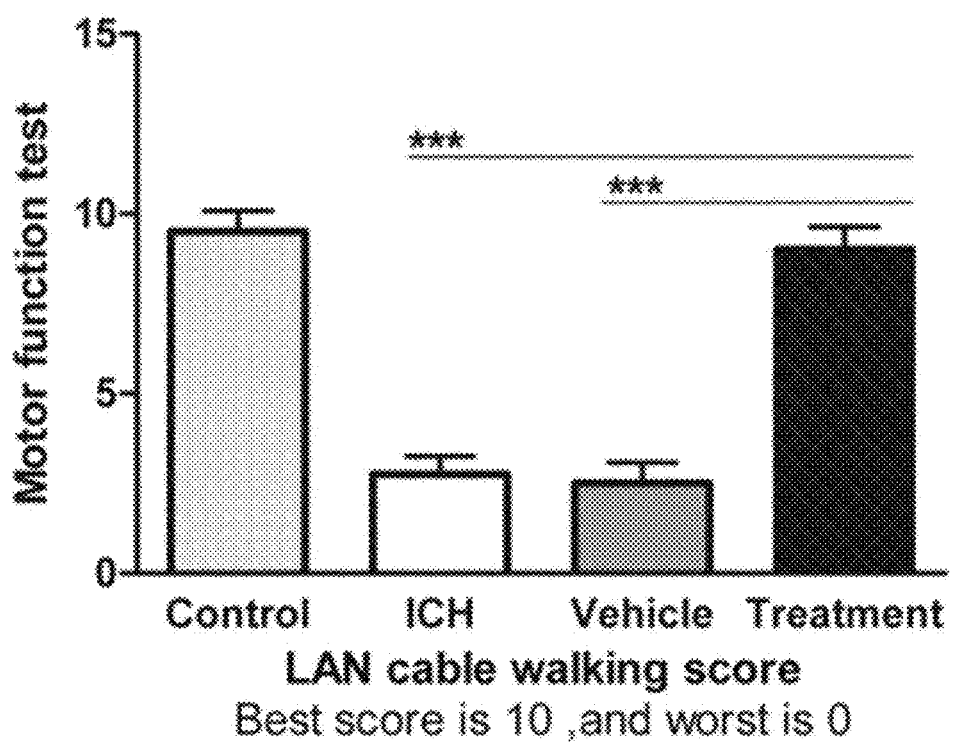

Injections of the collagenase and the test solution were performed in the same manner as in Example 1. The motor function of the rat was evaluated based on walking of the rat on a local area network (LAN) cable. The rat was placed on the LAN cable along the length direction thereof at a height of 60 cm from the floor, and observed for hemiparesis, posture on the cable, activity, and toughness for 60 seconds. The following criteria were used to assign a score for each item, and the total score (from 0 to 10 points) was obtained.
<Right-sided Paralysis>
[Front legs]
0 points: Right-sided paralysis was observed
1 point: No right-sided paralysis was observed
[Hind legs]
0 points: Right-sided paralysis was observed
1 point: No right-sided paralysis was observed
<Posture on Cable>
0 points: Cannot hang on for 10 seconds
1 point: Can hang for 10 seconds or more, but cannot maintain a posture in a direction crossing the LAN cable for 30 seconds
2 points: Can maintain a posture in a direction crossing the LAN cable for 30 seconds or more, but cannot maintain a posture along the LAN cable for 30 seconds.
3 points: Can maintain a posture along the LAN cable for 30 seconds or more
<Activity>
[Continuity of Activity]
0 points: Cannot remain active for 10 seconds
1 point: Can remain active for 10 seconds or more
[Posture Recovery]
0 points: Cannot recover from unbalanced posture
1 point: Can recover from unbalanced posture
[Travel Distance]
0 points: Cannot travel 10 cm
1 point: Can travel 10 cm or more
<Toughness>
0 points: Falling from LAN cable
2 points: Not falling from LAN cable
The results are shown in FIG. 16. In FIG. 16, the vertical axis represents the total score described above. In Example 5, rats that did not receive any treatment were also tested as controls. In FIG. 16, "ICH" refers to the rat that did not receive any injection of a test solution after the collagenase injection, "Vehicle" refers to the rat injected with the saline instead of the test solution, "Treatment" refers to the rat injected with the test solution containing SMTP-7, and "Control" refers to the healthy rat that did not receive a collagenase injection. As shown in FIG. 16, the individual injected with the test solution containing SMTP-7 exhibited a considerable improvement in motor performance.

Example 6

Figure 17:
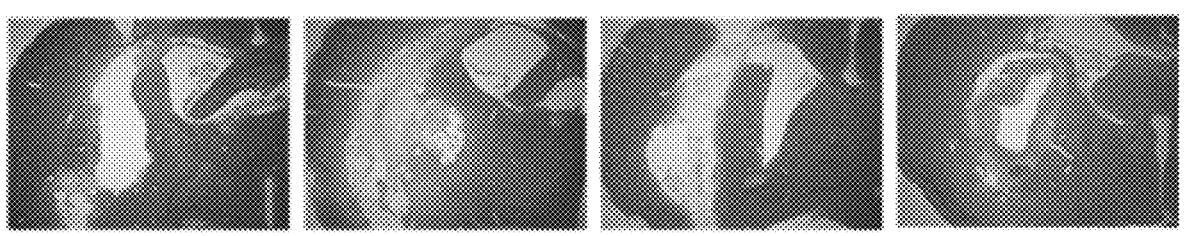
Figure 17:
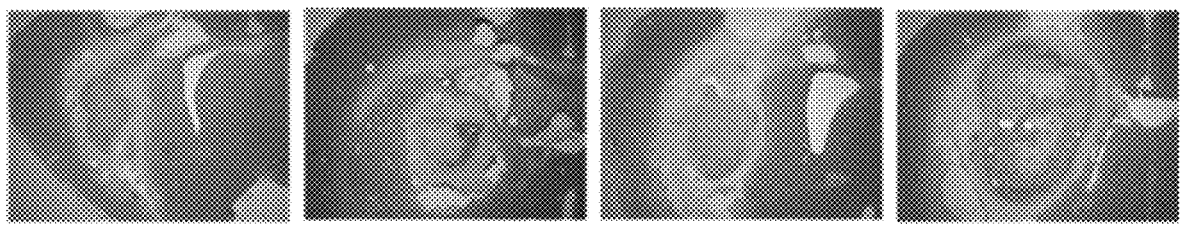
Figure 17:
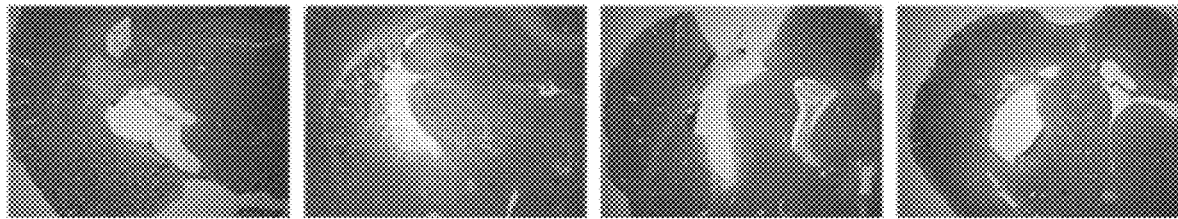
Figure 18:
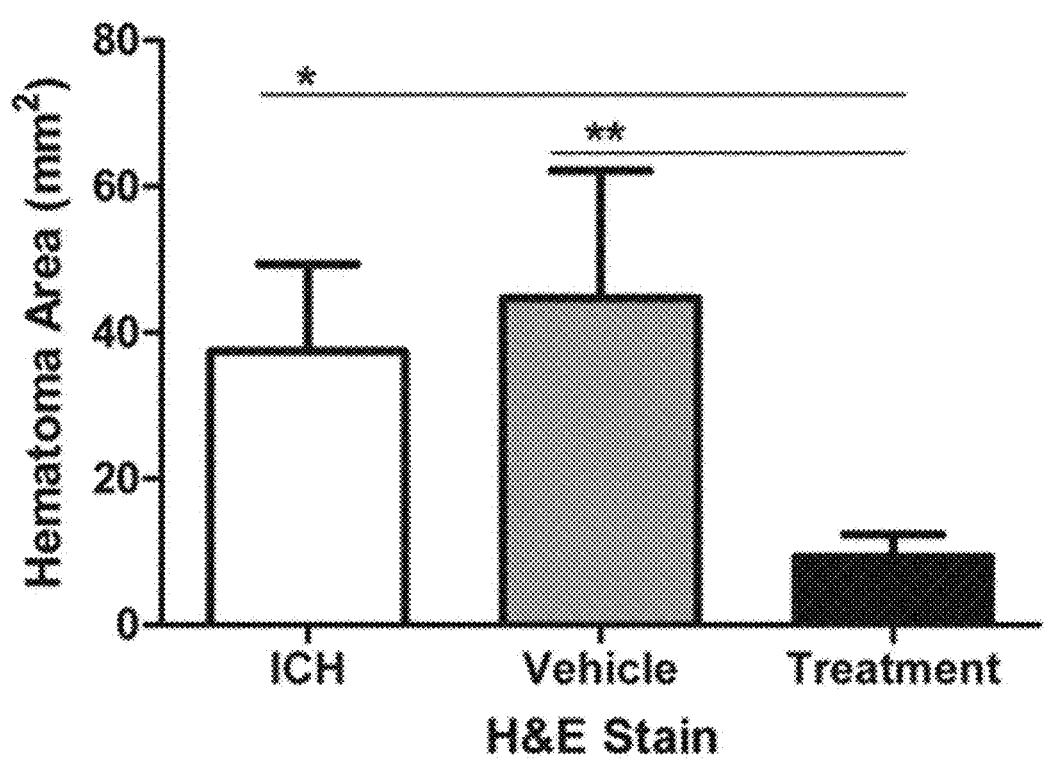

Injections of the collagenase and the test solution were performed in the same manner as in Example 1, and brain tissue samples on day 7 after the collagenase injection were obtained. Specifically, rats were deeply anesthetized with isoflurane, perfused with saline, and further perfused with 4% formaldehyde in 0.1 M phosphate-buffered saline (PBS; pH 7.4). The brain was taken out and post-fixed overnight at 4° C. with the above PBS solution containing 4% formaldehyde as the fixative solution, and stored in 10%, 20%, and 30% sucrose in PBS until the tissue sank. Sections of about 2 mm thick were obtained by cutting the brain in the coronal plane with a BRAIN SLICER (manufactured by Harvard Apparatus Inc.), embedded in an optimal cutting temperature (OCT) compound, frozen in liquid nitrogen, and cut into 10- to 12-µm-thick sections with a cryostat microtome. Coronal sections (including 3 mm lateral to the midline) at the level of the bregma were stained with hematoxylin-eosin (HE). The micrograph is shown in FIG. 17. The indicated scale is 100 µm (the same applies to the subsequent micrographs). In FIG. 17, "ICH" refers to the rat that did not receive any injection of a test solution after the collagenase injection, "Vehicle" refers to the rat injected with the saline instead of the test solution, and "SMTP-7" refers to the rat injected with the test solution containing SMTP-7. The hematoma area (mm$^2$) measured using ImageJ on this section is illustrated in FIG. 18. In FIG. 18, the vertical axis represents the area (mm$^2$) of the hematoma region identified by HE staining. "ICH" refers to the rat that did not receive any injection of a test solution after the collagenase injection, "Vehicle" refers to the rat injected with the saline instead of the test solution, and "Treatment" refers to the rat that injected with the test solution containing SMTP-7. As shown in FIG. 17 and FIG. 18, the individual injected with the test solution containing SMTP-7 exhibited a considerable reduction in hematoma size.

Example 7

Figure 19:
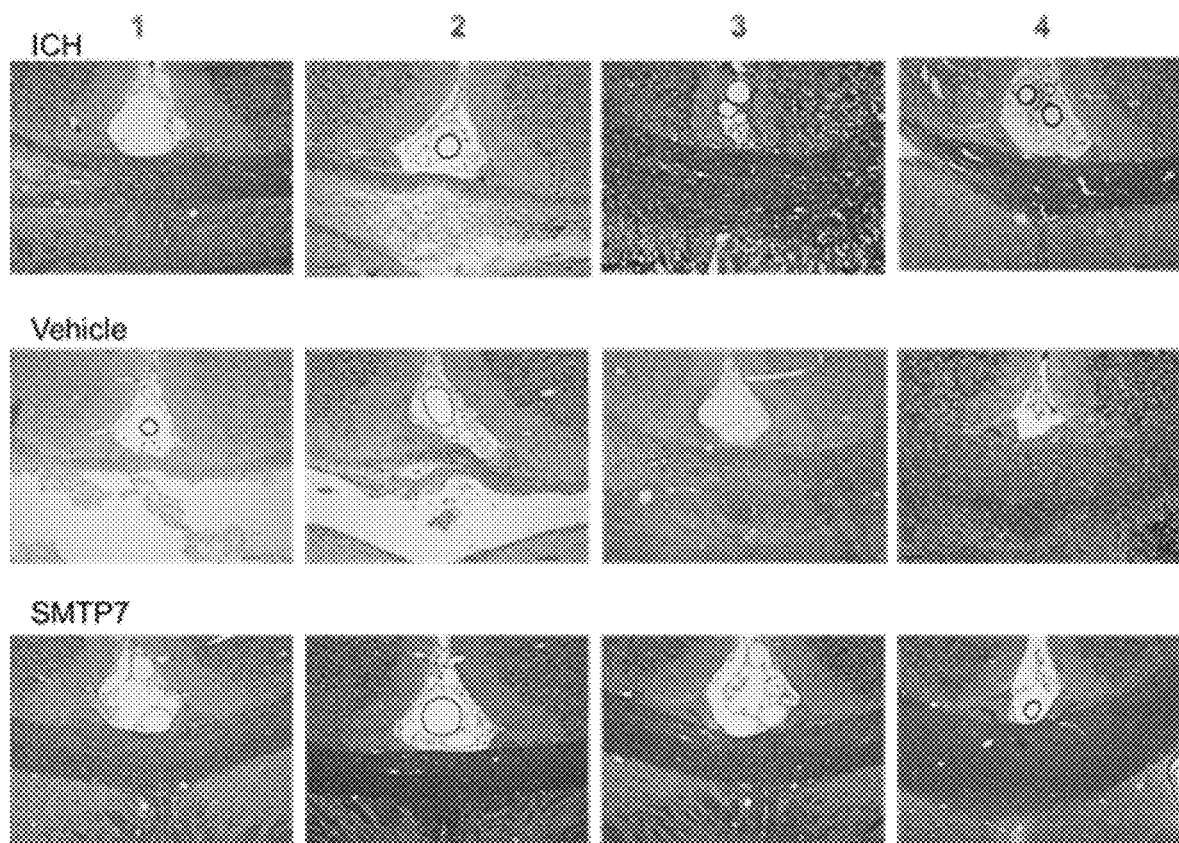
Figure 20:
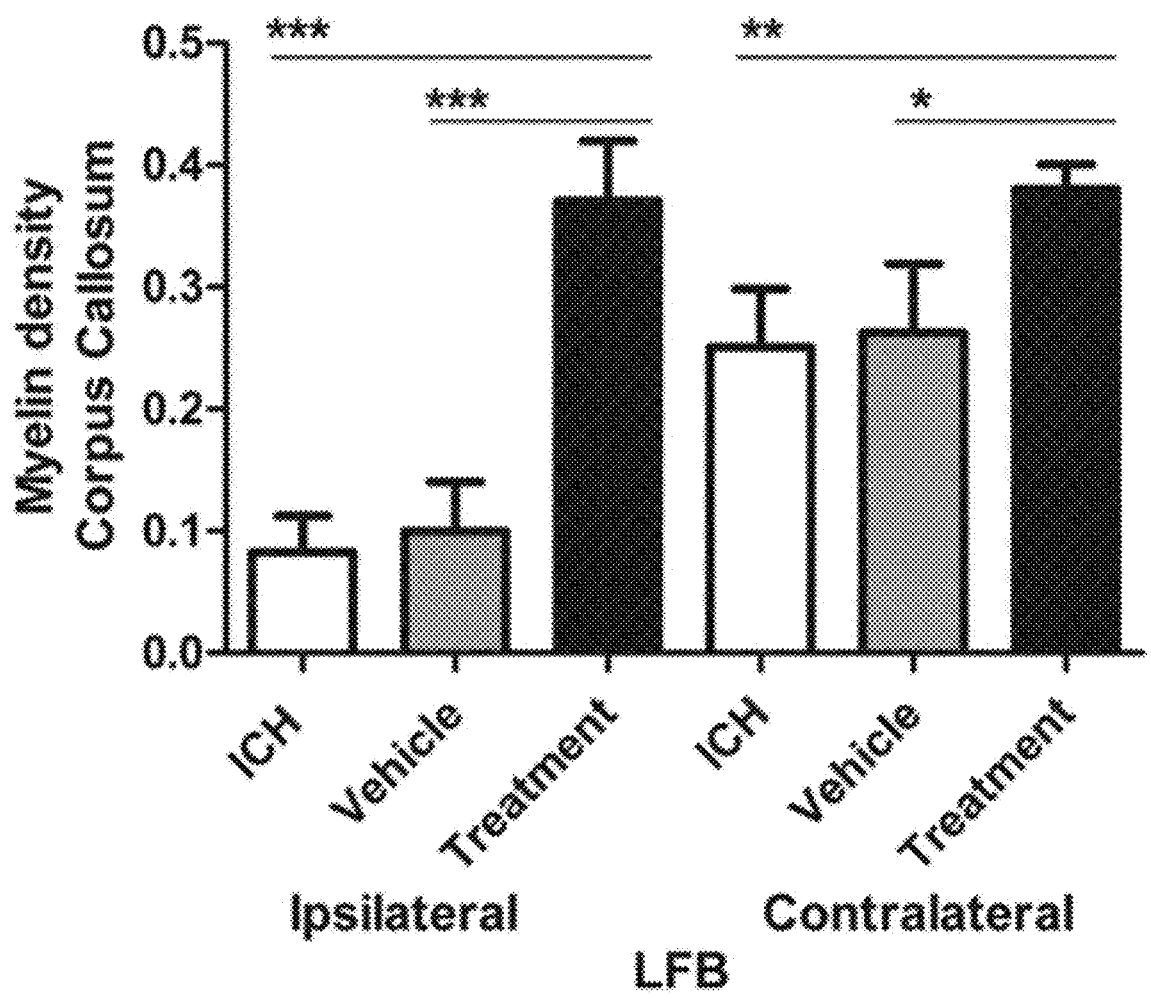
Figure 21:
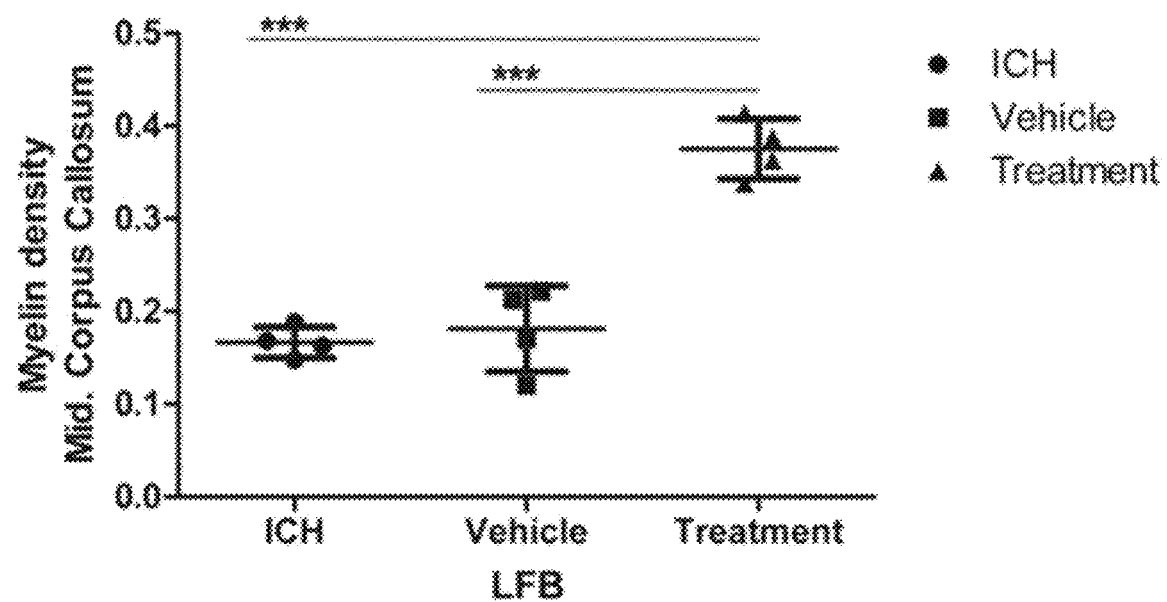

10-µm-thick sections prepared in the same manner as in Example 6 were double-stained with luxol fast blue and cresyl violet to observe white matter lesions (demyelination) in the medial part of the corpus callosum. The micrographs are shown in FIG. 19. In FIG. 19, "ICH" refers to the rat that did not receive any injection of a test solution after the collagenase injection, "Vehicle" refers to the rat injected with the saline instead of the test solution, and "SMTP-7" refers to the rat injected with the test solution containing SMTP-7. The myelin density in the white matter was measured at the site ipsilateral to the collagenase injection site, the site contralateral to the collagenase injection site, and the central site. The results are shown in FIG. 20 and FIG. 21. In FIG. 20, the vertical axis represents the myelin density in the white matter (mean value). In FIG. 20, "Ipsilateral" represents the side ipsilateral to the collagenase injection site, and "Contralateral" represents the side contralateral to the collagenase injection site (the same applies hereinafter). In FIG. 21, the vertical axis represents the myelin density in the center of the white matter (per individual). In FIG. 20 and FIG. 21, "ICH" refers to the rat that did not receive any injection of a test solution after the collagenase injection, "Vehicle" refers to the rat injected with the saline instead of the test solution, and "Treatment" refers to the rat injected with the test solution containing SMTP-7. As shown in FIGS. 19 to 21, the individual injected with the test solution containing SMTP-7 exhibited a considerable suppression of white matter lesions.

Example 8

Figure 22:
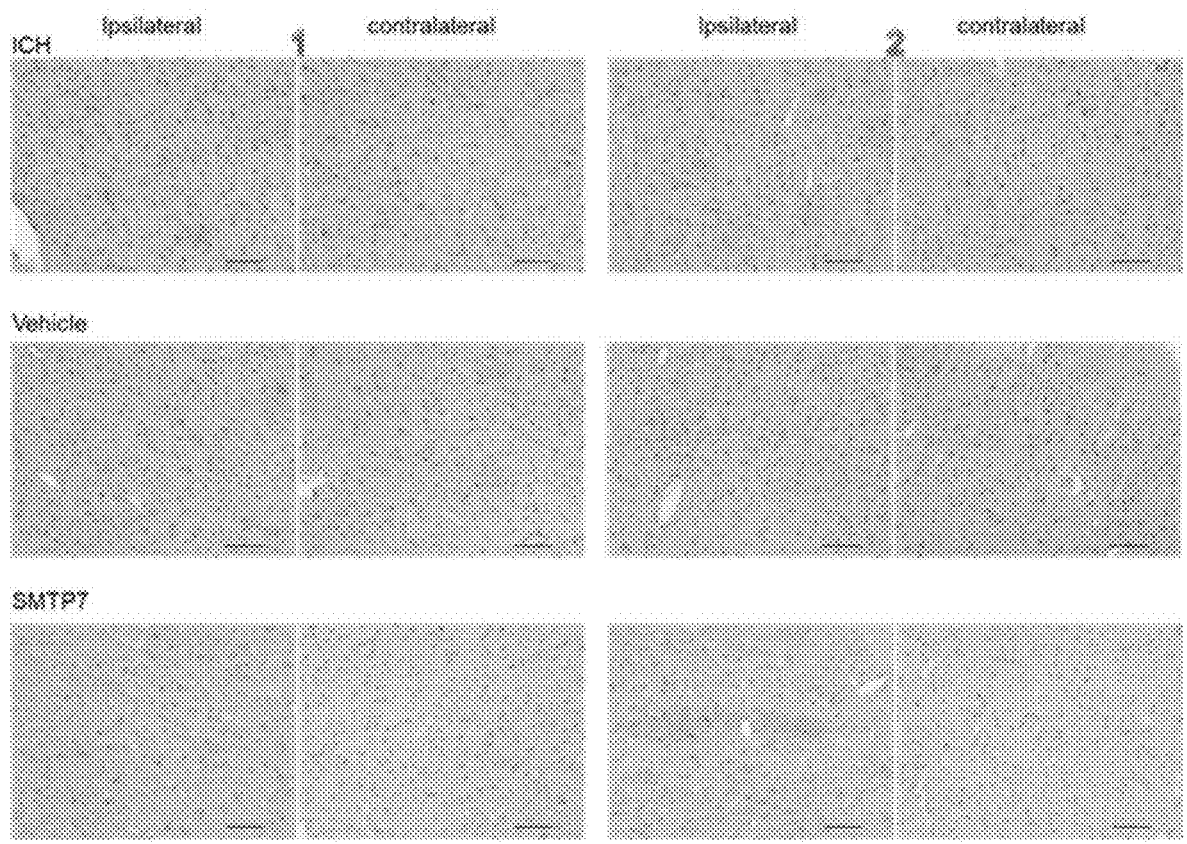
Figure 23:
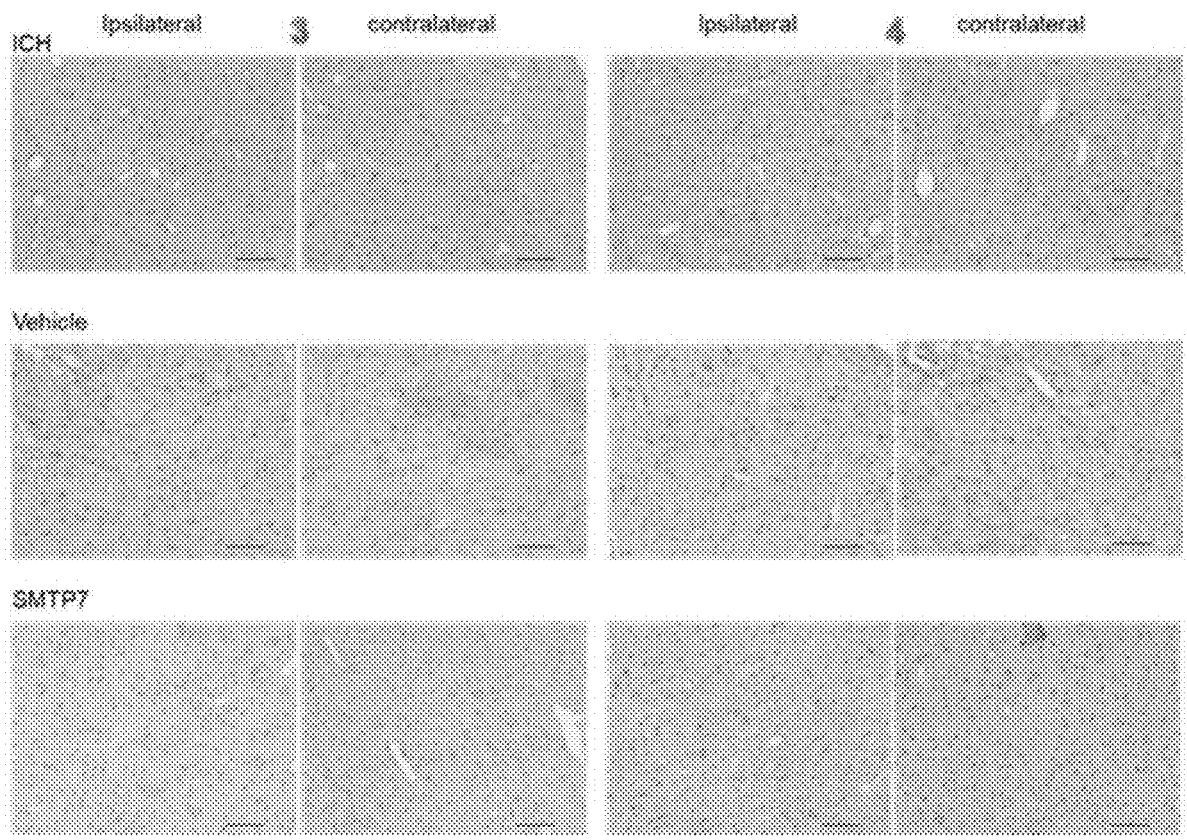

10- to 12-µm-thick sections at the level of the bregma (including 3 mm lateral to the midline) prepared in the same manner as in Example 6 were treated with a 10% bovine serum albumin (BSA) solution for 2 hours at room temperature to block non-specific bonding sites, and the blocked sections were incubated with an anti-cleaved caspase-3 (Asp175) antibody (9661 from Cell Signaling Technology Inc.). Furthermore, the sections were exposed to a biotinylated secondary antibody (1:200; Vector Laboratory) and visualized with 0.01% diaminobenzidine tetrahydrochloride and 0.005% hydrogen peroxide in 50 mmol/L Tris-HCl (pH=7.6). Micrographs are shown in FIG. 22 and FIG. 23. In FIG. 22 and FIG. 23, "ICH" refers to the rat that did not receive any injection of a test solution after the collagenase injection, "Vehicle" refers to the rat injected with the saline instead of the test solution, and "Treatment" refers to the rat injected with the test solution containing SMTP-7.

Figure 24:
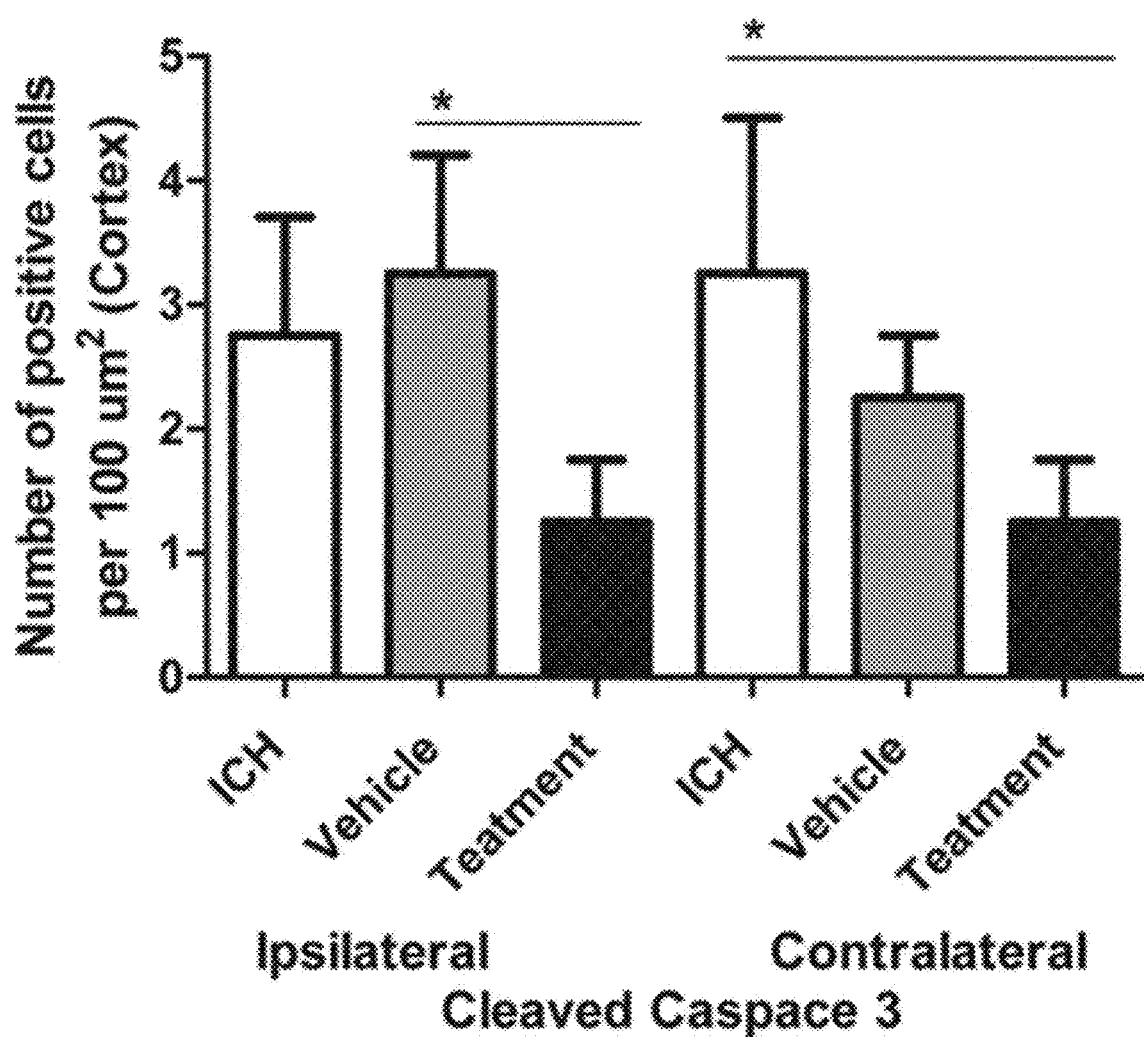

Furthermore, two 100 µm$^2$ regions of interest (ROIs) were randomly selected in the cortex, the number of immunopositive cells in each ROI was counted, and then the average value was calculated. In FIG. 24, the vertical axis represents the number of immunopositive cells per 100 µm$^2$ of ROI, "ICH" refers to the rat that did not receive any injection of a test solution after the collagenase injection, "Vehicle" refers to the rat injected with the saline instead of the test solution, and "Treatment" refers to the rat injected with the test solution containing SMTP-7. The results are shown in FIG. 24. As shown in FIGS. 22 to 24, the number of cells expressing caspase-3, an indicator of apoptosis, is considerably reduced both ipsilaterally and contralaterally in the individual injected with the test solution containing SMTP-7.

Example 9

Figure 25:
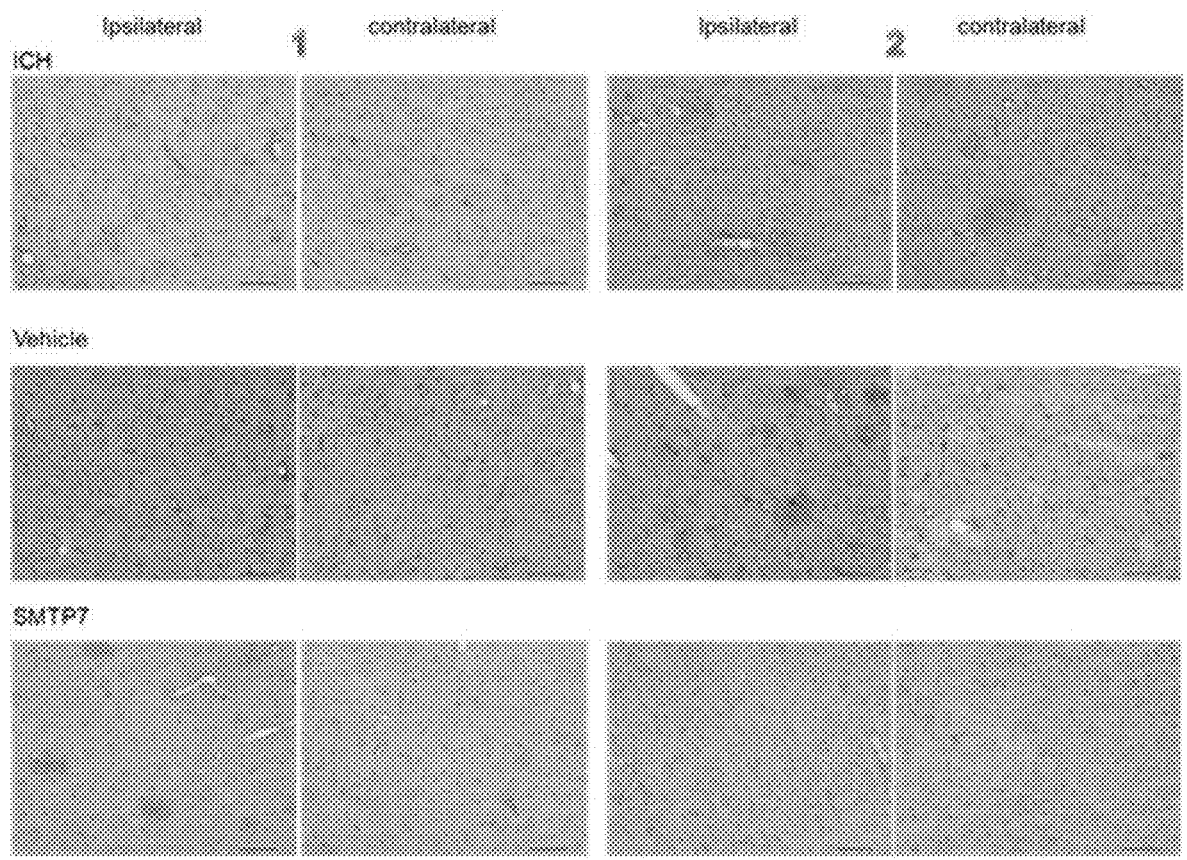
Figure 26:
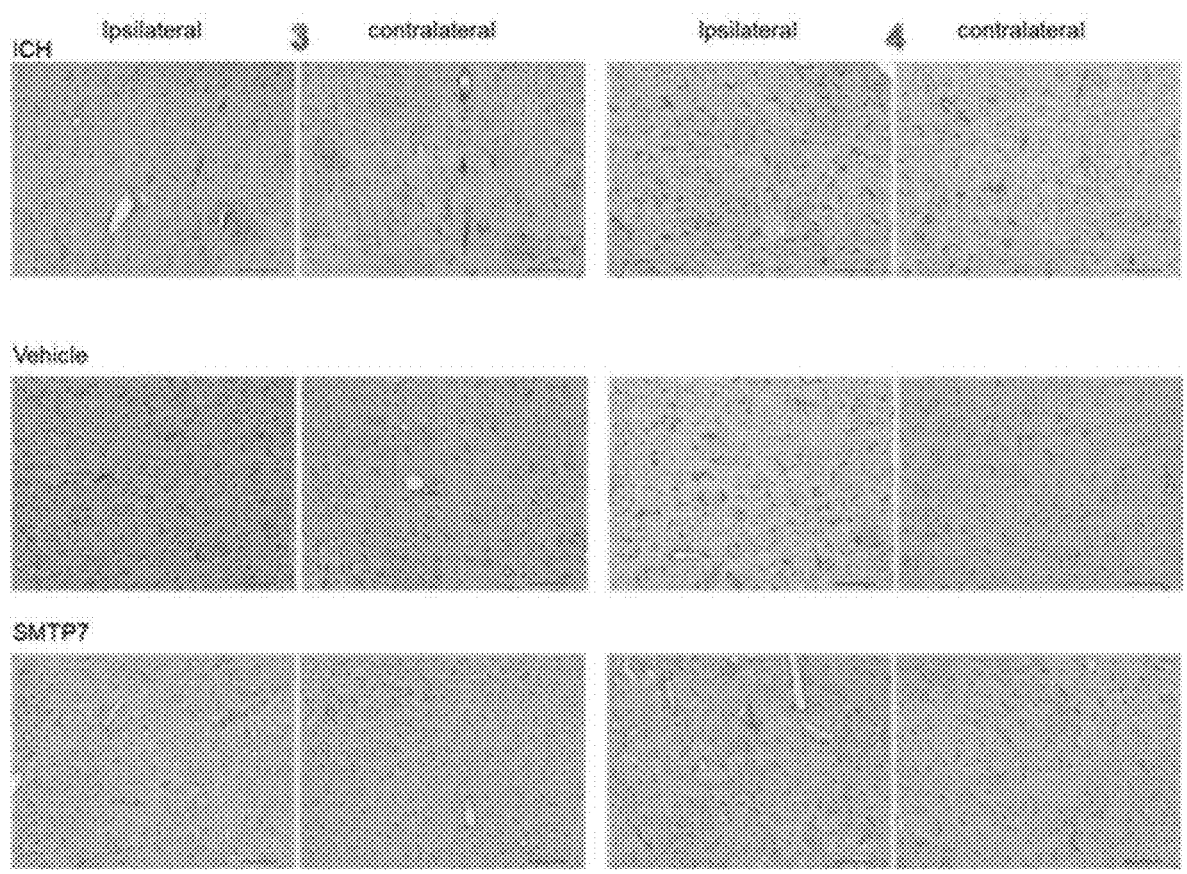
Figure 27:
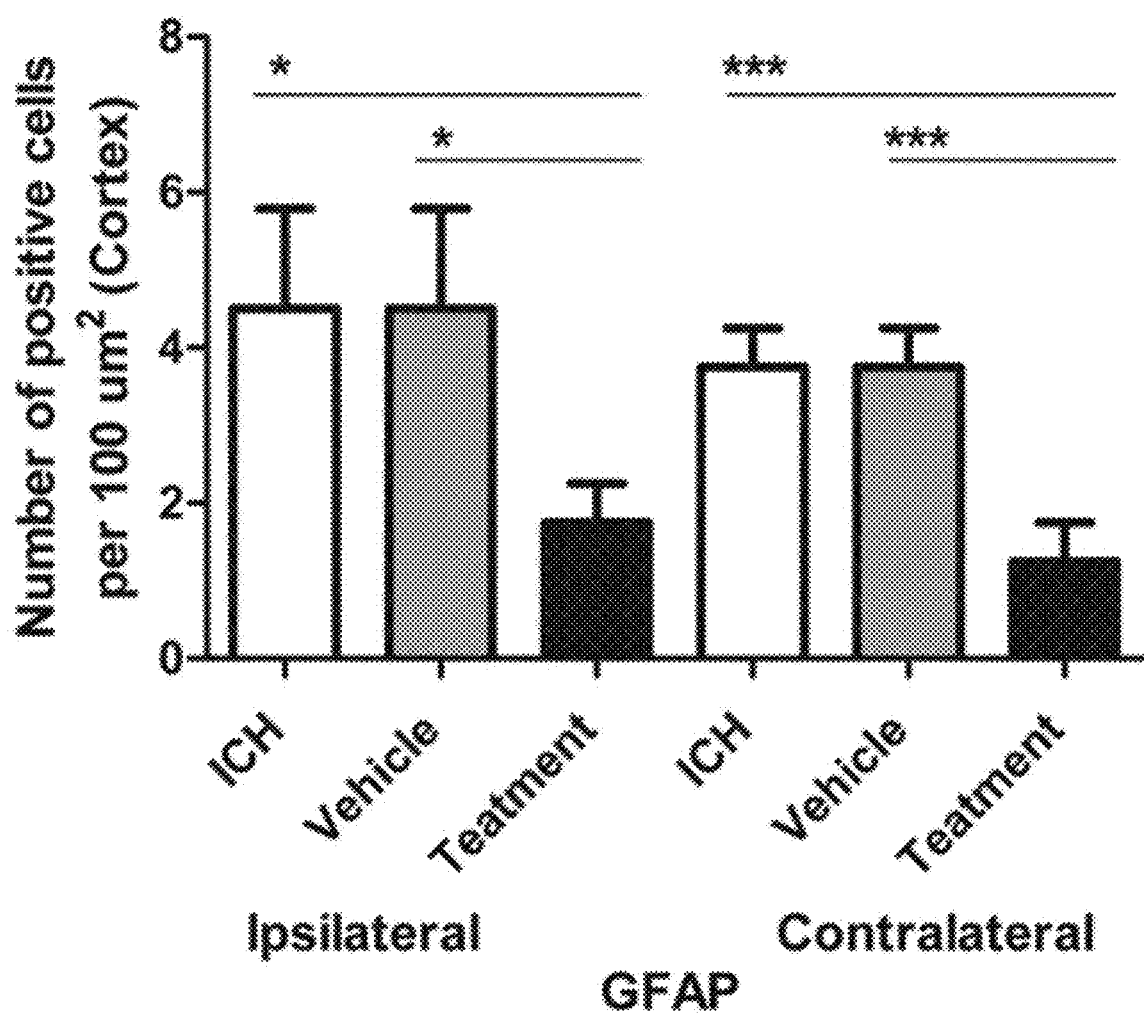

Antibody staining test was performed in the same manner as in Example 8, except that anti-GFAP antibody (axtrocyte; mouse mAb 3670; Cell Signaling Technology) was used instead of the anti-cleaved caspase-3 antibody (Asp175). Micrographs are shown in FIG. 25 and FIG. 26, and the number of immunopositive cells is shown in FIG. 27. As shown in FIGS. 25 to 27, the result of immunostaining with the anti-GFAP antibody, an astrocyte marker, indicates that neuronal damage is considerably suppressed in the individual injected with the test solution containing SMTP-7.

Example 10

Figure 28:
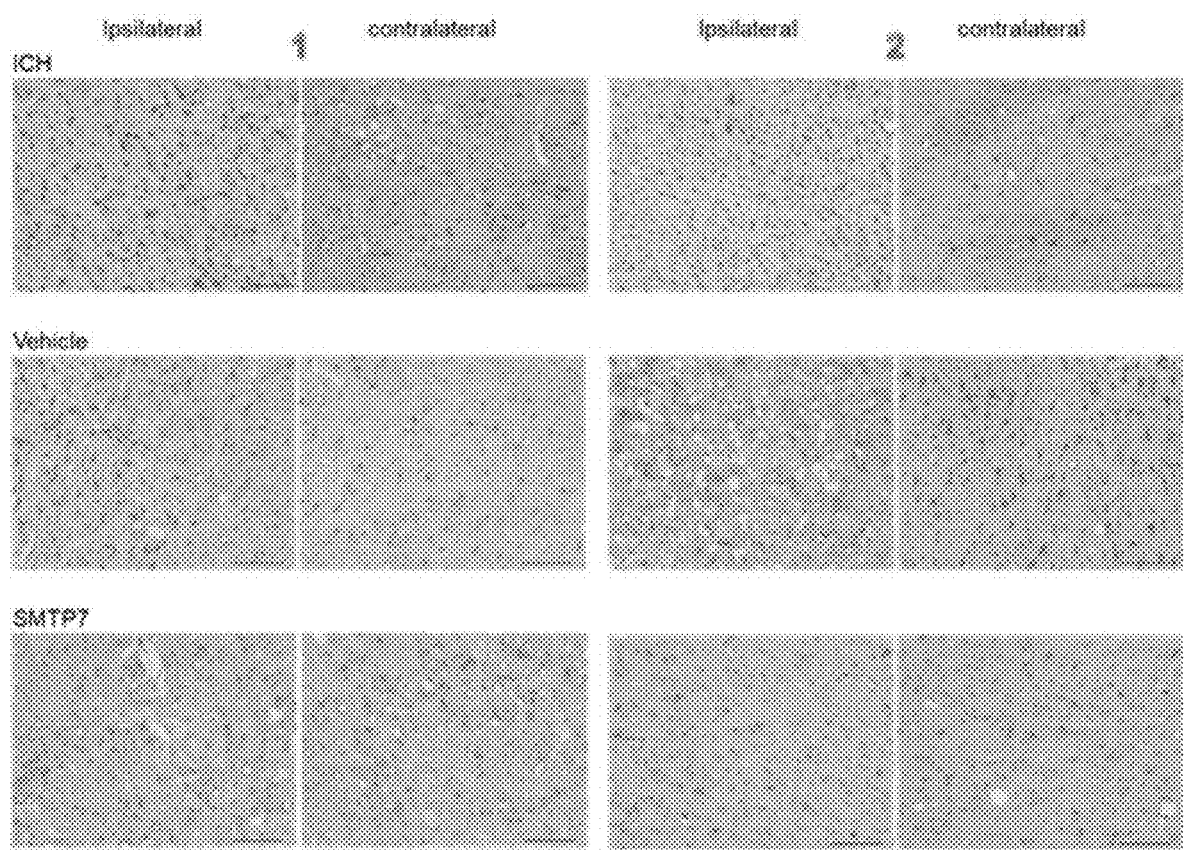
Figure 29:
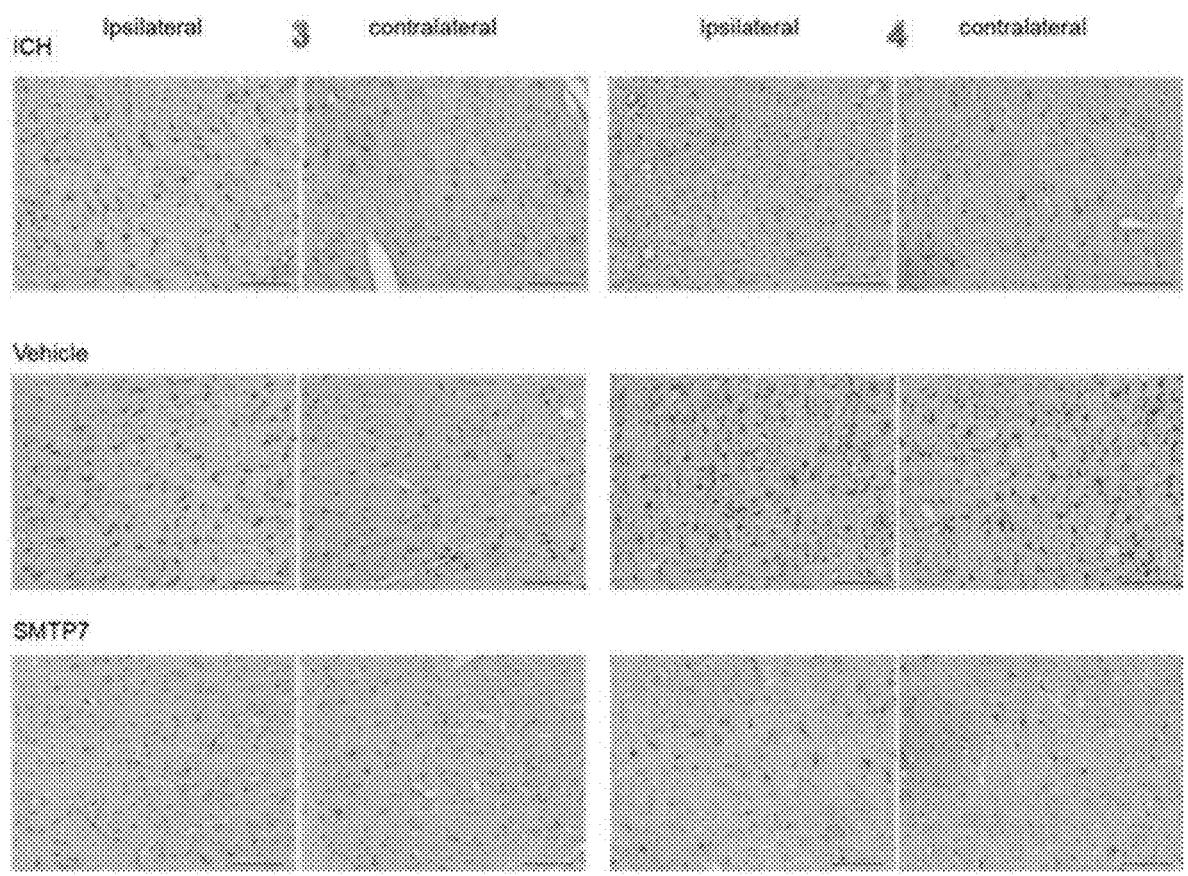
Figure 30:
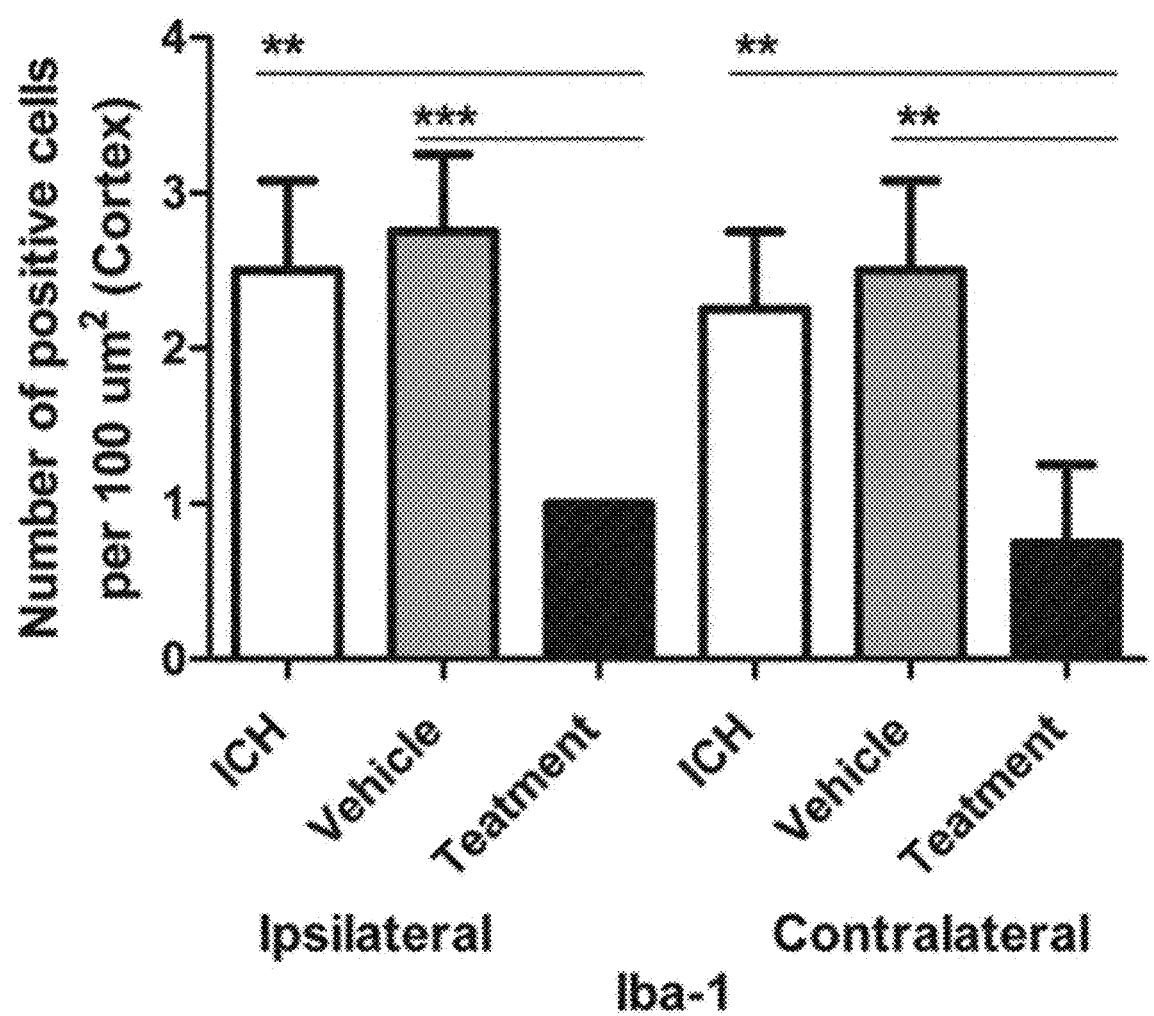

Antibody staining test was performed in the same manner as in Example 8, except that an anti-Iba-1 antibody (019-19741; Wako; Cell Signaling Technology) was used instead of the anti-cleaved caspase-3 antibody (Asp175). Micrographs are shown in FIG. 28 and FIG. 29, and the number of immunopositive cells is shown in FIG. 30. As shown in FIGS. 28 to 30, the result of immunostaining with the anti-Iba-1 antibody, a macrophage/microglia-specific marker, indicates that inflammation is also considerably suppressed in the individual injected with the test solution containing SMTP-7.

From the above results, it can be seen that the compound represented by Formula (I) has an favorable therapeutic effect and a preventive effect on cerebral hemorrhage.

The disclosure of Japanese Patent Application No. 2019-209932, filed on Nov. 20, 2019, is incorporated herein by reference in its entirety.

All publications, patent applications, and technical standards mentioned in this specification are herein incorporated by reference to the same extent as if each individual publication, patent application, or technical standard was specifically and individually indicated to be incorporated by reference.

What is claimed is:

1. A method of treating a cerebral hemorrhage in a subject in need of, comprising administering SMTP-7 or a pharmaceutically acceptable salt thereof, in an amount effective for treating the cerebral hemorrhage, to the subject suffering from the cerebral hemorrhage, wherein the method reduces or eliminates a hematoma, an edema, or both a hematoma and an edema, and wherein treating the cerebral hemorrhage is independent of treating a cerebral infarction.

2. The method according to claim 1, wherein the cerebral hemorrhage is intracerebral hemorrhage.

3. The method according to claim 1, wherein SMTP-7 or a pharmaceutically acceptable salt thereof is administered intracerebrally.

4. The method according to claim 1, wherein the method reduces or eliminates a hematoma.

5. The method according to claim 1, wherein the method reduces or eliminates an edema.

6. The method according to claim 1, wherein the method reduces or eliminates both a hematoma and an edema.

7. The method according to claim 1, wherein the cerebral hemorrhage does not associate with a cerebral infarction.

* * * * *